United States Patent
Adams et al.

(10) Patent No.: US 12,303,323 B2
(45) Date of Patent: *May 20, 2025

(54) ULTRASOUND PROBE WITH AN INTEGRATED NEEDLE ASSEMBLY AND A COMPUTER PROGRAM PRODUCT, A METHOD AND A SYSTEM FOR PROVIDING A PATH FOR INSERTING A NEEDLE OF THE ULTRASOUND PROBE

(71) Applicant: Dandelion Technologies, LLC, Vero Beach, FL (US)

(72) Inventors: Paul Adams, Vero Beach, FL (US); Christopher Vetter, Dublin, OH (US); Michael Andrew Holtman, McLean, VA (US)

(73) Assignee: DANDELION TECHNOLOGIES LLC, Vero Beach, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 19/007,186

(22) Filed: Dec. 31, 2024

(65) Prior Publication Data

US 2025/0134490 A1 May 1, 2025

Related U.S. Application Data

(60) Division of application No. 17/542,080, filed on Dec. 3, 2021, which is a continuation-in-part of application
(Continued)

(51) Int. Cl.
*A61B 8/08* (2006.01)
*A61B 8/00* (2006.01)
*A61B 17/34* (2006.01)

(52) U.S. Cl.
CPC .......... *A61B 8/0841* (2013.01); *A61B 8/4227* (2013.01); *A61B 8/4254* (2013.01);
(Continued)

(58) Field of Classification Search
None
See application file for complete search history.

(56) References Cited

U.S. PATENT DOCUMENTS 7,129,389 B1 * 10/2006 Watson ............... A61F 13/0276
602/46
7,846,103 B2 12/2010 Cannon, Jr. et al.
(Continued)

FOREIGN PATENT DOCUMENTS

| JP | 4627769 B2 | 2/2011 |
| WO | WO-2022221913 A1 | 10/2022 |
| WO | WO-2023101690 A1 | 6/2023 |

OTHER PUBLICATIONS

Uemura, K., et al., "A Minimally-Occlusive Cuff Method Utilizing Ultrasound Vascular Imaging for Stress-Free Blood Pressure Measurement," ESC Congress 2020—The Digital Experience, Aug. 29, 2020-Sep. 1, 2020, National Cerebral & Cardiovascular Center, Suita, Japan, p. 2753.
(Continued)

*Primary Examiner* — Yi-Shan Yang
(74) *Attorney, Agent, or Firm* — Sterne, Kessler, Goldstein & Fox P.L.L.C.

(57) ABSTRACT

A device and system for and methods of using an ultrasound probe housing containing ultrasound probes configured to produce images inside the body of a patient for procedures requiring needle or probe insertion. The ultrasound probe housing can be configured with a guide channel cut-out or aperture between the ambient side and body side of a patient. A needle guide assembly may be pivotally connected internal to the guide channel cut-out or aperture of the ultrasound probe housing at a pivot point such that during use the needle enters the patient through the needle guide assembly within the ultrasonic probe housing so that the needle can be visualized by the ultrasonic probes in real time. The ultra-
(Continued)

sound probe housing may also provide an adhesion or suction quality to the body side of the device to facilitate aspects of the invention.

30 Claims, 41 Drawing Sheets

Related U.S. Application Data

No. 17/410,301, filed on Aug. 24, 2021, now Pat. No. 11,701,082, which is a continuation of application No. 16/445,355, filed on Jun. 19, 2019, now Pat. No. 11,129,588.

(52) U.S. Cl.
CPC ............ *A61B 8/4444* (2013.01); *A61B 8/483* (2013.01); *A61B 8/5253* (2013.01); *A61B 2017/3405* (2013.01)

(56) References Cited

U.S. PATENT DOCUMENTS

| | | | |
|---|---|---|---|
| 11,000,311 | B2 | 5/2021 | Moskowitz et al. |
| 11,129,588 | B2 | 9/2021 | Adams et al. |
| 11,696,738 | B2 | 7/2023 | Adams et al. |
| 11,696,739 | B2 | 7/2023 | Adams et al. |
| 11,701,082 | B2 | 7/2023 | Adams et al. |
| 11,701,083 | B2 | 7/2023 | Adams et al. |
| 11,701,084 | B2 | 7/2023 | Adams et al. |
| 11,701,085 | B2 | 7/2023 | Adams et al. |
| 11,877,888 | B2 | 1/2024 | Adams et al. |
| 12,029,608 | B2 | 7/2024 | Adams et al. |
| 12,097,069 | B2 | 9/2024 | Adams et al. |
| 2003/0179445 | A1 | 9/2003 | Maenle et al. |
| 2006/0241368 | A1 | 10/2006 | Fichtinger et al. |
| 2007/0129686 | A1 | 6/2007 | Daily et al. |
| 2009/0093761 | A1 | 4/2009 | Sliwa et al. |
| 2011/0125022 | A1 | 5/2011 | Lazebnik |
| 2012/0296213 | A1 | 11/2012 | Mauldin, Jr. et al. |
| 2013/0066192 | A1 | 3/2013 | Sarvestani et al. |
| 2013/0102891 | A1 | 4/2013 | Binnekamp et al. |
| 2013/0131501 | A1 | 5/2013 | Blaivas et al. |
| 2013/0178789 | A1 | 7/2013 | Mackool |
| 2013/0245375 | A1 | 9/2013 | DiMaio et al. |
| 2013/0345718 | A1 | 12/2013 | Crawford et al. |
| 2014/0276081 | A1 | 9/2014 | Tegels |
| 2014/0364730 | A1 | 12/2014 | Marteau et al. |
| 2015/0112200 | A1* | 4/2015 | Oberg ................... A61B 8/4455 600/461 |
| 2015/0223774 | A1 | 8/2015 | Ikeda et al. |
| 2016/0008057 | A1 | 1/2016 | Peppou |
| 2016/0022309 | A1 | 1/2016 | Allaway |
| 2016/0038119 | A1 | 2/2016 | Desjardins |
| 2016/0270760 | A1 | 9/2016 | Janicki et al. |
| 2016/0374644 | A1* | 12/2016 | Mauldin, Jr. .......... A61B 8/085 600/424 |
| 2017/0020558 | A1 | 1/2017 | Xu et al. |
| 2018/0000446 | A1 | 1/2018 | Lu et al. |
| 2018/0078240 | A1 | 3/2018 | Pelissier et al. |
| 2018/0161502 | A1 | 6/2018 | Nanan et al. |
| 2019/0059848 | A1* | 2/2019 | Owen ................... A61B 8/4281 |
| 2019/0125470 | A1* | 5/2019 | Moskowitz ........ A61B 17/3403 |
| 2020/0016373 | A1 | 1/2020 | Hulvershorn et al. |
| 2020/0030044 | A1 | 1/2020 | Wang et al. |
| 2020/0155117 | A1* | 5/2020 | Acuna .................. A61B 8/4209 |
| 2020/0187981 | A1* | 6/2020 | Tian ..................... A61B 8/0841 |
| 2020/0261057 | A1 | 8/2020 | Maracaja |
| 2020/0305927 | A1 | 10/2020 | Grim et al. |
| 2020/0397399 | A1 | 12/2020 | Adams et al. |
| 2021/0259660 | A1 | 8/2021 | Bharat et al. |
| 2021/0356437 | A1 | 11/2021 | Skoglund et al. |
| 2021/0378628 | A1 | 12/2021 | Adams et al. |
| 2021/0386397 | A1 | 12/2021 | Adams et al. |
| 2021/0393234 | A1 | 12/2021 | Adams et al. |
| 2022/0000446 | A1 | 1/2022 | Adams et al. |
| 2022/0000565 | A1 | 1/2022 | Gururaj et al. |
| 2022/0008033 | A1 | 1/2022 | Adams et al. |
| 2022/0047240 | A1 | 2/2022 | Adams et al. |
| 2022/0087639 | A1 | 3/2022 | Adams |
| 2023/0090966 | A1 | 3/2023 | Mauldin, Jr. et al. |
| 2023/0181152 | A1 | 6/2023 | Adams et al. |
| 2023/0293141 | A1 | 9/2023 | Adams et al. |
| 2023/0293142 | A1 | 9/2023 | Adams et al. |
| 2024/0074733 | A1 | 3/2024 | Frane et al. |
| 2024/0307023 | A1 | 9/2024 | Adams et al. |
| 2024/0350113 | A1 | 10/2024 | Adams et al. |
| 2024/0366179 | A1 | 11/2024 | Adams et al. |

OTHER PUBLICATIONS

International Search Report and Written Opinion for Application No. PCT/US2024/012122, mailed on Jul. 2, 2024, 12 pages.
International Search Report and Written Opinion for Application No. PCT/US2024/029434, mailed on Aug. 27, 2024, 17 pages.
Jiang, T., et al., "Localization Accuracy of Ultrasound-Actuated Needle with Color Doppler Imaging," Diagnostics 10(12):1020, 14 Pages, MDPI, Switzerland (Nov. 2020).
U.S. Appl. No. 19/007,176, filed Dec. 31, 2024, entitled "Ultrasound Probe With an Integrated Needle Assembly and a Computer Program Product, a Method and a System for Providing a Path for Inserting a Needle of the Ultrasound Probe".

* cited by examiner

ULTRASOUND PROBE WITH AN INTEGRATED NEEDLE ASSEMBLY AND A COMPUTER PROGRAM PRODUCT, A METHOD AND A SYSTEM FOR PROVIDING A PATH FOR INSERTING A NEEDLE OF THE ULTRASOUND PROBE

CROSS-REFERENCE TO RELATED APPLICATIONS

This application is a Divisional of U.S. patent application Ser. No. 17/542,080, filed Dec. 3, 2021, now pending, which is a Continuation-In-Part of U.S. patent application Ser. No. 17/410,301, filed Aug. 24, 2021, now U.S. Pat. No. 11,701,082, which is a continuation of U.S. patent application Ser. No. 16/445,355, filed Jun. 19, 2019, now U.S. Pat. No. 11,129,588. The entirety of each of these applications is incorporated by reference herein.

FIELD OF THE INVENTION

Embodiments of the present invention generally relate to application of ultrasonic waves in medical procedures and more particularly to an ultrasound probe with an integrated needle assembly and a computer program product, a method, and a system for providing a path for inserting a needle of the ultrasound probe.

BACKGROUND ART

Procedures that require needle penetration are some of the most common medical procedures yet remain relatively unchanged since their inception in 1891. In a typical scenario, a practitioner uses palpation of landmarks, such as the iliac crests and the spinous processes, to guide location of a needle during a blind procedure. Examples of such procedures include lumbar puncture (LP), epidural and spinal injections, and spinal nerve blocks. Failure rate of one of the most common medical procedures, lumbar puncture, however, is about 20% owing to the difficulty of identifying landmarks and the inability to visualize the location and trajectory of the needle. This rate is expected to increase as obesity increases in the global population. While ultrasound has been used to aid in the identification of structural landmarks, needle insertion continues to be an obstructed or blind procedure without significant improvement in success rates with using static ultrasound. Failure of a bedside lumbar puncture consequently leads to a fluoroscopic lumbar puncture which results in increased cost, unnecessary inpatient admissions, and delay in patient care. Additionally, pain control and anesthesia has increasingly included local and regional nerve blocks. These procedures can use either landmarks or are limited to two-dimensional (2D) ultrasound, which limits the number of providers choosing this method due to the high initial skill required for a successful procedure. For example, femoral nerve blocks are increasingly being utilized to decrease the need for opiate pain control after hip fractures, which are proven to have improved pain control and decrease adverse events.

Several recent approaches are meant to address the above mentioned problems. But each approach continues to have multiple system or use limitations. For example, certain systems include ultrasound devices with an attached needle. These devices, however, are limited in function at least by the location or attachment of the needle away from the ultrasound transducer itself such that the needle is outside of the field of view provided by the ultrasound transducers. Other devices provide a needle that has restricted movement yielding inadequate procedural flexibility. Additionally, other certain available devices provide inadequate image viewing, such as with 2D imaging, that make needle tracking or visualization more difficult for the medical practitioner. These systems also suffer from the inability to provide a predicted optimum path within the patient for needle travel. Obstructed image viewing of the needle path and inability to predict the path of the needle leads to procedure failure. Overall, there remains an enhanced risk of injuring the anatomical parts of the body such as the tissues, nerves etc. that are located near the target internal body part.

Therefore, a need exists in the art for an ultrasound probe with an integrated needle assembly and a computer program product, a method, and a system for providing a path for inserting a needle of the ultrasound probe which does not suffer from above mentioned deficiencies.

SUMMARY OF THE INVENTION

In accordance with teachings of the present invention a device for providing a path for inserting a needle inside a body of a patient for performing medical procedures is provided.

An object of the present invention is to provide a device having an ultrasound probe housing, a guide channel cut-out or aperture, and a needle guide assembly. The ultrasound probe housing generates ultrasound waves to produce images inside of the body of a patient. The ultrasound probe housing has an ambient side and a body side and can be of any shape meeting the requirements of the invention. The ultrasound probe housing may also provide an adhesion or suction quality to the body side of the device to facilitate aspects of the invention.

The guide channel cut-out or aperture is configured between the ambient side and the body side through the ultrasound probe housing. The needle guide assembly may pivotally connect internal to the guide channel cut-out or aperture on the body side of the ultrasound probe housing at a pivot point. The needle guide assembly receives a needle. A needle is adapted to slide within the needle guide assembly such that during use the needle enters the patient through the needle guide assembly within the ultrasonic probe housing so that the needle can be visualized by the ultrasonic probes in real time.

Another object of the invention is to provide a device with a rotation angle sensor. The rotation angle sensor is configured at or near the pivot point and connected with the needle guide assembly or sufficiently close to the needle guide assembly to approximate the needle angle within the assembly. Further, the rotation angle sensor can be a potentiometer.

Another object of the invention is to provide a device with a rotation angle sensor. The rotation angle sensor is configured at or near the pivot point and connected with the needle guide assembly or sufficiently close to the needle guide assembly to approximate the needle angle within the assembly. Further, the rotation angle sensor can be a potentiometer.

Another object of the invention is to provide a device with a locking mechanism that will hold the angular position of the needle to a fixed position as selected by the operator as to hold the needle in a fixed angular position while the procedure is being conducted.

Another object of the invention is to provide a device with an angle of rotation of the needle guide assembly inside the guide channel cut-out or aperture of the ultrasound probe housing. The guide channel cut-out or aperture may be a slot within the ultrasound probe housing giving an angle of rotation within a range of 0 degrees to roughly 180 degrees, or may be a more complex shape, such as conical shape, to further increase the degree of rotation of the needle guide assembly beyond that of a slotted shape. Further, the needle guide assembly is configured to be actuated by either mechanical unit or electrical unit. A person skilled in the art may appreciate that range of motion of the needle guide assembly may be assisted by the use of movement aids such as a bearing collar.

Another object of the invention is to provide the device with a pressure transducer is configured to be disposed in the needle.

Another object of the invention is to provide a path for inserting a needle into a body of a patient for performing medical procedures involving an ultrasound probe. The method includes steps of receiving images of inside of body of a patient generated corresponding to reflected ultrasonic waves, from an ultrasonic probe housing, generating real-time 3-Dimensional (3D) images of anatomical parts of the body between the ultrasound probe and a target internal body part, displaying the real-time 3D images on a display device connected with the ultrasound probe, optionally comparing the real-time 3D images with pre-stored reference data stored in a data repository, and providing a path for inserting the needle through the ultrasound probe towards the target internal body part. A path or paths may be displayed as a visual overlay on the display device displaying the underlying anatomy and may be generated with the assistance of computer software, for example with the use of artificial intelligence. The path or paths may be based on the available information that is both general (non-patient specific) and/or patient specific. The operator may then accept a path in space within the patient or choose a different path. The system receiving, processing, and providing an output may be a desktop PC, notebook, handheld, or mobile device, such as a smartphone, being linked in a wired or wireless form to the ultrasound probe.

Another object of the invention is to provide the step of guiding the needle on the provided path to the target internal body part through an automated and rotatable needle guide assembly, wherein the needle being covered in the field of view of the ultrasound probe is displayed on the display device during insertion.

Another object of the invention is to provide the step of guiding the needle on the provided path to the target internal body part using a needle insertion handle provided on the needle through the rotatable needle guide assembly, wherein the needle being covered in the field of view of the ultrasound probe is displayed on a display device during insertion, and wherein the needle insertion handle provides enhanced maneuverability for the practitioner/user.

Another object of the present invention is to provide the step of providing one or more of 3D images of the previously performed medical procedures, previously provided paths for similar procedures and images and details of anatomical parts of the body. Such images may be specific to the patient having the procedure performed with the device or method of the invention and may be general in nature.

An object of the present invention is to provide a device having an ultrasound probe housing. The ultrasound probe housing generates ultrasound waves to produce images inside of the body of a patient. The ultrasound probe housing has an ambient side and a body side. The ultrasound probe housing provides an adhesion or suction quality to the body side of the device.

Another object of the device is to allow the ultrasound array and other various device components to be removed, maintained, or replaced for sterility, cleaning, and other maintenance functions.

Yet another object of the present invention is to provide an ultrasound device that can facilitate blood draws, placement, and insertion of an intravenous line (or IV) or catheter into the body of the patient, identification of a physical structure, such as a nerve or joint, or to otherwise inject or aspirate a medium (e.g., a vessel or other anatomical structure) requiring a procedure.

Still another object of the present invention is to provide a supporting structure to which the ultrasound device may be attached, wherein the supporting structure itself may be placed on or affixed to a body of a patient in order to further facilitate performance of a medical procedure, whether the procedure is carried out in an automated fashion or manually by the practitioner.

BRIEF DESCRIPTION OF THE DRAWINGS

So that the manner in which the above recited features of the present invention can be understood in detail, a more particular description of the invention, briefly summarized above, may have been referred by examples, some of which are illustrated in the appended drawings. It is to be noted, however, that the appended drawings illustrate only typical examples of this invention and are therefore not to be considered limiting of its scope, for the invention may admit to other equally effective examples.

These and other features, benefits, and advantages of the present invention will become apparent by reference to the following text figure, with like reference numbers referring to like structures across the views, wherein.

DETAILED DESCRIPTION OF THE EMBODIMENTS

I. Exemplary Embodiments

While various embodiments of the present disclosure are provided herein, it should be understood that they are presented as examples only and are not intended to be limiting. Similarly, the drawings and diagrams depict structural or architectural examples or alternate configurations of the invention, which are provided to aid in understanding the features and functionality of the various embodiments of the invention but are not intended to be limiting. The embodiments and features may be implemented and/or altered in a variety of ways known to those of ordinary skill the art.

Figure 1:
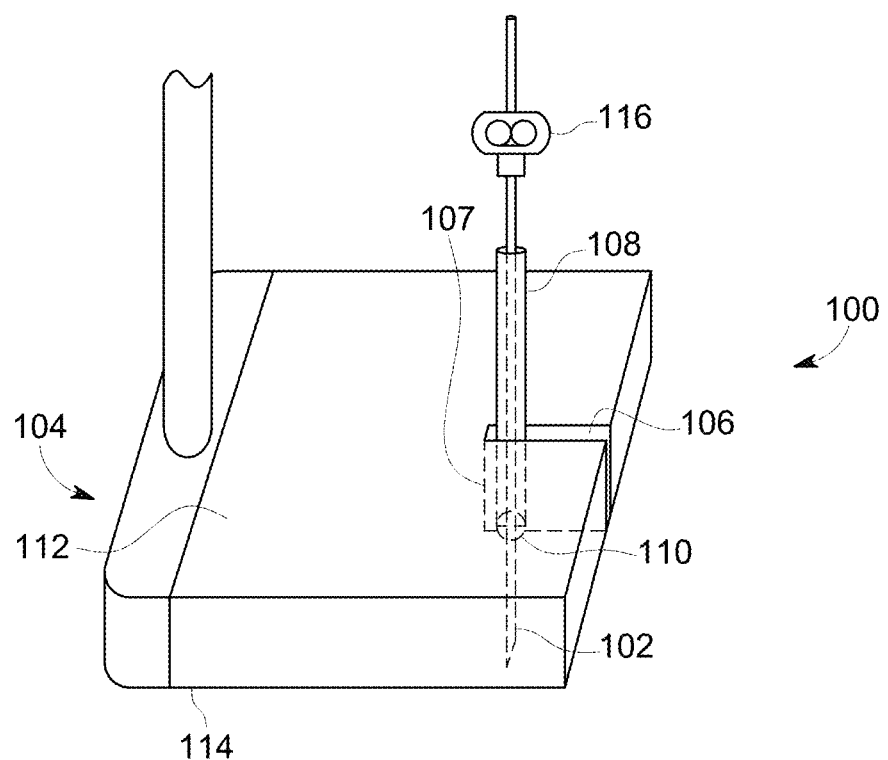
FIG. 1 illustrates a perspective view of a device providing a path for inserting a needle for performing medical procedures, in accordance with an embodiment of the present invention.

FIG. 1 illustrates a perspective view of a device 100 providing a path for inserting a needle 102 for performing medical procedures, in accordance with an embodiment of the present invention. The device 100 includes an ultrasound probe housing 104, a guide channel cut-out or aperture 106, and a needle guide assembly 108. In another embodiment of the present invention, the device 100 further includes a pivot point 110 and rotation angle sensor 111.

The ultrasound probe housing 104 contains a series of probes 105 (not shown) that generate ultrasound waves to produce images of inside of body of a patient. Ultrasound probe housing 104 having an ambient side 112 and a body side 114. Ultrasound probe housing 104 is explained in detail throughout and, for example, in conjunction with FIG. 3 of the present invention.

Guide channel cut-out or aperture 106 is configured between the ambient side 112 and the body side 114 through ultrasound probe housing 104. A needle guide assembly 108 pivotally connects to the guide channel cut-out or aperture 106 on the body side 114 of the ultrasound probe housing 104 at pivot point 110. The needle guide assembly 108 receives a needle 102. Needle 102 is adapted to slide in needle guide assembly 108 such that needle 102 enters the field of view of the ultrasonic probe housing 104 upon insertion into the tissue of the patient receiving the procedure.

In an embodiment of the present invention, pivot point 110 is located near to left side 107 of the guide channel cut-out or aperture 106. However, it would be readily apparent to those skilled in the art to move pivot point 110 in the guide channel cut-out or aperture 106 to increase angle of rotation of needle 102 without deviating from the scope of the present invention.

Needle guide assembly 108 pivotally moves inside the guide channel cut-out or aperture 106 between a vertical setting and a shallow setting. As shown in FIG. 1, needle guide assembly 108 is at vertical setting. However, it would be readily apparent to those skilled in the art that the guide channel cut-out 106 may be created in multiple shapes such as circular, conical, hyperboloid, etc. to increase the angle of rotation to a desired angle without deviating from the scope of the present invention. The angle of rotation of the needle guide assembly 108 is explained by way of example in detail in conjunction with FIGS. 8 and 9 of the present invention.

Further in another embodiment of the present invention, the rotational angle sensor 111 is configured at pivot point 110 and connected with needle guide assembly 108 to measure needle location. The rotational angle sensor 111 is a potentiometer. In another embodiment of the present invention, the angle of rotation of the needle guide assembly 108 inside the guide channel cut-out or aperture 106 is in the range of 0 to 180 degrees.

In another embodiment of the present invention, device 100 further includes a needle insertion handle 116 for allowing practitioner/user 706 to hold and move needle 102 inside needle guide assembly 108. Needle guide assembly 108 is a rigid housing that is manually or automatically adjusted and provides a predetermined and rigid path to allow for precise needle insertion to the target. Needle insertion handle 116 may be a conventional cuboid plastic grip but can be modified for improved control and tactile response required in a procedure. Needle insertion handle 116 may include a plastic (or suitable material) shape such as a wing tip, protrusion, or fingerhold that resides at a distance away from the end of the needle to allow for more control with needle insertion, as shown in FIG. 1. Modifying needle insertion handle 116 may obviate practitioner/user 706 need or desire to handle needle 102 directly during the procedure. Further, needle guide assembly 108 will stabilize needle 102 in the x axis to improve practitioner/user 706 needle usage.

Figure 2:
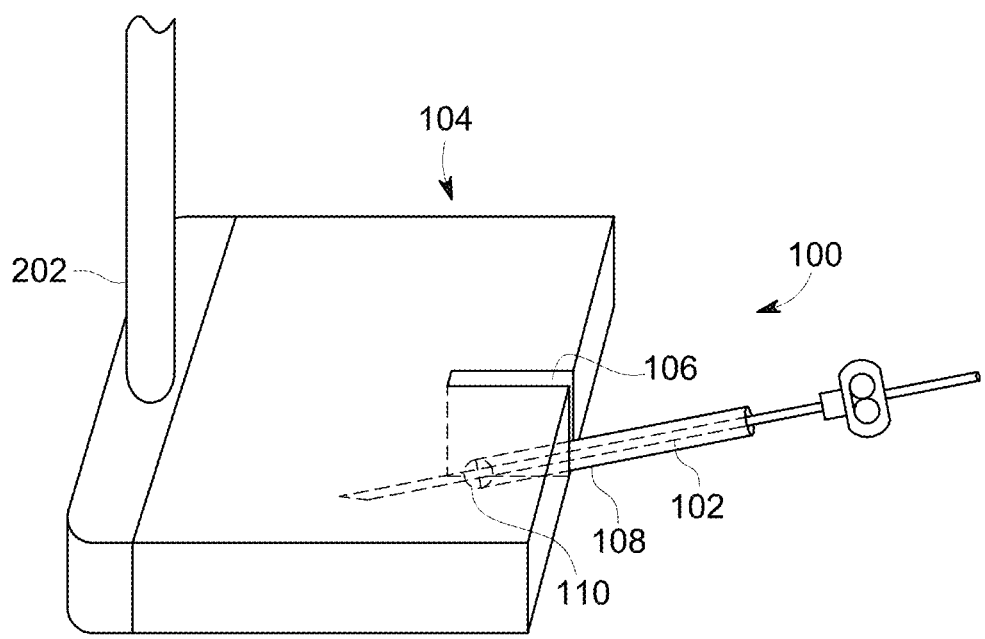
FIG. 2 illustrates another perspective view of a device providing a path for inserting a needle for performing a medical procedure, in accordance with another embodiment of the present invention.

FIG. 2 illustrates another perspective view of the device 100 providing a path for inserting needle 102 for performing medical procedure, in accordance with another embodiment of the present invention. Needle guide assembly 108 is at the shallow setting.

Needle guide assembly 108 is movable by practitioner/user 706 within guide channel cut-out or aperture 106 at any desired angle. Alternatively, needle guide assembly 108 is actuated either by a mechanical unit (such as levers) or an electrical unit (such as robotic arm). In another embodiment of the present invention, device 100 may further include a cord 202 to supply power and transmit data to ultrasound probe housing 104.

In another embodiment of the present invention, guide channel cut-out or aperture 106 is a U shape cut at the edge of the ultrasound probe housing 104. However, it would be readily apparent to those skilled in the art that various shapes (such as V-shaped) and place (such as center) to create the guide channel cut-out or aperture 106 on the ultrasound probe housing 104 may be envisioned without deviating from the scope of the present invention.

Figure 3A:
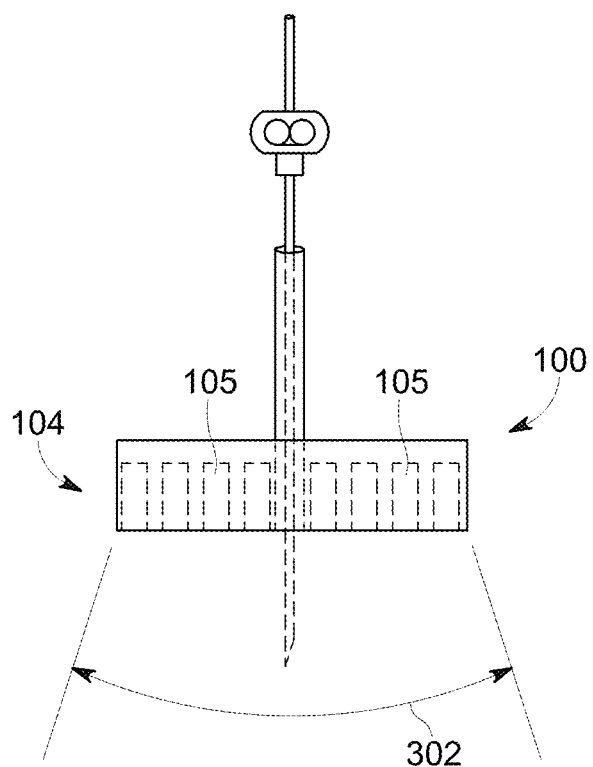
FIG. 3A illustrates a front view of a device in accordance with an embodiment of the present invention.
Figure 3B:
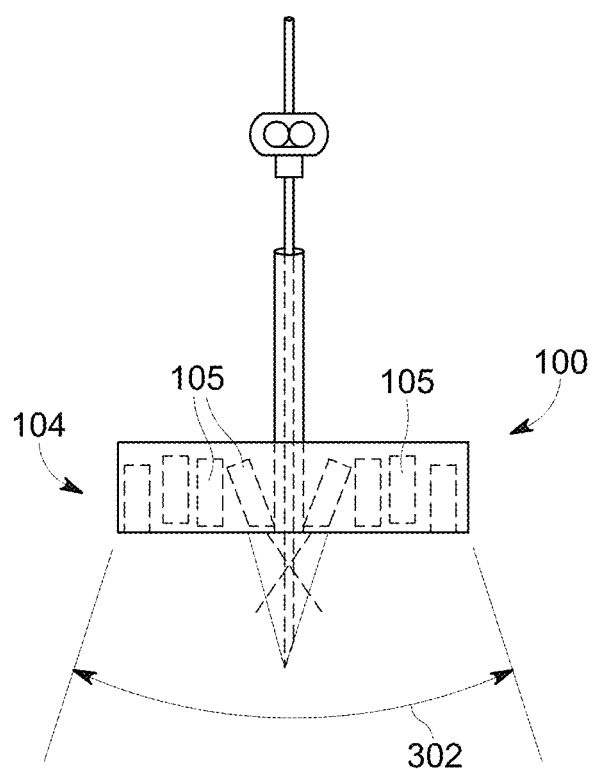
FIG. 3B illustrates a front view of a device in accordance with another embodiment of the present invention.

FIG. 3A illustrates a partial front view of device 100 in accordance with an embodiment of the present invention. Ultrasound probe housing 104 contains probes 105 that generate ultrasonic waves, receive the reflected ultrasonic waves, and generate data in the form of electrical signals corresponding to the received ultrasonic waves.

Ultrasound probe housing 104 generates real-time 3-Dimensional (3D) images of anatomical parts of the body of the patient. A field 302 shows the viewable image area beneath and near the ultrasound probe housing 104. As shown by example in FIG. 3B, the array of probes 105 may be positioned within ultrasound probe housing 104 to alter the viewable image of field 302. In certain formats, probes 105 may be angled within ultrasound probe housing 104 to optimize the viewable image at the site of needle penetration beneath ultrasound probe housing 104. This may be helpful to accommodate changes to the structure of guide channel cut-out or aperture 106. Likewise, probes 105 may be positioned perpendicular to body side 114 of ultrasound probe housing 104 to give a wider viewable image area. Ultrasound probe housing 104 may also contain a mixed array of angled and perpendicular probes 105 to alter viewable image geometries. It would be readily apparent to those skilled in the art that various types and shapes of ultrasound probe housing 104 containing probes 105 may be envisioned without deviating from the scope of the present invention.

Figure 4A:
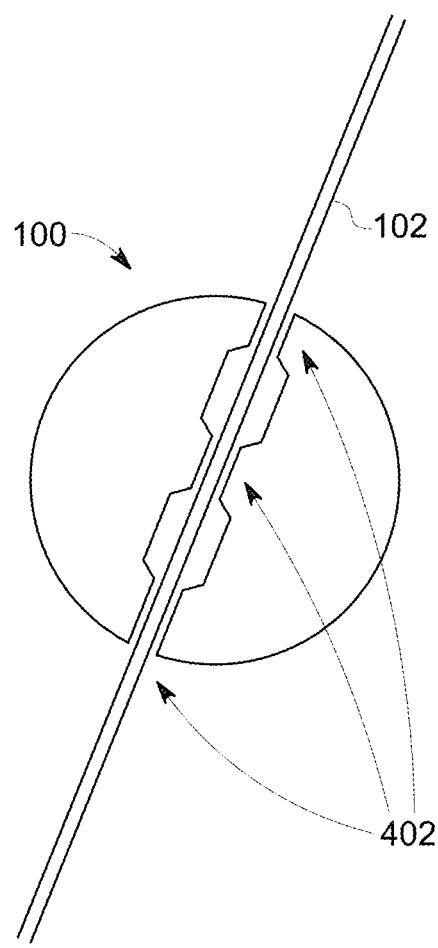
FIG. 4A illustrates a perspective view of a needle guide assembly in accordance with an embodiment of the present invention.

FIG. 4A illustrates a perspective view of needle 102 in accordance with an embodiment of the present invention. In another embodiment of the present invention, device 100 further includes plurality of guide bearings 402 to facilitate sliding motion of needle 102 in needle guide assembly 108 (as shown by example in FIG. 1 to FIG. 3). Needle guide assembly 108 stabilizes needle 102 during insertion into the patient body and attaches needle 102 to ultrasound probe housing 104.

Figure 4B:
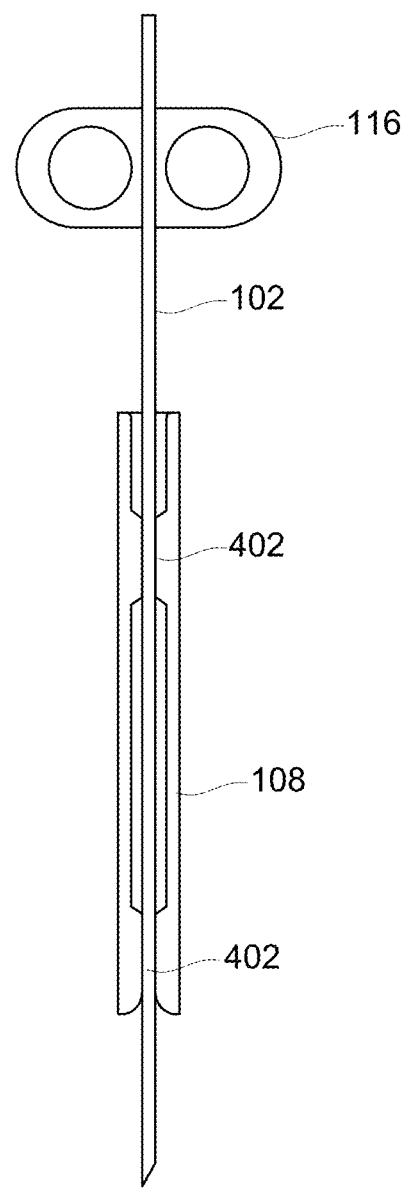
FIG. 4B provides another perspective view of needle in accordance with an embodiment of the invention.

FIG. 4B provides another perspective view of needle 102 in accordance with an embodiment of the invention. FIG. 4A further includes exemplary needle insertion handle 116. It will be appreciated that examples of guide bearings 402 include but are not limited to 1 or more sliding bearings designed to allow needle 102 to move in the radial direction, restricts the needle from bending on insertion, and maintains the needle position in space.

Figure 5:
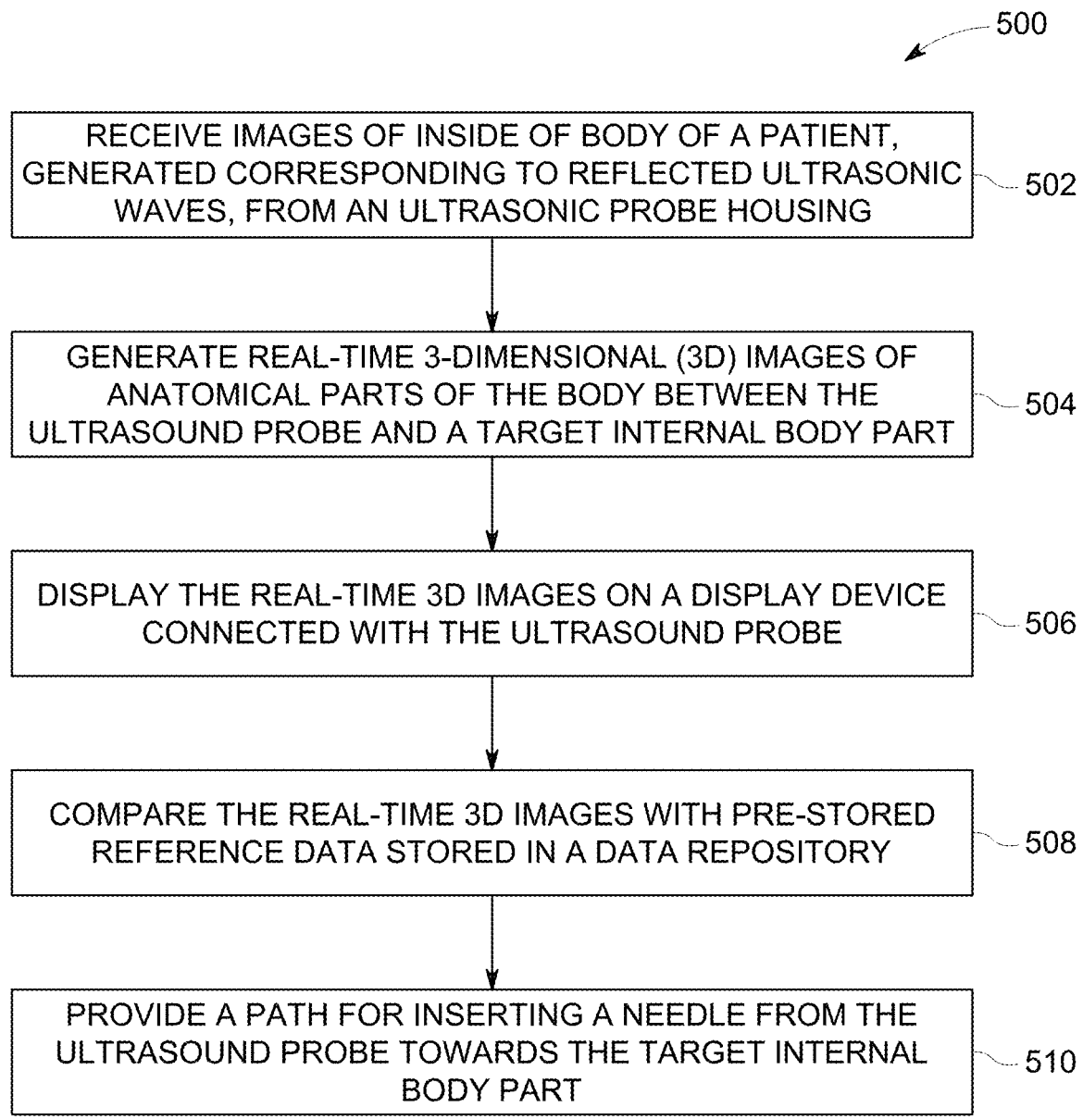
FIG. 5 illustrates a method for providing a path for inserting a needle of the ultrasound probe inside a body of a patient, in accordance with an embodiment of the present invention.

FIG. 5 illustrates a method 500 for providing a path for inserting inside a body of a patient during medical procedures involving an ultrasound probe housing in accordance with an embodiment of the present invention. The method 500 initiates with a step 502 of receiving images of inside of body of a patient, generated corresponding to reflected ultrasonic waves from probes 105 of ultrasonic probe housing 104. Ultrasonic probe housing 104 of step 502 is explained in detail in conjunction with FIG. 1 and FIG. 3 of the present invention.

Step 502 is followed by a step 504 of generating real-time 3-Dimensional (3D) images of anatomical parts of the body between the ultrasound probe and an internal target body location. Data from ultrasound probe housing 104 is transmitted to a processor. The processor processes received data and generates 3D images of anatomical parts in real-time.

Step 504 is followed by a step 506 of displaying the real-time 3D images on a display device receiving information from device 100. The processor processes the data received from the ultrasound probes and the display device displays the processed data. The display device may also display a predicted path 705 of needle 102 based on the current body location of device 100 and current needle angular position. Predicted path 705 represents the path that needle 102 would take through the patient anatomy if needle were extended in space from and based on its current coordinates. The display device and the processor is explained herein and also in further conjunction with FIG. 6 of the present invention.

Figure 6:
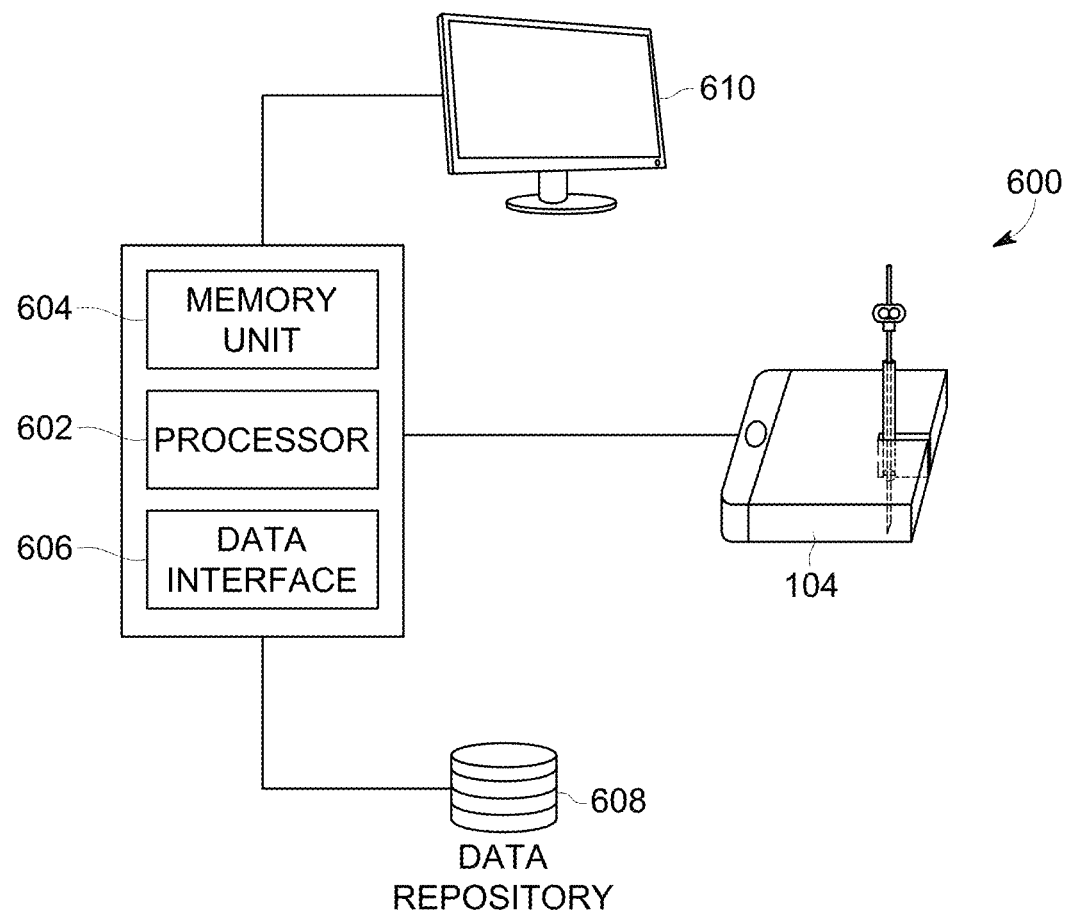
FIG. 6 illustrates a system for providing a path for inserting a needle for medical procedures, in accordance with an embodiment of the present invention.

Step 506 may optionally be followed by a step 508 of comparing the real time 3D images and data with reference data stored in a data repository 608 (as shown by example in FIG. 6). Data repository 608 may also be at a remote location but accessible in real time, such as with cloud storage. Further, step 506 or 508 may then be followed by step 510 of providing a recommended path 707 for inserting needle 102 through the ultrasound probe housing towards the internal target body location. Recommended path 707 is a path through the anatomy of the patient based on available data that may include current real time data from device 100, stored data, and the type of procedure to be performed. The recommended path 707 for inserting needle 102 through the ultrasound probe is displayed on the display device. Both the distance and angle of the device from its current position to the position matching that of the recommended path can be displayed to enable practitioner/user 706 to relocate the device on the patient body to be able to match the recommended path. Predicted path 705 and recommended path 707 may differ from each other. Practitioner/user 706 has the option to use the recommended path 707 or to select an alternate path based on the real time 3D image display and predicted path 705.

Examples of the pre-stored data include but not limited to one or more 2D and 3D images of the previously performed medical procedures that can be patient-specific, previously provided paths for similar procedures, and images and details of anatomical parts of the body, etc.

In an exemplary embodiment of the present invention, the 3D image shows a kidney of a patient in real time, then the processor compares the real time 3D image with the pre-stored data. The pre-stored data showcase the path for inserting needle 102 that corresponds to the image of the kidney. The desired path to perform the medical procedure is displayed on the display device depending upon the real time image.

It would be readily apparent to those skilled in the art that artificial intelligence may be involved at various stages of information usage for the device. For example, AI may assess the path of treating the internal target body location from the data repository 608 (shown in FIG. 6) and may identify a recommended path 707 (shown in FIG. 7) on receiving the similar situation without deviating from the scope of the present invention.

FIG. 6 illustrates a system 600 for providing a path or paths for inserting needle 102 for medical procedures, in accordance with an embodiment of the present invention. The system 600 further includes an ultrasound probe housing 104, a guide channel cut-out or aperture 106, needle guide assembly 108, a processor 602, a memory unit 604, a data interface 606, a data repository 608 and a display unit 610.

The ultrasound probe housing 104, the guide channel cut-out or aperture 106 and needle guide assembly 108 are explained in detail in conjunction with exemplary FIG. 1 to FIG. 3 of the present invention. Processor 602 is connected with the ultrasound probe housing 104 through the data interface 606, which may or may not be a physical, wired connection. For instance, data interface 606 may receive data from a wireless, cellular, or Bluetooth connection.

The data interface 606 receives data from the ultrasound probe housing 104 and transfers the received data to the processor 602 for processing. Examples of the processor 602 can include any system that processes images to predict and map the real patient's anatomy during the live procedure based on changes in echogenicity during the ultrasound. This can include the use of AI or other simulated intelligent programs.

The memory unit 604, the display unit 610 and the data repository 608 are connected with the processor 602 and may each be stand-alone equipment or could be a composite device, such as a desktop PC, notebook, handheld, or mobile device, such as a smartphone. The memory unit 604 stores the instructions, the processor 602 processes the stored instructions and the display unit 610 displays the processed instructions. The instructions are explained in the conjunction with FIG. 5 (method 500) of the present invention.

Examples of the memory unit 604 include but not limited to a fixed memory unit or a portable memory unit that can be inserted into the device. It will be appreciated that memory unit 604 would have sufficient memory to adequately store large volumes of information. It is expected that each system may offer advantages in certain use situations. For example, a portable memory unit may also be insertable into and compatible with an available medical record system for information exchange. A fixed memory unit may achieve a similar goal by having a port for information exchange. Examples of the display unit 610 include but not limited to LCD, LED, OLED, TFT, or any specific display of any unit device capable of visually providing information such as on a desktop PC, notebook, handheld, or mobile device, such as a smartphone.

Figure 7:
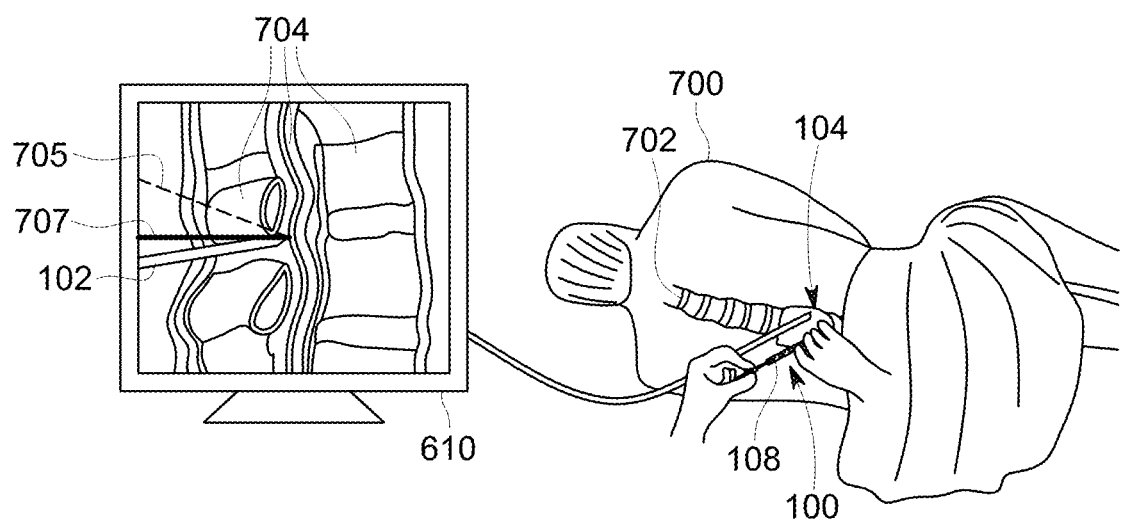
FIG. 7 illustrates a schematic diagram of performing medical procedures on the patient using a device in which a pathway for needle insertion into the patient is provided, in accordance with an embodiment of the present invention.

FIG. 7 illustrates a schematic diagram of performing medical procedure on the patient 700 using the device 100, in accordance with an embodiment of the present invention. In this example, ultrasound probe housing 104 is placed on the back of the patient 700 to perform a medical procedure on spine 702.

The ultrasound probe housing 104 captures images of spine 702 and other anatomical body parts 704 of patient 700 and displays the images on the display device 610 in real time. The display of spine 702 and anatomical body parts 704 allows a practitioner/user 706 to move needle 102, which is placed inside needle guide assembly 108, through the guide channel cut-out or aperture 106 to perform the required medical procedure on the desired location of the body part of the patient 700.

Device 100 allows practitioner/user 706 to perform the medical procedure with greater ease and on the desired location. Due to its location within and through ultrasound probe housing 104, the visibility of needle 102 in 3D allows practitioner/user 706 viewing of the desired location from multiple angles for improved procedural accuracy.

Further, FIG. 7 illustrates use of device 100 where the pathway for insertion of needle 102 through ultrasound probe housing 104 is predicted and displayed on display unit 610 based on information collected in real time and/or from data repository 608 of system 600. The control unit will take the angular position input from the potentiometer and automatically adjust the optimum angle of needle 102 via a motor to pass between anatomical structures, for example, spinous processes, for procedural success. The angle of needle 102 may also be manually managed by a movement mechanism such as a turning dial to set a final needle path. Practitioner/user 706 can choose to follow predicted path 705 for needle 102, recommended path 707 for needle 102, or some other path of the operator's choosing. Once practitioner/user 706 selects an insertion pathway, needle guide assembly 108 is locked in position to allow needle 102 to be inserted along the selected path. Depending on the embodiment of the device, practitioner/user 706 would also be able to stabilize the device location relative to the patient body by actuating attachment features of device 100 discussed herein. The insertion of needle 102 can be manually or automatically driven by or through device 100. It will be appreciated that system 600 will use computer processing in determining and displaying predicted path 705 and recommended path 707, and such processing may be based on artificial intelligence. In another embodiment of the invention, the display device may further display anticipated procedural steps to be performed for the specific procedure being undertaken by practitioner/user 706. Upcoming procedure steps may be indicated as textual prompts, bubble callouts, audibles, and may also include voice commands or prompts.

Figure 8A:
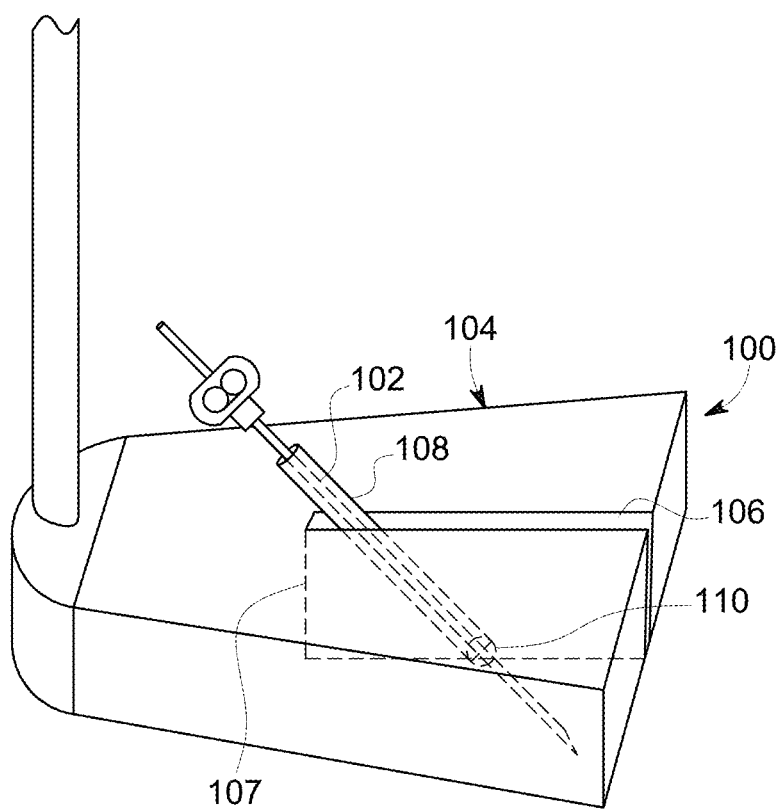
FIG. 8A illustrates a perspective view of the device providing a path for inserting a needle for performing a medical procedure, in accordance with an embodiment of the present invention.
Figure 8B:
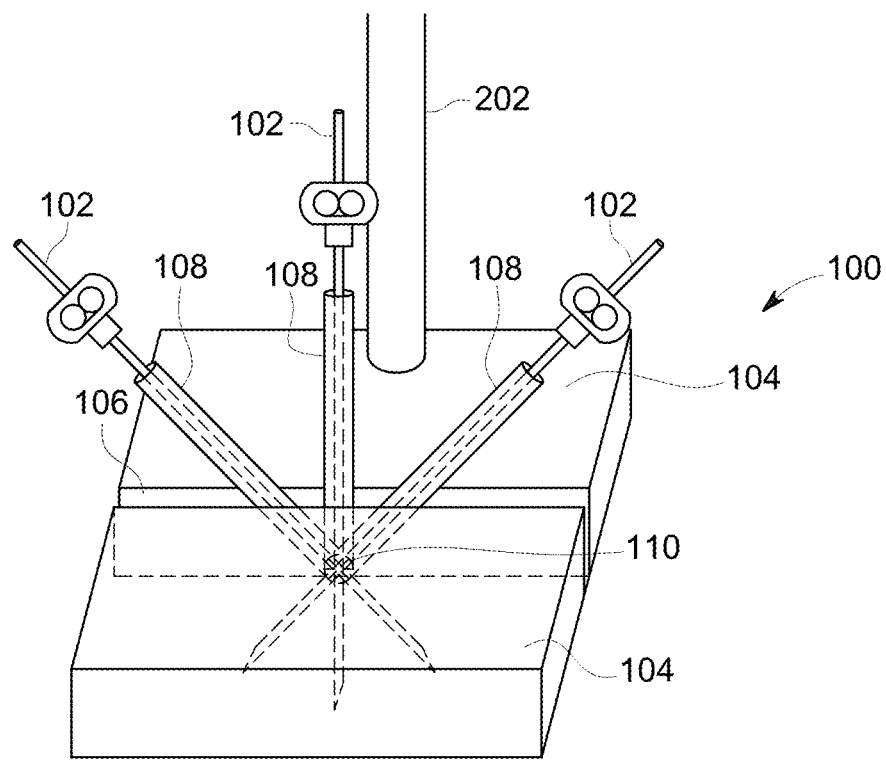
FIG. 8B illustrates a perspective view of the device providing a path for inserting a needle for performing a medical procedure, in accordance with another embodiment of the present invention.
Figure 9A:
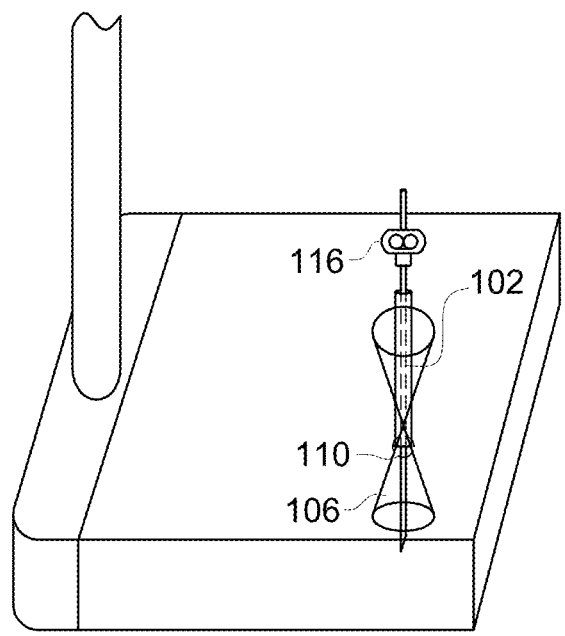
FIG. 9A illustrates a perspective view of the device providing a path for inserting a needle for performing medical procedure, in accordance with another embodiment of the present invention.
Figure 9B:
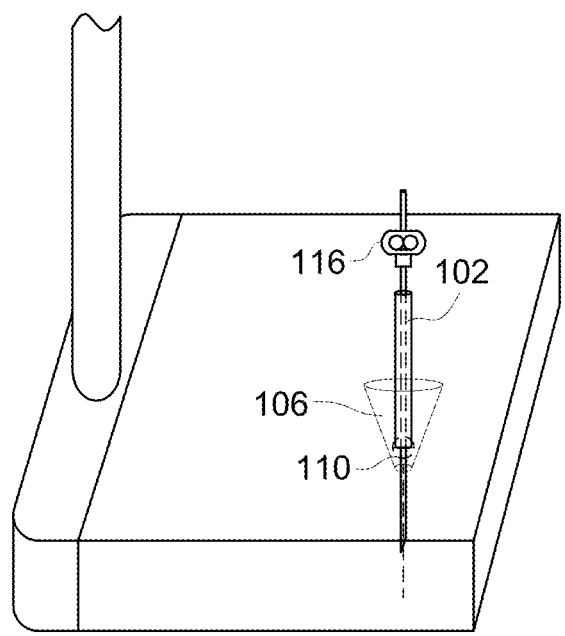
FIG. 9B illustrates a perspective view of the device providing a path for inserting a needle for performing medical procedure, in accordance with another embodiment of the present invention.
Figure 9C:
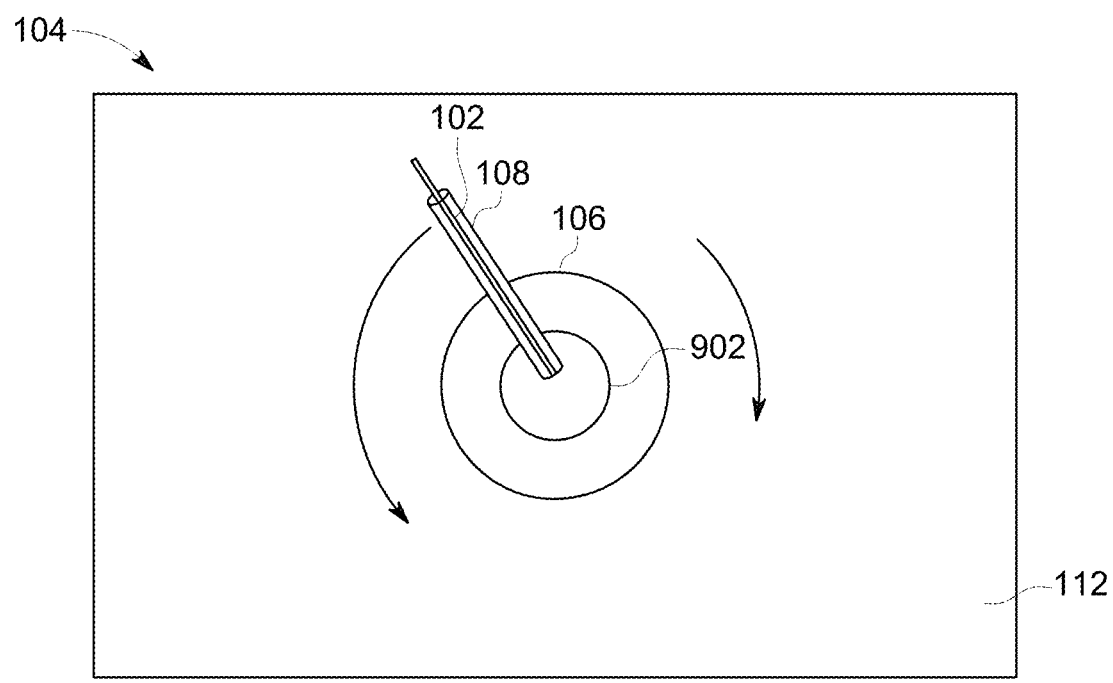
FIG. 9C illustrates a top view of the device providing a path for inserting a needle for performing medical procedure, in accordance with another embodiment of the present invention.
Figure 9D:
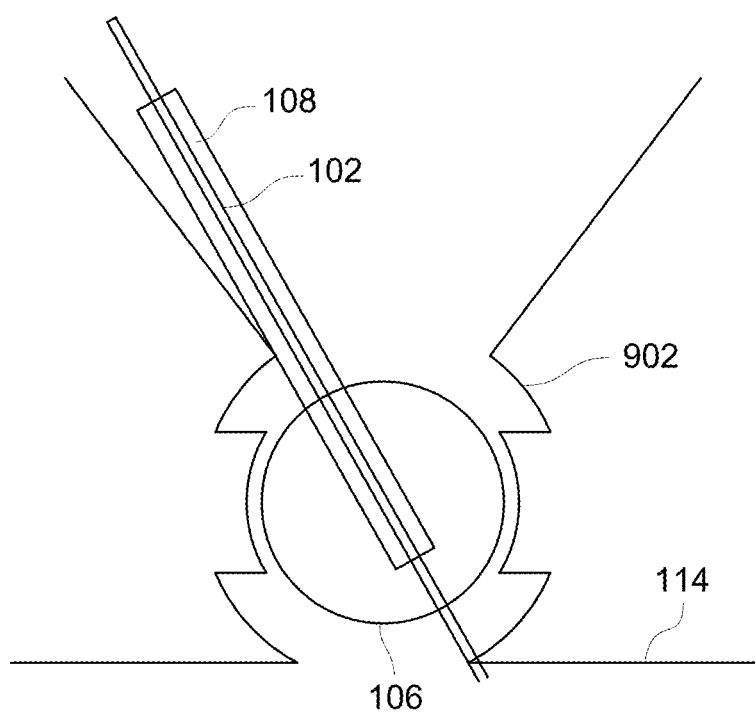
FIG. 9D illustrates a side view cutaway of the device providing a path for inserting a needle for performing medical procedure, in accordance with another embodiment of the present invention.

FIG. 8A illustrates another perspective view of the device 100 providing a path for inserting a needle 102 for performing the medical procedure, in accordance with another embodiment of the present invention. The length of the guide channel cut-out or aperture 106 is extended to allow needle guide assembly 108 to rotate in both directions within the channel-like structure, i.e., up to 180 degrees of total range of movement. Pivot point 110 is now away from the left side 107 of the guide channel cut-out or aperture 106. The needle guide assembly 108 passes through pivot point 110 and thus the angle of rotation increases from approximately 0 to 90 degrees to a fuller range of 0 to 90 degrees and 0 to minus 90 degrees. FIG. 8B provides another example where guide channel cut-out or aperture 106 provides a greater range of motion over device 100 as depicted in exemplary FIG. 1. In this embodiment, it will be appreciated that guide channel cut-out or aperture 106 has rotated from the direction provided in FIG. 8A. It will further be appreciated that the location of guide channel cut-out or aperture 106 is not fixed so long as needle 102 exits through body side 114 of ultrasound probe housing 104 of device 100 to achieve the purposes of the invention.

FIGS. 9 illustrates various views of device 100 for providing a path for inserting needle 102 for performing a medical procedure with guide channel cut-out or aperture 106 having cone-like geometries. Needle guide assembly 108 pivotally connects to the guide channel cut-out or aperture 106 on or near the body side 114 of the ultrasound probe housing 104 at pivot point 110. In these configurations, needle guide assembly 108 and guide channel cut-out or aperture 106 may use a spherical bearing or similar device that allows needle 102 to rotate both radially and circumferentially, as shown in FIG. 9C and 9D. Needle 102 is adapted to slide in needle guide assembly 108 such that the needle 102 is in a field of view of the ultrasonic probe housing 104 upon insertion into the tissue of the patient receiving the procedure. It will be appreciated that guide channel cut-out or aperture 106 may be a cone or hyperboloid shape, for example as shown as in FIGS. 9A and 9B, to potentially provide greater degrees of movement over the guide channel cut-out or aperture 106 as depicture in FIG. 1. It would be readily apparent to those skilled in the art that various shapes and sizes of guide channel cut-out or aperture 106 may be envisioned without deviating from the scope of the present invention.

Figure 10A:
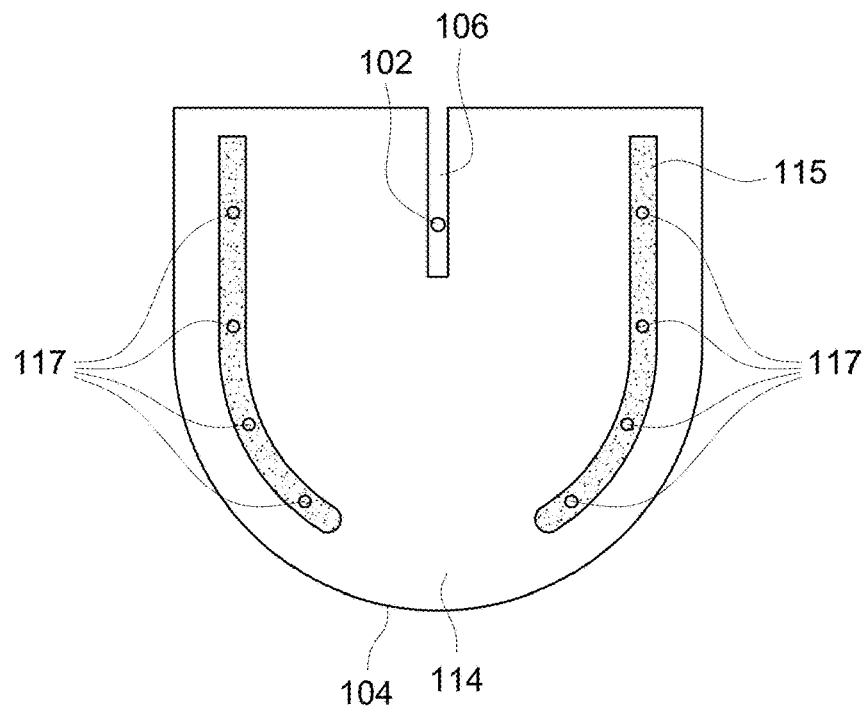
FIG. 10A illustrates a bottom view of the ultrasound probe housing having adhesion points located at the perimeter of the body side of the device in accordance with another embodiment of the present invention.

FIG. 10A illustrates a bottom view of ultrasound probe housing 104 of device 100 having adhesion points 115 located on body side 114 of ultrasound probe housing 104. Adhesion points 115, which may further contain holes 117, fix or adhere ultrasound probe housing 104 in location on the patient to maintain further control of the device for needle penetration. FIG. 10A depicts adhesion points 115 along the perimeter of ultrasound probe housing 104, but it will be appreciated that adhesion points 115 may be located anywhere across body side 114 of ultrasound probe housing 104 so long as they do not interfere with the ability of probes 105 to generate the viewable image field required for the procedure to be performed. FIG. 10A provides adhesion points 115 in the shape of elongated depressions, but adhesion points 115 may be any shape, such as channels, cups, cups with lips or pronounced outer edges, or may have no additional contouring different from body side 114 of ultrasound probe housing 104. It will be appreciated that ultrasound probe housing 104 may be held in place during the procedure by applying suction or tactile adhesion. Holes 117 may provide suction forces to adhesion points 115 in one format and may be a source of skin adhesive to adhere ultrasound probe housing 104 in place in another format.

Figure 10B:
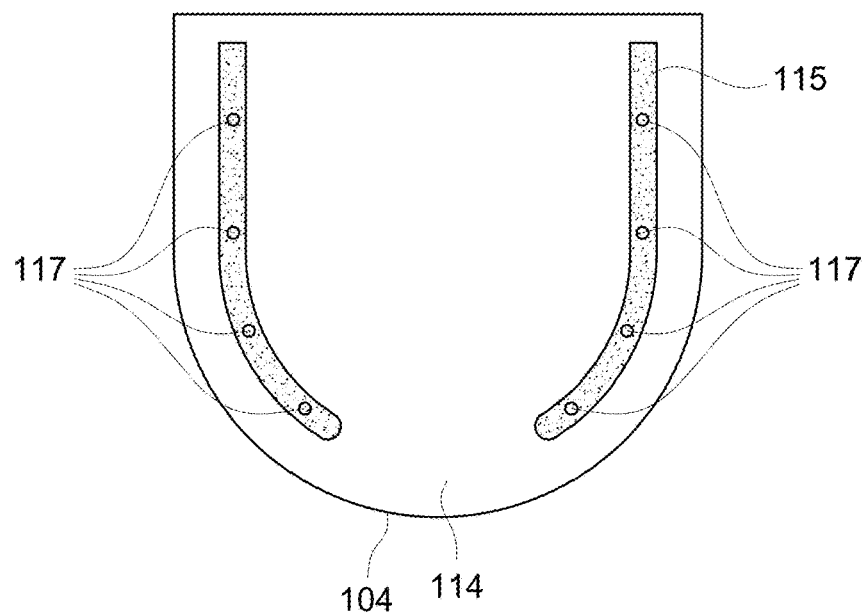
FIG. 10B illustrates a bottom view of the ultrasound probe housing having adhesion points located at the perimeter of the body side of the device in accordance with another embodiment of the present invention.

FIG. 10B provides a bottom of ultrasound probe housing 104 with no guide channel cut-out or aperture 106. This embodiment provides the fixing ability of ultrasound probe housing 104 as described herein with the ability to have needle 102 attached to the ultrasound probe housing 104 in an external manner, or to have needle 102 unattached completely per practitioner/user 706 preference. It will be appreciated that each of the devices disclosed having adhesion points 115 may be without guide channel cut-out or aperture 106 and still provide the ability to fix the device to the patient as desired.

Figure 11A:
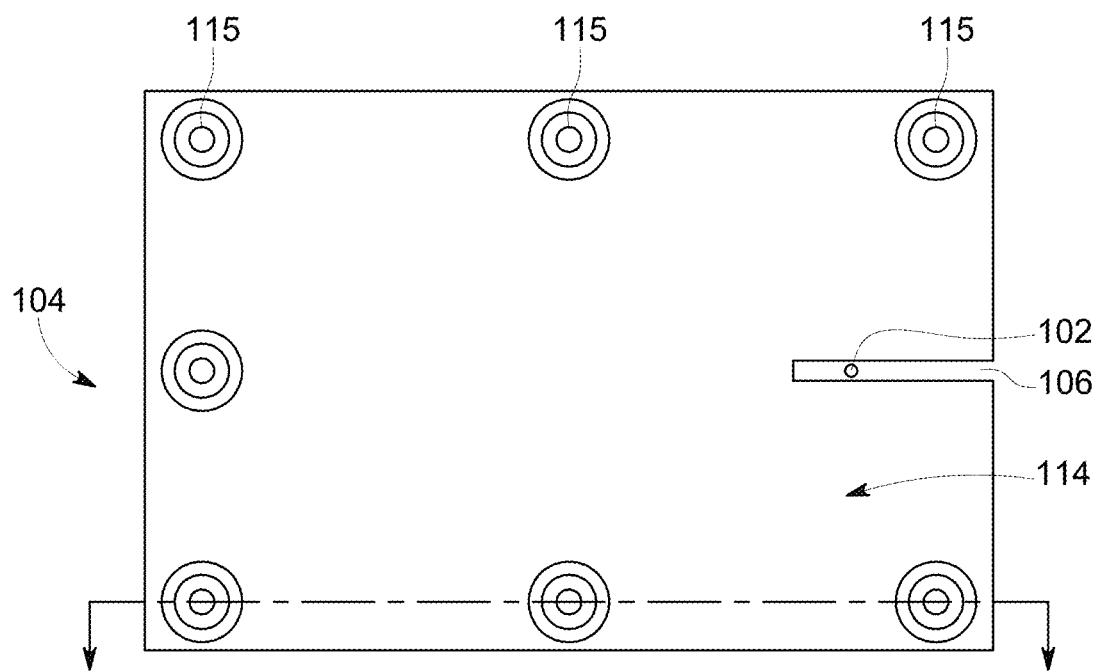
FIG. 11A illustrates a bottom view of the ultrasound probe housing having adhesion points located at the perimeter of the body side of the device in accordance with another embodiment of the present invention.
Figure 11B:
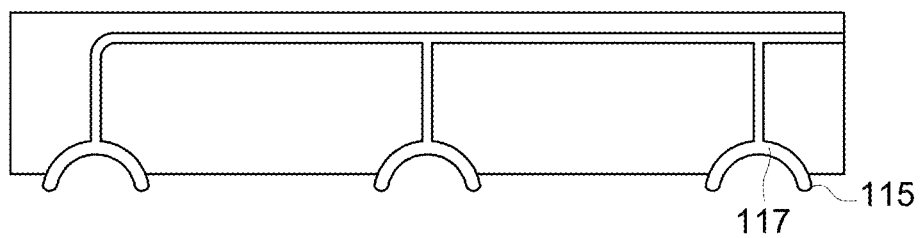
FIG. 11B provides a side cutaway view of the ultrasound probe housing having adhesion points located at the perimeter of the body side of the device in accordance with another embodiment of the present invention.

FIG. 11A demonstrates a bottom view of ultrasound probe housing 104 having adhesion points 115 located at the perimeter of the body side 114 of device 100 (shown in FIG. 1) in accordance with an embodiment of the present invention. FIG. 11B provides adhesion points 115 shaped as depressions with structure along the perimeter of said depressions to facilitate suction contact, e.g., suction cups. Adhesion points 115 further contain holes 117 through which suction forces may be applied to the contact point on the patient body. Ultrasound probe housing 104 contains internal structure such as tubing or channels for air exchange to create suction through holes 117. It will be appreciated that the exact architecture needed to facilitate suction forces can vary so long as it does not interfere with the purposes of this invention.

FIG. 11B provides a side cutaway view of ultrasound probe housing 104 in which adhesion points 115 and holes 117 are apparent and opened to body side 114. It will be appreciated that holes 117 and the corresponding architecture within ultrasound probe housing 104 may provide a source of adhesive instead of suction forces by which to fix device 100.

Figure 12A:
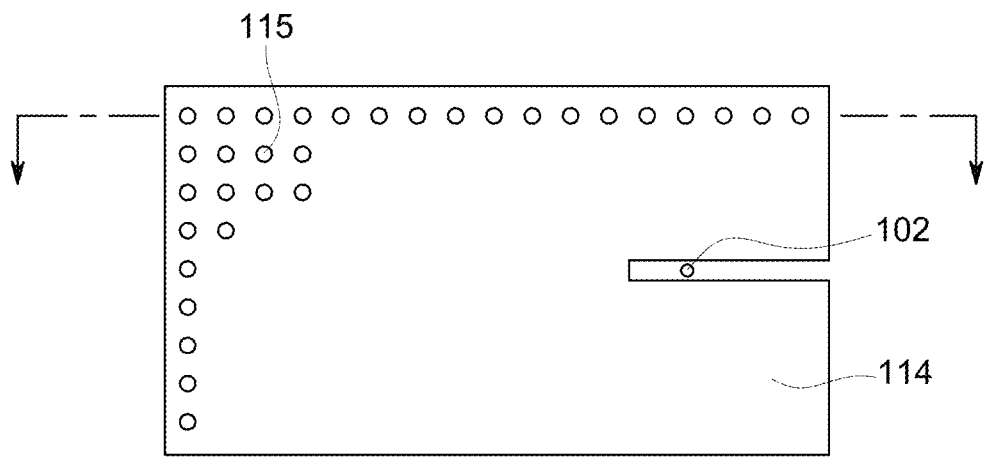
FIG. 12A illustrates a bottom view of the ultrasound probe housing having adhesion points located across the body side of the device in accordance with another embodiment of the present invention.
Figure 12B:
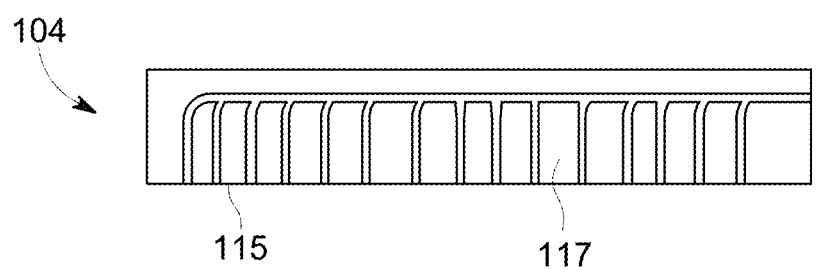
FIG. 12B illustrates a side cutaway view of ultrasound probe housing in which adhesion points and holes are apparent and opened to body side of the device in accordance with another embodiment of the present invention.

FIG. 12A illustrates a bottom view of the ultrasound probe housing 104 having adhesion points 115 located across body side 114 of device 100 in accordance with another embodiment of the present invention. Adhesion points 115 are also holes 117 in this configuration and have no additional contouring on body side 114 of device 100. FIG. 12B provides a side cutaway view of ultrasound probe housing 104 in which adhesion points 115 and holes 117 are apparent and opened to body side 114. It will be appreciated that holes 117 and the corresponding architecture within ultrasound probe housing 104 may provide a source of adhesive instead of suction forces by which to fix device 100. FIG. 12B provides a side view cutaway for illustrate the exemplary architecture of ultrasound probe housing 104.

Figure 13A:
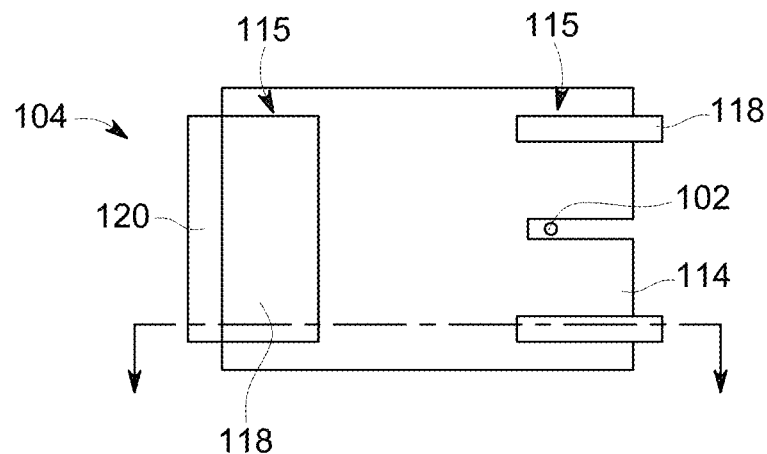
FIG. 13A illustrates a perspective view of the ultrasound probe housing having adhesion points located across the body side of the device in accordance with another embodiment of the present invention.
Figure 13B:
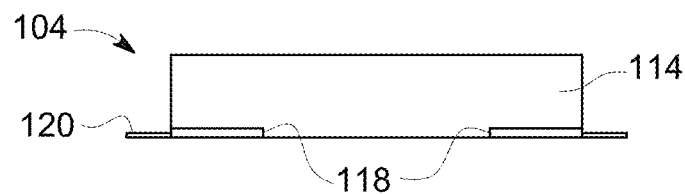
FIG. 13B illustrates a side view of ultrasound probe housing in which adhesion points and adhesive pads are apparent on body side of the device in accordance with another embodiment of the present invention.

FIG. 13A illustrates a bottom view of ultrasound probe housing 104 having adhesion points 115 located on body side 114 of device 100 in accordance with an embodiment of the present invention, where adhesion points 115 are ready for use adhesive pads or films 118. Adhesion points 115 may further contain a protective cover over adhesive pads or films 118 for storage that can be removed at time of use during the surgical procedure. It will be appreciated that body side 114 may be a receptacle for replaceable adhesive pads or films 118 that may be disposed of after each procedure. Such disposable adhesive pads or films 118 may be sterile. Ultrasound probe housing 104 may contain a removable cover 120 that coupleably joins all or a portion of body side 114. Removable cover 120 may itself provide adhesive pads or films 118 or the surface for adhesive pads or films 118 that can be fitted to body side 114 of device 100 for ease of use. Each removable cover 120 may be sterile and individually provided to ultrasound probe housing 104 for the specific procedure. FIG. 13B provides a side view of ultrasound probe housing 104 in which adhesion points 115 and adhesive pads or films 118 are apparent on body side 114.

In accordance with further embodiments that will now be described, a system is provided that comprises an ultrasound device and an associated supporting structure to which the ultrasound device may be attached to facilitate placement and insertion of an intravenous line (or IV) or catheter into the body of the patient, identification of a physical structure, such as nerve or joint, or to otherwise inject or aspirate a medium (e.g., a vessel or other anatomical structure) requiring a procedure.

Figure 14:
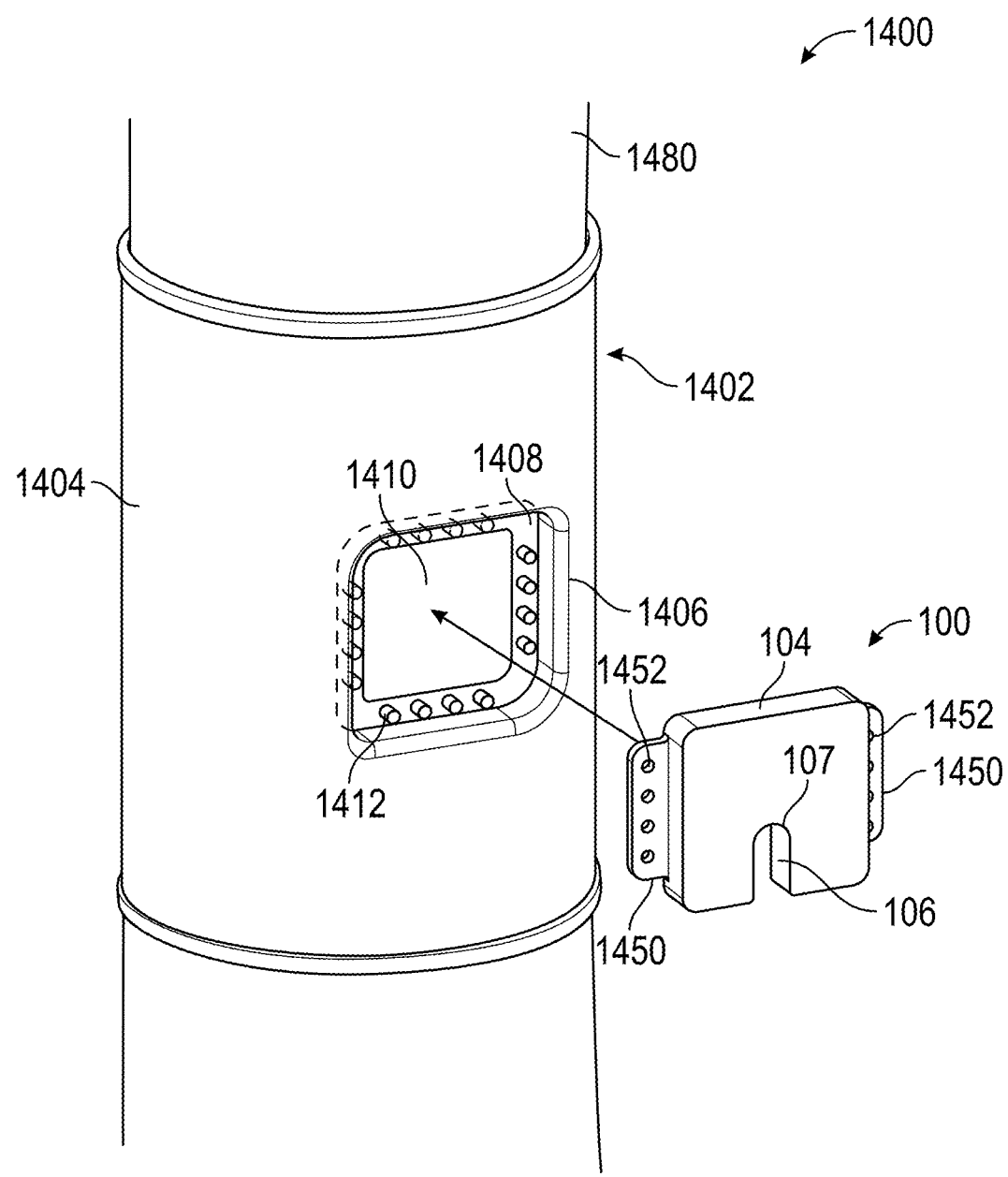
FIG. 14 illustrates a perspective view of a system comprising an ultrasound device providing a path for inserting a needle for performing medical procedures and a supporting structure to which the ultrasound device may be attached, wherein the supporting structure is attached to a patient, in accordance with an embodiment.

For example, FIG. 14 illustrates a perspective view of a system 1400 comprising device 100 for guided insertion of a needle into a body of a patient (also referred to herein as ultrasound device 100) and a supporting structure 1402 to which ultrasound device 100 may be attached for an intended application, such as blood draws. In FIG. 14, supporting structure 1402 is attached to an extremity 1480 (e.g., an arm) of a patient. Ultrasound device 100 detects and projects an image of a vessel, nerve, vascular structure, joint, tissue, organ, or other necessary physical structure of the body of the patient to further a procedure. Ultrasound device 100 is adapted to be connected to supporting structure 1402. In particular, as shown in FIG. 14, ultrasound device 100 comprises ultrasound probe housing 104 having rigid or semi-rigid tabs 1450 extending from two sides thereof, wherein each tab 1450 comprises female mating elements 1452 (e.g., holes) that are adapted to mate with corresponding male mating elements 1412 (e.g., studs or pegs) of supporting structure 1402, thereby facilitating a connection between ultrasound device 100 and supporting structure 1402. The number of female and male mating elements 1452 and 1412, respectively, can vary and need only be numerously sufficient to firmly affix ultrasound device 100 to supporting structure 1402 to perform the desired procedure.

In the embodiment of FIG. 14, supporting structure 1402 comprises a sleeve or cuff that is suitable for attachment to extremity 1480 (e.g., an arm) of the patient, although other devices suitable for attachment to a patient extremity may be used. Supporting structure 1402 may be configured to fit on or around extremity 1480, or other anatomic structure, and can be of varying length, width, and circumference to accommodate the need of the patient anatomy. Depending upon the implementation, supporting structure 1402 may be a unitary structure that slides over the extremity, but may also be placed around or on the anatomy and then secured by attachments such as clamps, clips, tabs, snaps, ties, zippers, Velcro, adhesives, or the like, following placement. For some procedures to be performed, supporting structure 1402 may also be manually held in place by a user.

As further shown in FIG. 14, supporting structure 1402 comprises an ambient side 1404 having an outer surface within which is formed a recess 1406. Supporting structure 1402 also comprises a body side that is opposite ambient side 1404 and faces toward the body of the patient during use. Recess 1406 is adapted to accommodate insertion of at least a portion of ultrasound device 100 and itself comprises a rigid or semi-rigid recessed frame 1408 that surrounds an opening 1410 that passes fully through supporting structure 1402. Recessed frame 1408 comprises four sides, each of which supports a number of outward-facing male mating elements 1412 that are adapted to mate with corresponding female mating elements 1452 of ultrasound device 100.

By selectively aligning female mating elements 1452 of tabs 1450 of ultrasound device 100 with male mating elements 1412 of any two opposing sides of recessed frame 1408 and then at least partially inserting ultrasound device 100 into recess 1406, those mating elements can be caused to engage and ultrasound device 100 will become connected to supporting structure 1402. It should be appreciated that if mating elements 1452 and 1412 are compatible across each of tabs 1450 and each of the sides of recessed frame 1408, then ultrasound device 100 may be rotated relative to guide channel cut-out or aperture 106 to provide access for needle 102 within needle guide assembly 108 or separately to a desired target site of the patient without repositioning supporting structure 1402.

Figure 15:
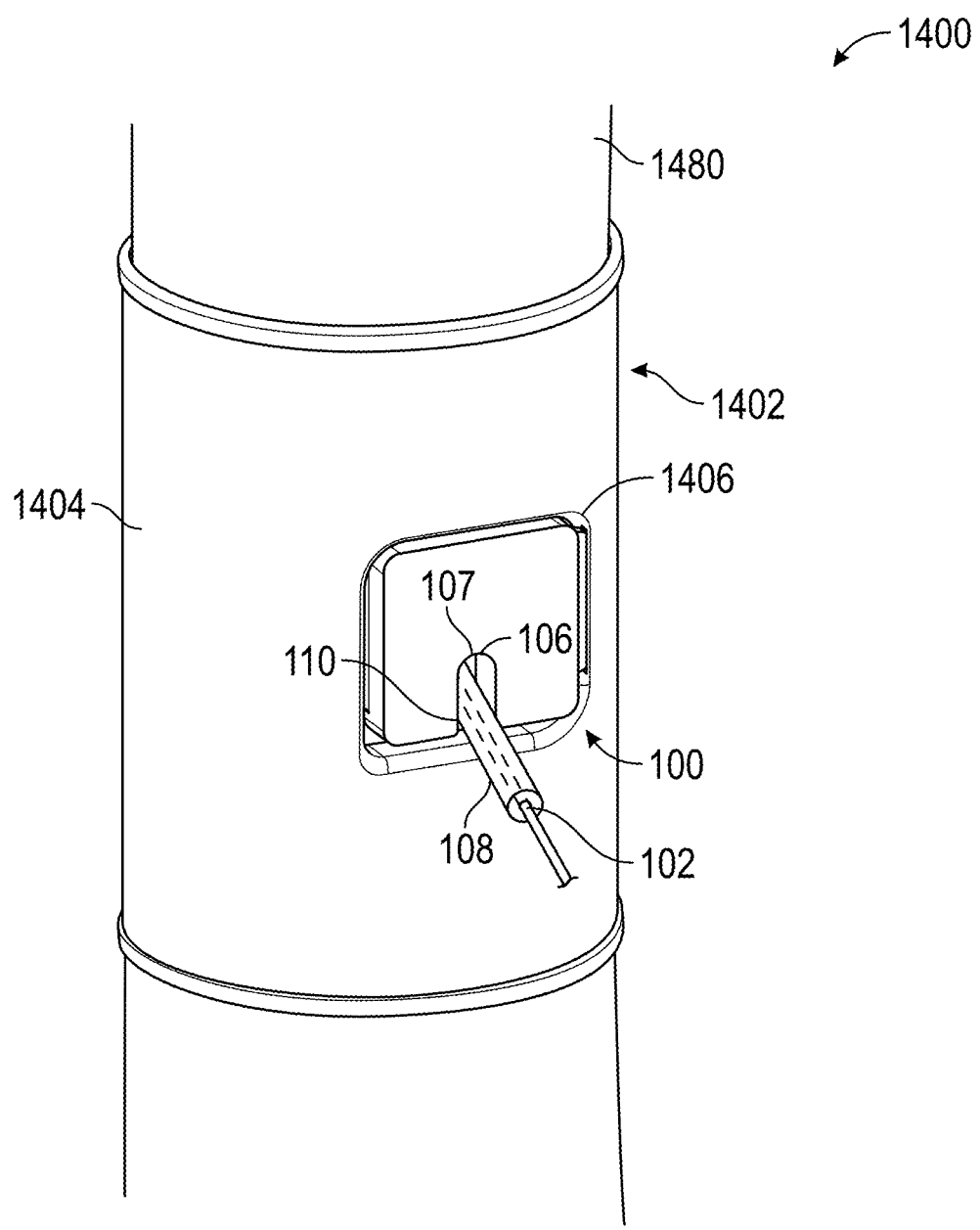
FIG. 15 illustrates a perspective view of the system of FIG. 14 in which the ultrasound device is attached to the supporting structure.

In this regard, FIG. 15 illustrates a perspective view of system 1400 in which ultrasound device 100 is attached to supporting structure 1402 in the foregoing manner, wherein supporting structure 1402 is attached to patient extremity 1480. As shown in FIG. 15, in the connected state, at least a portion of guide channel cut-out or aperture 106 of ultrasound device 100 is situated above opening 1410. Needle guide assembly 108 is disposed within and may be pivotally connected to guide channel cut-out or aperture 106 at pivot point 110 as was previously described. This configuration allows needle guide assembly 108 to be rotated about pivot point 110 to a desired angle within guide channel cut-out or aperture 106 and also allows needle 102 within needle guide assembly 108 to be inserted into extremity 1480 of the patient via opening 1410.

In an embodiment, guide channel cut-out or aperture 106 is shaped such that needle guide assembly 108 can be rotated therein to a shallow angle in a desired direction (e.g., from 0 up to 90 degrees total range of movement). In one example scenario, this may enable a practitioner/user to flatten an angle of the needle upon penetrating a blood vessel, thereby allowing for advancement of a catheter. In an embodiment in which needle guide assembly 108 is connected to guide channel cut-out or aperture 106 at a pivot point 110, pivot point 110 may be positioned away from left side 107 of guide channel cut-out or aperture 106 to ensure that needle guide assembly 108 can be rotated to the desired shallow angle. However, this is an example only, and pivot point 110 may be positioned anywhere within guide channel cut-out or aperture 106 that facilitates rotation to the desired angle depending upon the implementation.

Figure 16:
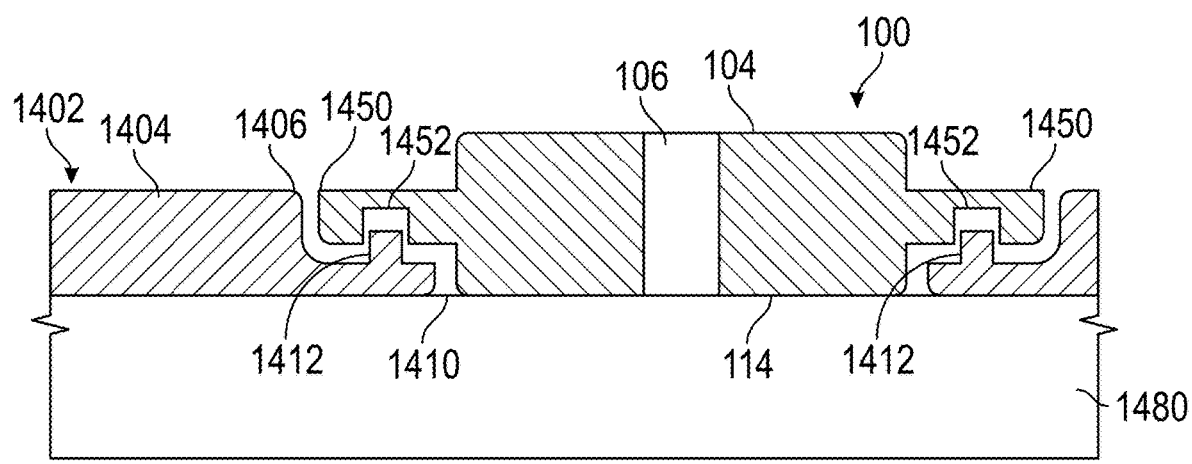
FIG. 16 illustrates a side cutaway view of the ultrasound device of FIG. 14 attached to the supporting structure of FIG. 14, wherein the supporting structure is attached to the patient.

FIG. 16 illustrates a side cutaway view of ultrasound device 100 and supporting structure 1402 when supporting structure 1402 is attached to patient extremity 1480 and ultrasound device 100 is connected to supporting structure 1402. As shown in FIG. 16, ultrasound device 100 is at least partially inserted within recess 1406 of supporting structure 1402 such that male mating elements 1412 of supporting structure 1402 are inserted within, and thereby mate with, corresponding female mating elements 1452 of ultrasound device 100. In this connected state, body side 114 of ultrasound device 100 is in contact with patient extremity 1480 and at least a portion of guide channel cut or aperture 106 of ultrasound device 100 is situated above opening 1410. Needle guide assembly 108 may be disposed within and pivotally connected to guide channel cut-out or aperture 106 as was previously described. As noted above, this configuration allows needle guide assembly 108 to be rotated to a desired angle within guide channel cut-out or aperture 106 and also allows needle 102 within needle guide assembly 108 to be inserted into extremity 1480 of the patient via opening 1410.

In the above-described embodiment of FIGS. 14-16, the sizes and/or shapes of male mating elements 1412 and/or female mating elements 1452 may be varied to adjust how securely or tightly ultrasound device 100 is connected to supporting structure 1402 without affecting the ease of use of the composite device. For example, male mating elements 1412 may be sized so that they provide a snug fit with female mating elements 1452. Furthermore, in an alternate embodiment, tabs 1450 of ultrasound probe housing 104 may comprise male connectors and recessed frame 1408 of supporting structure 1402 may comprise female connectors. Still further, tabs 1450 of ultrasound probe housing 104 may comprise a mix of male and female connectors and recessed frame 1408 may comprise a corresponding mix of female and male connectors.

Aside from studs/pegs and holes, a variety of other mechanical fastener types may be used to connect ultrasound device 100 to supporting structure 1402. For example, any of screws, magnets, rivets, snap fits, interference fits (e.g., press fits and friction fits), adhesives and tapes, threaded fasteners, quarter turn fasteners, and hook and loop fasteners may be used to connect ultrasound device 100 to supporting structure 1402 in accordance with embodiments. For example, in accordance with one embodiment, a snap fit design may be used to enable a user to simply snap ultrasound device 100 into recess 1406. In accordance with another embodiment, recess 1406 may be sized and shaped such that ultrasound device 100 forms an interference fit therewith. The choice of fastener type may be guided by factors such as ease of connection, ease of removal, stability of connection, or the like. The choice of fastener type will drive which attachment features must be present on supporting structure 1402 to connect ultrasound device 100 thereto.

Figure 17:
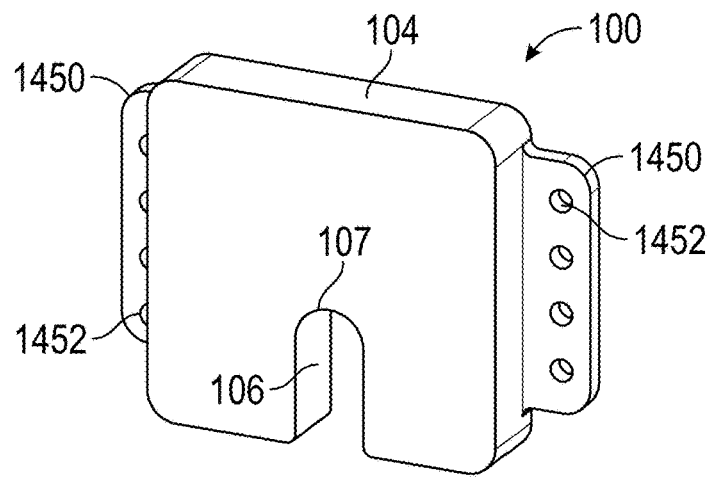
FIG. 17 illustrates another perspective view of the ultrasound device of FIG. 14.

FIG. 17 illustrates another perspective view of ultrasound device 100 of FIG. 14. As can be seen in FIG. 17, tabs 1450 extend from the sides of ultrasound probe housing 104 that are to either side of the side that includes guide channel cut-out or aperture 106. It should be appreciated, however, that guide channel cut-our or aperture 106 can be oriented in any of four different directions when ultrasound device is connected 100 to supporting structure 1402. This is due to the fact that female mating elements 1452 of tabs 1450 are sized and positioned such that they can be selectively mated with male mating elements 1412 of any two opposing sides of recessed frame 1408.

Figure 18:
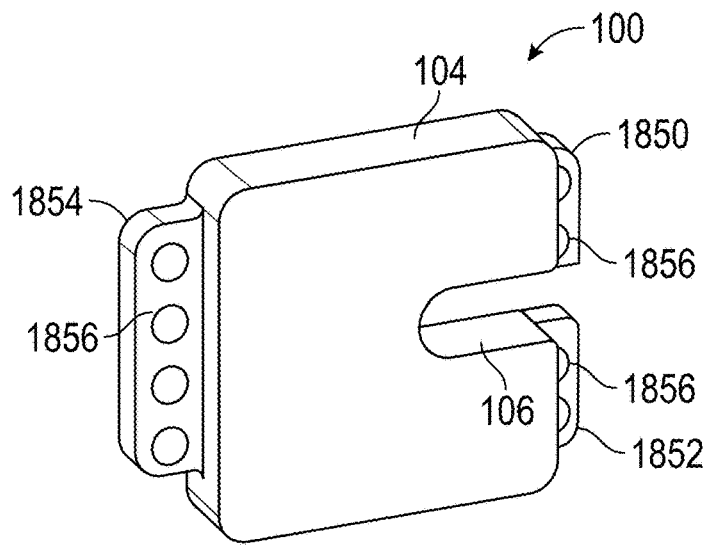
FIG. 18 illustrates a perspective view of an ultrasound device with integrated mating elements for connecting to a supporting structure in accordance with an alternate embodiment.

In alternate embodiments, the tabs of ultrasound device 100 need not be implemented on the sides of ultrasound probe housing 104 that are to either side of the side that includes guide channel cut-out or aperture 106. For example, FIG. 18 illustrates a perspective view of an embodiment of ultrasound device 100 in which the side of ultrasound probe housing 104 that includes guide channel cut-out or aperture 106 has extending therefrom a rigid or semi-rigid first tab 1850 and a rigid or semi-rigid second tab 1852. First tab 1850 and second tab 1852 are located to either side of guide channel cut-out or aperture 106 and each includes a number female mating elements 1856. Furthermore, a rigid or semi-rigid third tab 1854 extends from the side of ultrasound probe housing 104 that is opposite the side that includes guide channel cut-out or aperture 106 and includes a number of female mating elements 1856. Female mating elements 1856 of first tab 1850, second tab 1852 and third tab 1854 are sized and positioned such that they can be selectively engaged with male mating elements of opposing sides of a recessed frame of a supporting structure. That is to say, female mating elements 1856 of first tab 1850 and second tab 1852 are sized and positioned to engage with male mating elements of one side of a recessed frame of a supporting structure, while female mating elements 1856 of third tab 1854 are sized and positioned to engage with male mating elements of the other side of the recessed frame of the supporting structure. This enables the embodiment of ultrasound device 100 shown in FIG. 18 to be connected to the supporting structure.

Figure 19:
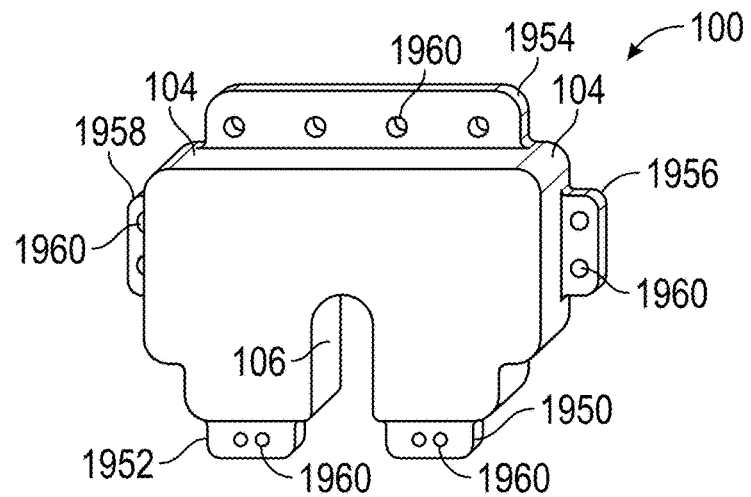
FIG. 19 illustrates a perspective view of an ultrasound device with integrated mating elements for connecting to a supporting structure in accordance with a further alternate embodiment.

FIG. 19 illustrates a perspective view of yet another embodiment of ultrasound device 100 having integrated mating elements for connecting to a supporting structure. As shown in FIG. 19, the side of ultrasound probe housing 104 that includes guide channel cut out or aperture 106 has extending therefrom a rigid or semi-rigid first tab 1950 and a rigid or semi-rigid second tab 1952. First tab 1950 and second tab 1952 are located to either side of guide channel cut-out or aperture 106 and each includes a number of female mating elements 1960. Furthermore, a rigid or semi-rigid third tab 1954 extends from the side of ultrasound probe housing 104 that is opposite the side that includes guide channel cut-out or aperture 106 and includes a number of female mating elements 1960. Also, a rigid or semi-rigid fourth tab 1956 and a rigid or semi-rigid fifth tab 1958 extend from the sides of ultrasound probe housing 104 that are to either side of the side of ultrasound probe housing 104 that includes guide channel cut out or aperture 106, and each of fourth tab 1956 and fifth tab 1958 includes a number of female mating elements 1960. Female mating elements 1960 of first tab 1950, second tab 1952, third tab 1954, fourth tab 1956 and fifth tab 1958 are sized and positioned such that they can be selectively engaged with male mating elements of all four sides of a recessed frame of a supporting structure. That is to say, female mating elements 1960 of first tab 1950 and second tab 1952 are sized and positioned to engage with male mating elements of a first side of a recessed frame of a supporting structure, female mating elements 1960 of third tab 1954 are sized and positioned to engage with male mating elements of a second side of the recessed frame that is opposite the first side, female mating elements 1960 of fourth tab 1956 are sized and positioned to engage with male mating elements of a third side of the recessed frame, and female mating elements 1960 of fifth tab 1958 are sized and positioned to engage with male mating elements of a fourth side of the recessed frame that is opposite the third side. This enables the embodiment of ultrasound device 100 shown in FIG. 19 be connected to the supporting structure. It will be appreciated that the embodiments shown in FIGS. 17, 18, and 19 can vary further in appearance depending partly on the intended application and type of mechanical fastener used. For instance, if the female mating elements of these figures and the corresponding male mating elements of recessed frame 1408 of supporting structure 1402 comprise paired magnets, then no visible holes or pegs would be required thereby creating multiple smoother surfaces. Such an embodiment may be favorable in addressing surface sterility for more immune-sensitive procedures.

Figure 20:
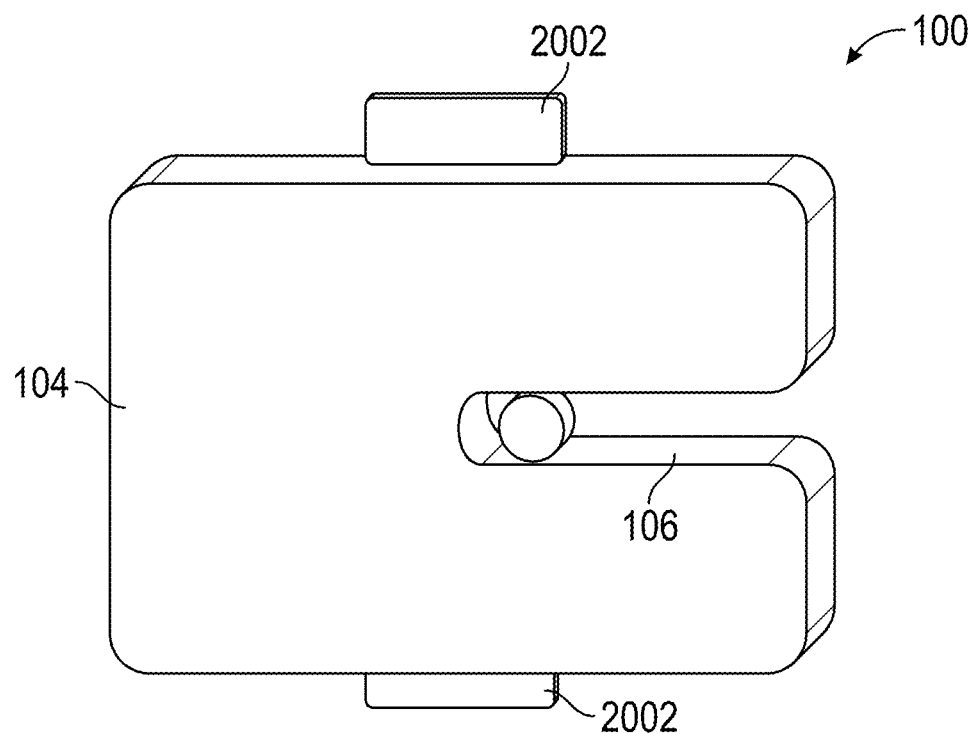
FIG. 20 illustrates a top perspective view of an ultrasound device comprising an ultrasound probe housing with rails extending from opposite sides thereof in accordance with an embodiment.
Figure 21:
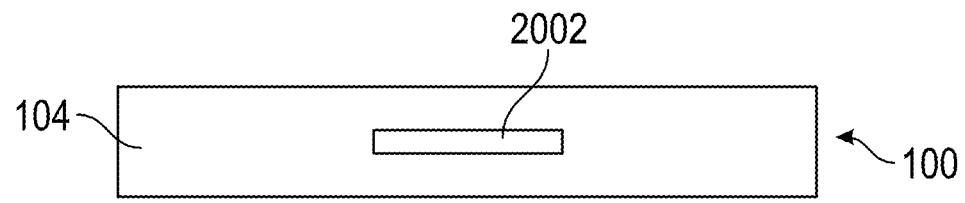
FIG. 21 illustrates a side perspective view of the ultrasound device of FIG. 20.

FIG. 20 illustrates a top perspective view of an alternate embodiment of ultrasound device 100 in which ultrasound probe housing 104 has rails 2002 extending from opposite sides thereof, while FIG. 21 illustrates a side perspective view of the same device. As will now be described in reference to FIG. 22, ultrasound device 100 of FIGS. 20 and 21 is configured for use with a supporting structure 2202 (e.g., cuff or sleeve) that is suitable for attachment to a patient extremity 2280 (e.g., an arm of a patient).

Figure 22:
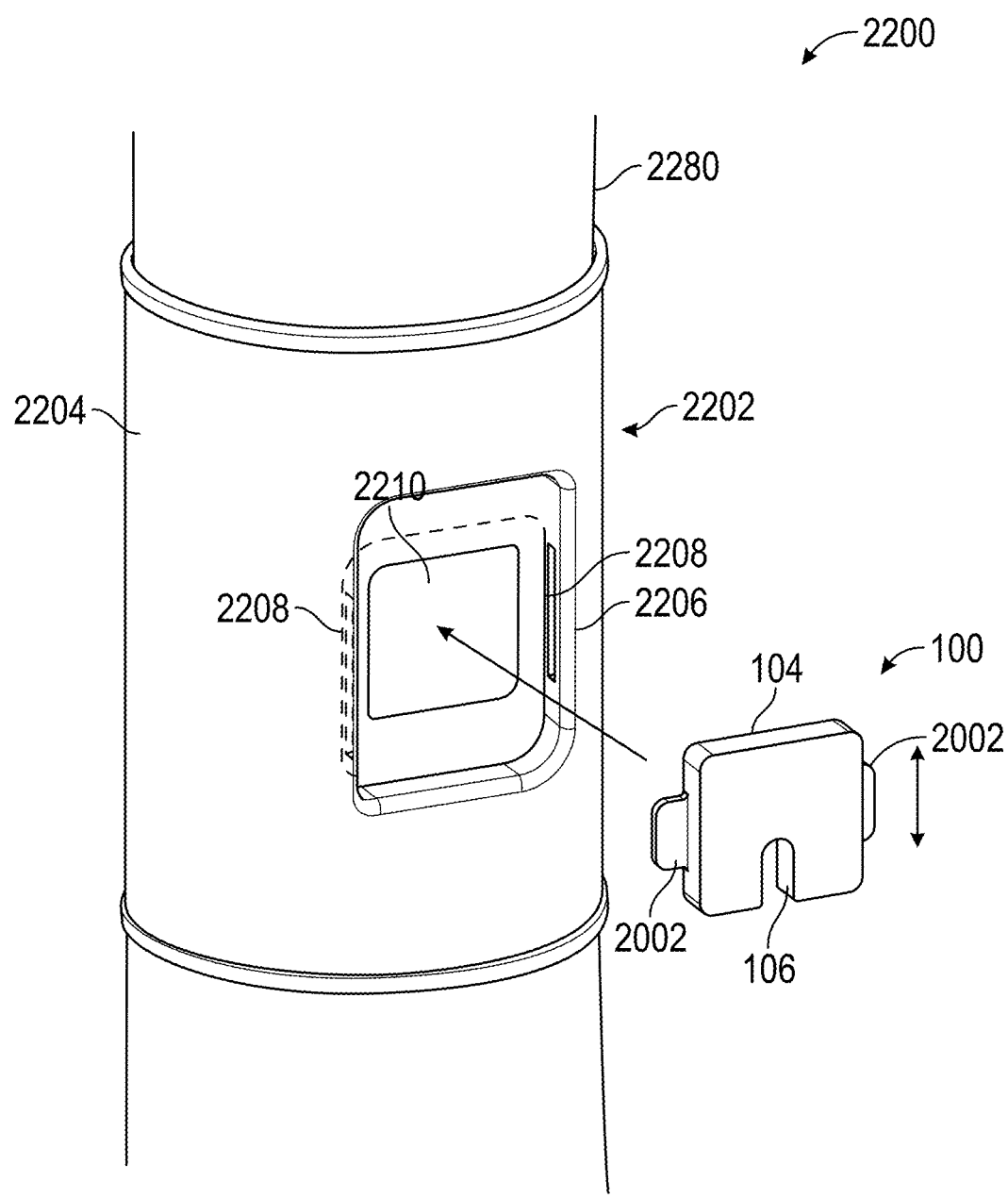
FIG. 22 illustrates a perspective view of a system comprising the ultrasound device of FIG. 20 and a supporting structure to which it may be attached, wherein the supporting structure is attached to the patient, in accordance with an embodiment.

As shown in FIG. 22, a system 2200 comprises the embodiment of ultrasound device 100 of FIGS. 20 and 21 and supporting structure 2202. Supporting structure 2202 comprises an ambient side 2204 having an outer surface within which is formed a recess 2206. Supporting structure 2202 also comprises a body side that is opposite ambient side 2204 and faces toward the body of the patient during use. Recess 2206 is adapted to accommodate insertion of at least a portion of ultrasound device 100. Recess 2206 includes sidewalls that surround an opening 2210 that passes fully through supporting structure 2202. Each of two opposing sidewalls of recess 2206 comprises a groove 2208. Each groove 2208 is adapted to receive a corresponding one of rails 2002. The insertion of rails 2002 of ultrasound device 100 into corresponding ones of grooves 2208 serves to connect ultrasound device 100 to supporting structure 2202. The sidewalls of recess 2206 that include grooves 2208 are longer than the sides of ultrasound probe housing 104 from which rails 2002 extend. Furthermore, rails 2002 are configured such that they can slide within grooves 2208. Taken together, these features enable vertical (up and down) movement of ultrasound device 100 within recess 2206 while connected to supporting structure 2202.

A practitioner may thus move ultrasound device 100 while it is connected to supporting structure 2202 to identify a desired target anatomical location from the images generated by the ultrasound waves produced by probes 105 disposed therein. Furthermore, movement of ultrasound device 100 in this manner may allow for controlled and fine adjustments of the incorporated needle guide assembly 108 and needle 102 in a direct plane of a center of a target vessel or structure to maximize accuracy and precision of a procedure.

In an embodiment, after a desired location has been identified (e.g., such as directly above or aligned with a vein) through movement of ultrasound device 100 within recess 2206, a locking mechanism may be applied to secure ultrasound device 100 in place. Any of a wide variety of locking mechanisms may be used for this purpose, including but not limited to locking tabs, tightening wing nuts at one or more positions, push and release button or pin, buckle latch, Velcro or other hook and loop tightening, or manually holding ultrasound device 100 in place. At this point, needle 102 can be inserted through needle guide assembly 108 within guide channel cut-out or aperture 106 so that, e.g., a vessel can be punctured and/or cannulated.

It can be seen in FIG. 22 that ultrasound probe housing 104 including rails 2002 is wider than recess 2206 which means that some mechanism must be implemented to snap rails 2002 into corresponding grooves 2208. In an embodiment, this is achieved by implementing rails 2002 with a rigid or semi-rigid material that deforms slightly under pressure to accommodate insertion into recess 2206 but that will snap back into place after rails 2002 are aligned with grooves 2208. In another embodiment, rails 2002 are configured to at least partially retract into the sidewalls of ultrasound probe housing 104 under pressure thereby enabling ultrasound device 100 to be inserted into recess 2206, but are also biased (e.g., spring biased) so that they will snap outward into grooves 2208 when aligned with grooves 2208. In another embodiment, supporting structure 2202 may open or enlarge to allow rails 2002 of ultrasound probe housing 104 to be inserted into recess 2206, after which supporting structure 2202 may then be closed or reduced in size, thereby securing ultrasound probe housing 104 in place. Still other techniques may be used to insert rails 2002 into corresponding grooves 2208. In a still further embodiment, ultrasound device 100 may be pre-fitted (even permanently) within supporting structure 2202.

Figure 23:
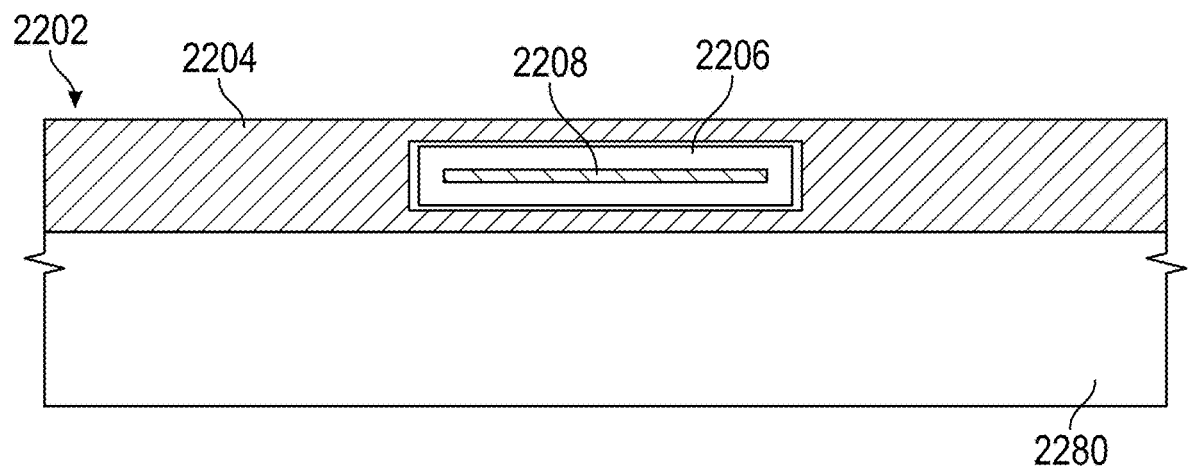
FIG. 23 illustrates a side cutaway view of the supporting structure of FIG. 20 attached to the patient.

FIG. 23 illustrates a side cutaway view of the supporting structure of FIG. 20 attached to patient extremity 2280 that shows groove 2206 within a sidewall of recess 2208.

Figure 24:
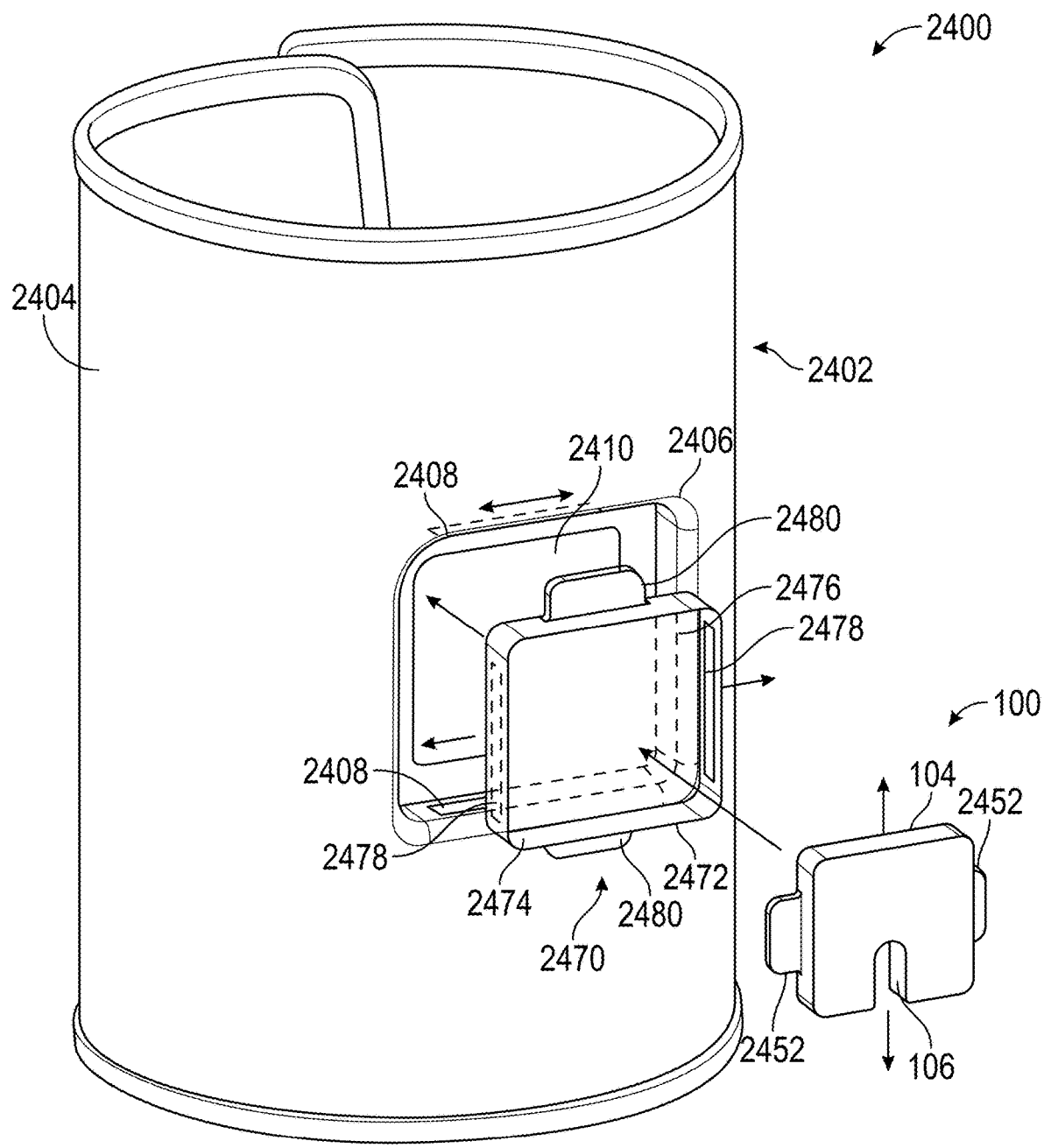
FIG. 24 illustrates a perspective view of a system comprising an ultrasound device, a frame, and a supporting structure, wherein the ultrasound device comprises integrated rails for connection to and vertical movement within the frame, and wherein the frame comprises integrated rails for connection to and horizontal movement within a recess of the supporting structure, in accordance with an embodiment.

FIG. 24 illustrate a perspective view of a system 2400 that enables both horizontal (side to side) and vertical (up and down) movement of ultrasound device 100 when it is connected to a supporting structure. In particular, as shown in FIG. 24, system 2400 includes an embodiment of ultrasound device 100, a frame 2470, and a supporting structure 2402. In the embodiment of ultrasound device 100 of FIG. 24, ultrasound probe housing 104 comprises two rails 2452 that extend respectively from the vertical sides thereof.

Frame 2470 comprises a frame housing 2472 that defines a cavity 2474. Cavity 2474 is adapted to accommodate insertion of at least a portion of ultrasound device 100. Cavity 2474 includes four interior sidewalls that surround an opening 2476 that passes fully through frame 2470. Each of the interior vertical sidewalls of cavity 2474 comprises a groove 2478. Each groove 2478 is adapted to receive a corresponding one of rails 2452. The insertion of rails 2452 of ultrasound device 100 into corresponding ones of grooves 2478 serves to connect ultrasound device 100 to frame 2470. The sidewalls of cavity 2474 that include grooves 2478 are longer than the sides of ultrasound probe housing 104 from which rails 2452 extend. Furthermore, rails 2452 are configured such that they can slide within grooves 2478. Taken together, these features enable vertical (up and down) movement of ultrasound device 100 within frame 2470 while connected thereto.

As further shown in FIG. 24, frame 2470 comprises two horizontal rails 2480 that extend from the external horizontal sidewalls of frame housing 2472.

Supporting structure 2402 comprises an ambient side 2404 having an outer surface within which is formed a recess 2406. Supporting structure 2402 also comprises a body side that is opposite ambient side 2404 and faces toward the body of the patient during use. Recess 2406 is adapted to accommodate insertion of at least a portion of frame 2470. Recess 2406 includes four sidewalls that surround an opening 2410 that passes fully through supporting structure 2402. Each of two horizontal sidewalls of recess 2406 comprises a groove 2408. Each groove 2408 is adapted to receive a corresponding one of rails 2480. The insertion of rails 2480 of frame 2470 into corresponding ones of grooves 2408 serves to connect frame 2470 to supporting structure 2402. The sidewalls of recess 2406 that include grooves 2408 are longer than the sides of frame housing 2472 from which rails 2480 extend. Furthermore, rails 2480 are configured such that they can slide within grooves 2408. Taken together, these features enable horizontal (side to side) movement of frame 2470 within recess 2406 while connected to supporting structure 2402.

Thus, when ultrasound device 100 is connected to frame 2470 and frame 2470 is connected to supporting structure 2402, a practitioner may move ultrasound device 100 both in a vertical direction (by sliding ultrasound device 100 within frame 2470) and in a horizontal direction (by sliding frame 2470 within supporting structure 2402). However, regardless of the ultimate position of ultrasound device 106, at least a portion of guide channel cutout or aperture 106 will be positioned over both opening 2476 and opening 2410, thereby providing a channel for needle insertion. As discussed above with respect to the embodiments of FIGS. 20-23, moving ultrasound device 100 in this manner can allow a practitioner to identify a desired target anatomical location from the images generated by the ultrasound waves produced by probes 105 disposed therein. Furthermore, movement of ultrasound device 100 in this manner may allow for controlled and fine adjustments of the incorporated needle guide assembly 108 and needle 102 in a direct plane of a center of a target vessel or structure to maximize accuracy and precision of a procedure.

In an embodiment, after a desired location has been identified (e.g., such as directly above or aligned with a vein) through movement of ultrasound device 100 within frame 2470 and/or movement of frame 2470 within recess 2406, one or more locking mechanisms may be applied to secure both ultrasound device 100 and frame 2470 in place. Any of a wide variety of locking mechanisms may be used for these purposes, including but not limited to locking tabs, tightening wing nuts at one or more positions, push and release button or pin, buckle latch, Velcro or other hook and loop tightening, or manually holding ultrasound device 100 in place. At this point, needle 102 can be inserted through needle guide assembly 108 within guide channel cut-out or aperture 106 so that, e.g., a vessel can be punctured and/or cannulated.

It can be seen in FIG. 24 that ultrasound probe housing 104 including rails 2452 is wider than cavity 2474 which means that some mechanism must be implemented to snap rails 2452 into corresponding grooves 2478. In an embodiment, this is achieved by implementing rails 2452 with a rigid or semi-rigid material that deforms slightly under pressure to accommodate insertion into cavity 2474 but that will snap back into place after rails 2452 are aligned with grooves 2478. In another embodiment, rails 2452 are configured to at least partially retract into the sidewalls of ultrasound probe housing 104 under pressure thereby enabling ultrasound device 100 to be inserted into cavity 2474, but are also biased (e.g., spring biased) so that they will snap outward into grooves 2478 when aligned with grooves 2478. Similar techniques may be adopted to enable rails 2480 of frame 2470 to be snapped into grooves 2408 of supporting structure 2402. Still other techniques (e.g., temporary expansion of frame 2470 and/or supporting structure 2402, or pre-fitting ultrasound device 100 within frame 2470 and/or frame 2470 within recess 2406 of supporting structure 2402) may be used to insert rails 2452 of ultrasound device 100 into corresponding grooves 2478 of frame 2470 and/or to insert rails 2480 of frame 2470 into corresponding grooves 2408 of supporting structure 2402.

The foregoing embodiments may advantageously be used to allow everyone from phlebotomists to nurses to physician's assistants to draw blood samples quickly and with a high-fidelity, low error rate. For example, a system such as system 2200 or system 2400 can be used to increase the stability of ultrasound device 100 while enabling fine movement to locate and target a desired structure. This minimizes the need for two hand-eye coordination, which is currently required with ultrasound-guided procedures, wherein the ultrasound probe must be balanced with one hand, while the other hand attempts venipuncture with an unsupported needle and concurrently tracking the needle advancement on an ultrasound screen at a distance from the user.

Figure 25:
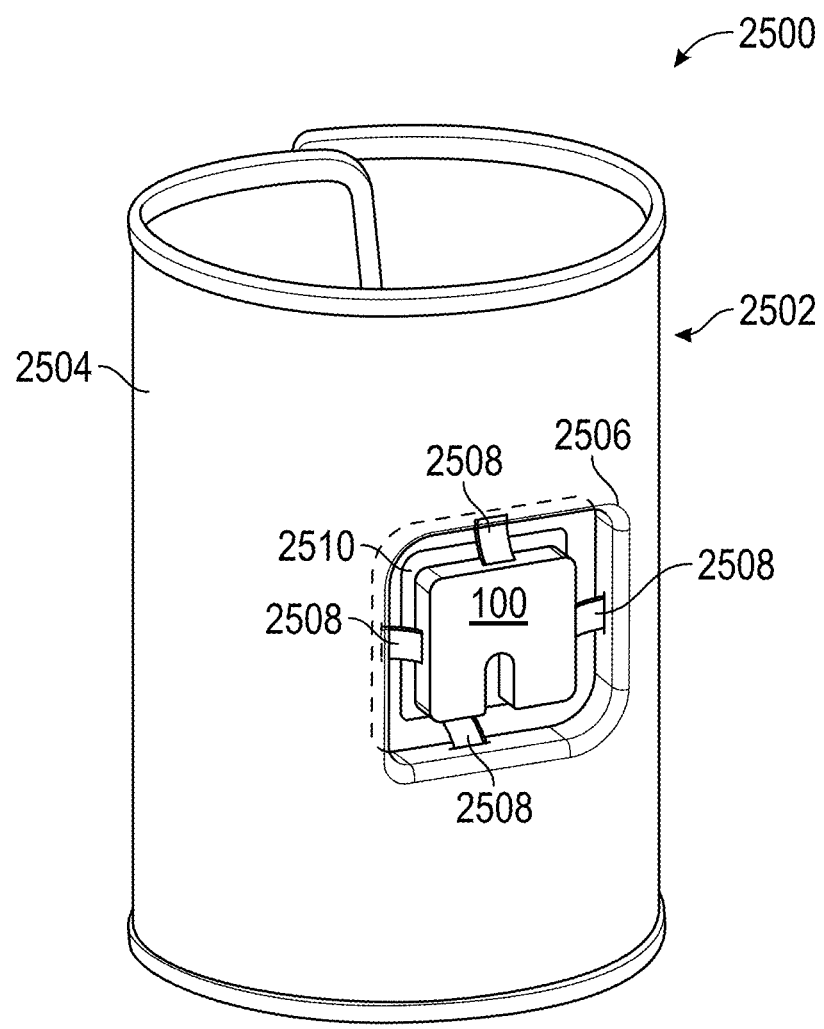
FIG. 25 illustrates a perspective view of a further system in which an ultrasound device may be connected to and also positioned within a recess of a supporting structure in accordance with an embodiment.

FIG. 25 illustrates a perspective view of a further system 2500 in which ultrasound device 100 may be connected to and also positioned within a recess 2506 of a supporting structure 2502. In particular, as shown in FIG. 25, supporting structure 2502 comprises an ambient side 2504 having an outer surface within which is formed recess 2506. Supporting structure 2502 also comprises a body side that is opposite ambient side 2504 and faces toward the body of the patient during use. Recess 2506 is adapted to accommodate insertion of at least a portion of ultrasound device 100. Recess 2506 includes four sidewalls that surround an opening 2510 that passes fully through supporting structure 2502. Supporting structure 2502 further includes a plurality of attachment arms 2508, wherein each attachment arm 2508 extends from a corresponding one of the four sidewalls of recess 2506. Each attachment arm 2508 can be connected to a corresponding side of ultrasound probe housing 104 of ultrasound device 100. In an embodiment, a portion of each attachment arm 2508 may be extracted from or retracted into its corresponding sidewall, thereby allowing a practitioner to selectively lengthen or shorten each attachment arm 2508. In accordance with such an embodiment, shortening one attachment arm 2508 and lengthening the opposite attachment arm 2508 allows for movement for example, in the direction of the shortened attachment arm 2508.

Figure 26:
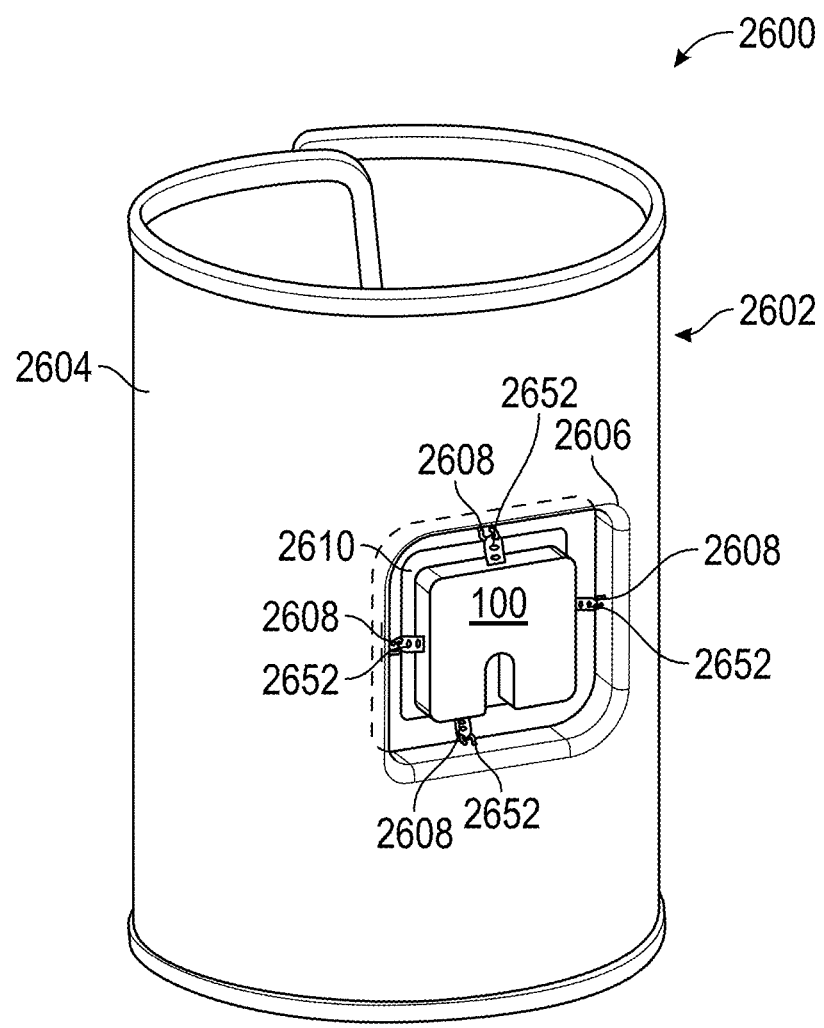
FIG. 26 illustrates a perspective view of a still further system in which an ultrasound device may be connected to and also positioned within a recess of a supporting structure in accordance with an embodiment.

FIG. 26 illustrates a perspective view of a still further system 2600 in which ultrasound device 100 may be connected to and also positioned within a recess 2606 of a supporting structure 2602. In particular, as shown in FIG. 26, supporting structure 2602 comprises an ambient side 2604 having an outer surface within which is formed recess 2606. Supporting structure 2602 also comprises a body side that is opposite ambient side 2604 and faces toward the body of the patient during use. Recess 2606 is adapted to accommodate insertion of at least a portion of ultrasound device 100. Recess 2606 includes four sidewalls that surround an opening 2610 that passes fully through supporting structure 2602. Supporting structure 2602 further includes a plurality of connection points 2608 (e.g., hooks) wherein each connection point 2608 is attached to or integrated with a corresponding one of the four sidewalls of recess 2606.

In the embodiment of FIG. 26, ultrasound device 100 also includes a plurality of connectors 2652, wherein each connector 2652 is attached to or integrated with a corresponding side of ultrasound probe housing 104 and is also suitable for removable attachment to a corresponding one of connection points 2608. For example, as shown in FIG. 26, each connector 2652 may comprise an elongated tab which itself comprises a series of holes which are located at various distances from a corresponding side of ultrasound probe 104, wherein each hole may be engaged with a corresponding connection point 2608. By varying which hole of a connector 2652 is selected for engagement with a corresponding connection point 2608, a practitioner may selectively lengthen or shorten the attachment distance between each side of ultrasound device 100 and a corresponding sidewall of recess 2606, wherein lengthening or shortening on one side may be compensated for by making the opposite adjustment on the other. Such an embodiment also advantageously enables stable positioning of ultrasound device 100 within recess 2606 of supporting structure 2602.

In at least some of the foregoing examples, the supporting structure is in the form of a sleeve or cuff that is suitable for attachment to a limb or extremity of a patient. However, a supporting structure can be any of any form appropriate for the bodily location of the procedure to be performed. For example, as previously noted, if the procedure location is along the arm or hand, the supporting structure may be in the shape of sleeve or cuff to which ultrasound device 100 of the present invention joins. However, the supporting structure may also be C-shaped or U-shaped (e.g., a C-clamp or U-clamp) to facilitate adherence to the body of the patient requiring the procedure. It should be understood that anatomy location for the procedure to be performed may dictate which supporting structure is best suited for use with ultrasound device 100 of the present invention. Regardless of the particular supporting structure, in addition to adhering to the body of the patient, the supporting structure houses ultrasound device 100 for operation of needle guide assembly 108 within guide channel cutout or aperture 106.

In the systems discussed above with respect to FIGS. 20-26, the supporting structure (whether it is a cuff, sleeve, C-clamp, U-clamp, or the like) includes a recess within which is formed an opening, and ultrasound device 100 can operate within that recess. The recess is intentionally larger than ultrasound device 100 to allow some range of movement in at least two directions (up and down an arm for instance) relative to the surface of the anatomy on which ultrasound device 100 will sit even when connected to the supporting structure. Such systems enable ultrasound device 100 to be moved around by the operator until the operator identifies the approximate underlying anatomy for the procedure. At that point, ultrasound device 100 can be locked into place within the recess of the supporting structure. Even when locked, the operator will still have some range of motion by the inherent features of ultrasound device 100 with its associated needle guide assembly 108. That will allow fine tuning in the locked position and greater ease of use for the operator, which is important since the narrow width of a vessel leaves little room for error. Such a system may advantageously allow a single operator to perform a venipuncture without the need to hold ultrasound device 100. Without such a system, one hand would be required to balance an unsupported ultrasound device 100, while the other hand attempts to cannulate a vessel while visualizing the narrow vessel and needle on an ultrasound screen located at a distance from the user. In contrast, using the systems discussed above with respect to FIG. 20-26, both hands if needed may be freed to work the needle and any additional tool required, like collection tubes, IV tubing, J loop, IV/catheter insert, or the like.

Figure 27:
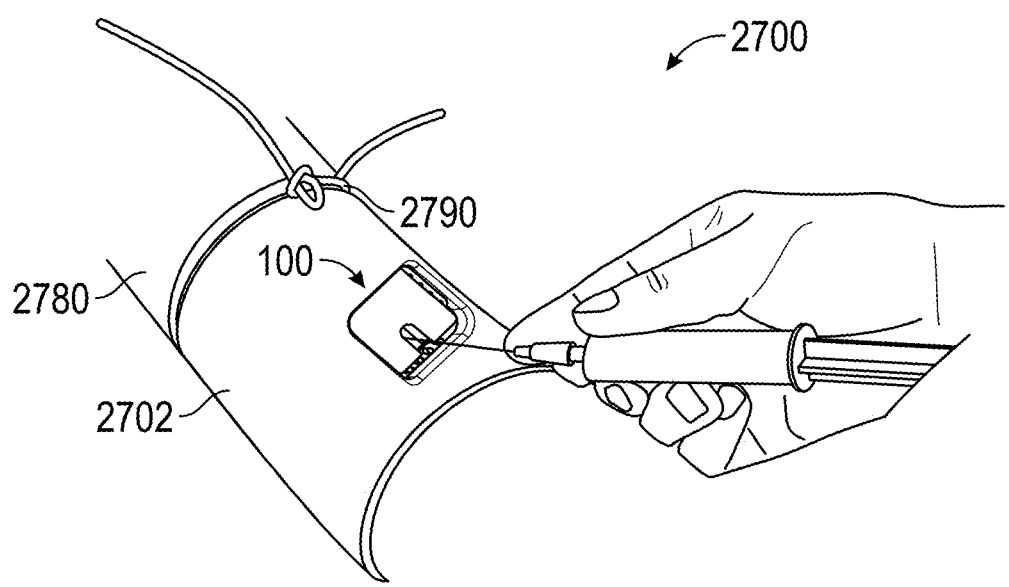
FIG. 27 illustrates a perspective view of a system comprising a supporting structure that is attached to a patient arm and an ultrasound device connected to the supporting structure, wherein the supporting structure includes an integrated tourniquet and wherein the system is used to perform a medical procedure, in accordance with an embodiment.

FIG. 27 illustrates a perspective view of a system 2700 comprising a supporting structure 2702 attached to a patient arm 2780 and an ultrasound device 100 connected to supporting structure 2702, wherein supporting structure 2702 includes an integrated tourniquet 2790 and wherein system 2700 is used to perform a medical procedure, such as a blood draw. With respect to FIG. 27, it is to be understood that ultrasound device 100 may be connected to supporting structure 2702 in any suitable manner, including any manner described herein. Integrated tourniquet 2790 may comprise a cord or tube made of rubber, silicone, or other suitable material for tightening around a limb or extremity to apply pressure thereto in order to limit the flow of blood. Integrated tourniquet 2790 in conjunction with ultrasound device 100 may be used, for example, by a phlebotomist to assess and determine a location of a suitable vein for venipuncture.

In the embodiment shown in FIG. 27, integrated tourniquet 2790 is incorporated into an end portion of supporting structure 2702 that is expected to be most proximal to the patient. Integrated tourniquet 2790 may be tightened, for example, by drawing together and securing (e.g., knotting) two ends of a tube that comprises the tourniquet. Integrated tourniquet 2790 may also be implemented as an adjustable Velcro strap or other structure that is adjustable to provide circumferential compression necessary to perform the desired medical procedure.

Figure 28:
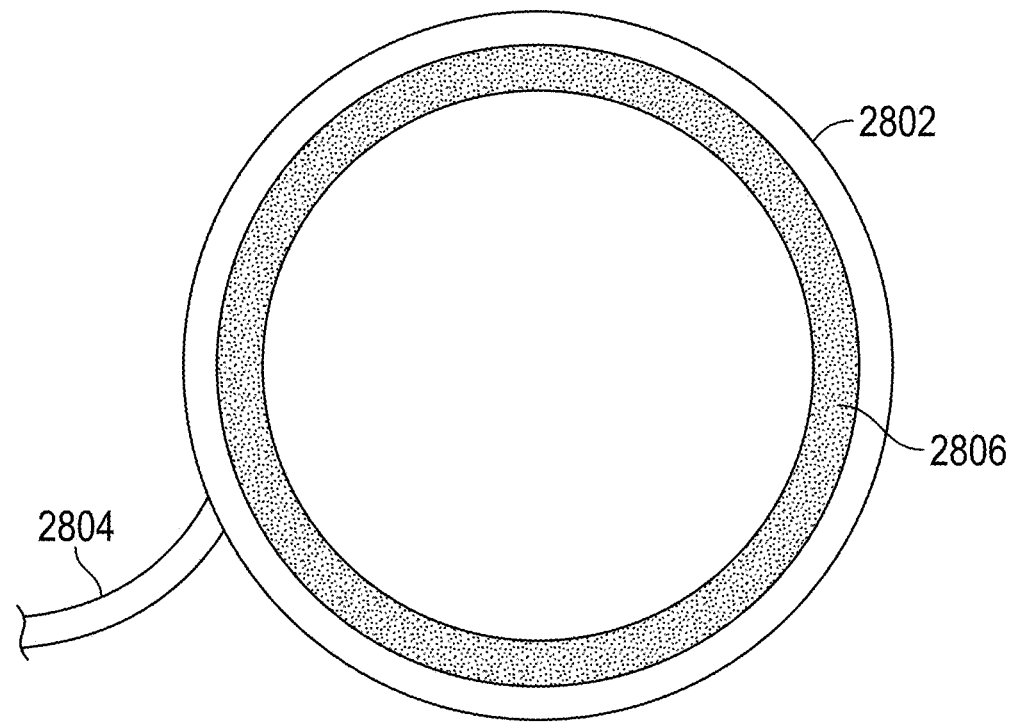
FIG. 28 illustrates a cross-sectional view of a supporting structure that comprises an integrated tourniquet in the form of an inflatable tube or ring in accordance with an embodiment.

In an embodiment, the tourniquet may be implemented as an inflatable tube or ring that is attached to or otherwise integrated with the supporting structure and that can be expanded through the injection therein of air, thereby causing the tube or ring to tighten around a limb or extremity of a patient. For example, FIG. 28 illustrates a cross-sectional view of a supporting structure 2802 that comprises an integrated tourniquet in the form of an inflatable tube or ring 2806. Supporting structure 2802 further comprises a tube 2804 that is connected to inflatable tube or ring 2806 and through which air may be injected into and released from inflatable tube or ring 2860, thereby causing inflatable tube or ring 2860 to expand or contract accordingly. In the expanded state, inflatable tube or ring 2860 applies circumferential compression to an extremity of a patient. It is noted that the inflatable element of supporting structure 2802 need not be ring shaped nor surround the entire extremity of the patient. For example, the inflatable element may instead comprise a bladder that is located over only a portion of the patient's extremity but that nevertheless provides a sufficient degree of compression thereto when in the expanded state.

In an embodiment, a supporting structure such as supporting structure 2702 of FIG. 27 may also comprise an additional posterior rigid or hard surface to encourage extremity straightening, such as straightening arm 2780 at the elbow, to aid the procedure to be performed on the patient. This can help maximize the surface area available of an extremity for vessel identification and, if used for an upper extremity, may allow for optimization of the antecubital fossa, the most utilized area of the arm for venipuncture.

Figure 29:
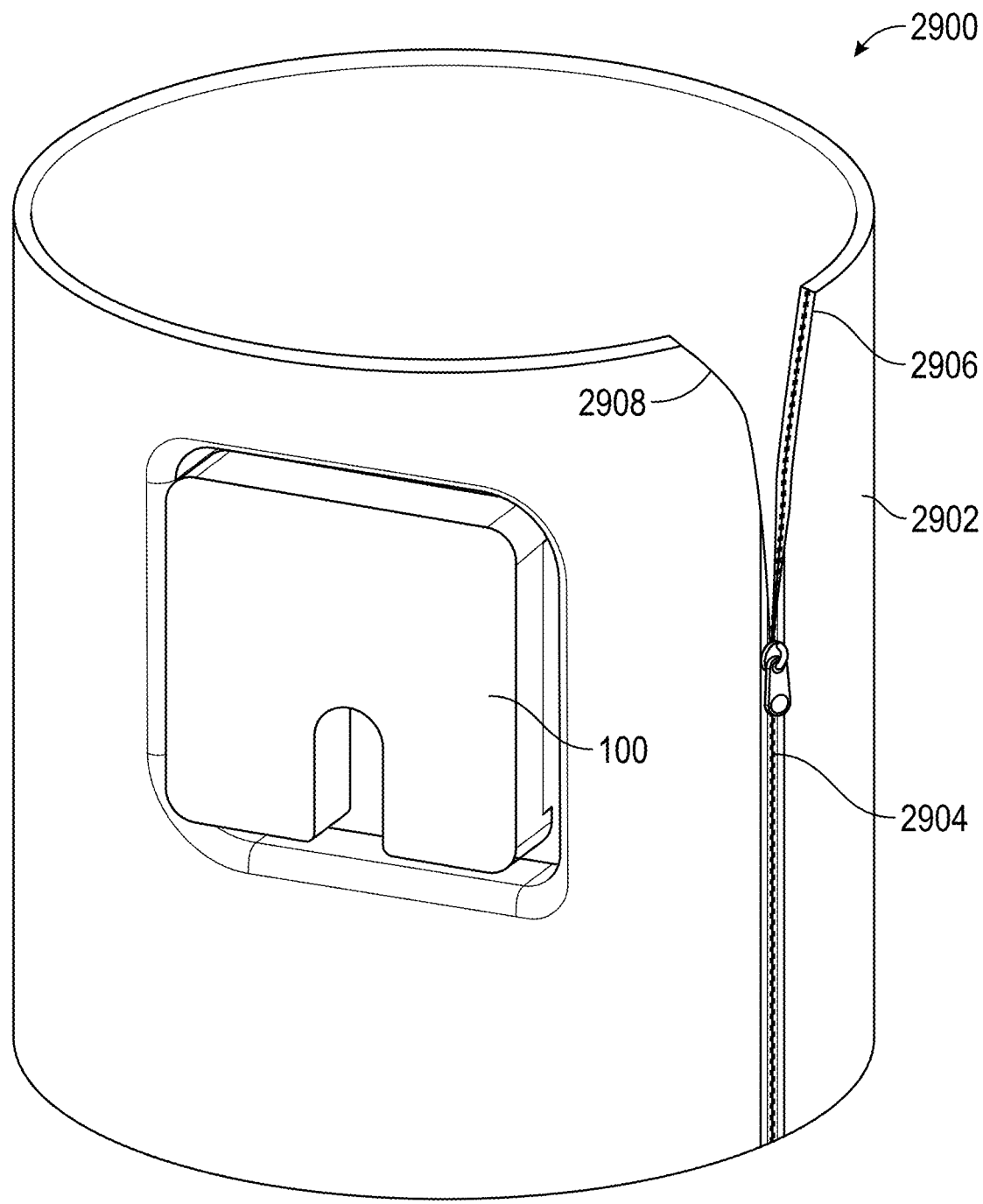
FIG. 29 illustrates a perspective view of a system comprising a supporting structure in the form of a cuff or a sleeve and an ultrasound device connected thereto, wherein the cuff or sleeve comprises a zipper, in accordance with an embodiment.

FIG. 29 illustrates a perspective view of a system 2900 comprising a supporting structure 2902 in the form of a cuff or a sleeve and an ultrasound device 100 connected thereto, wherein the cuff or sleeve comprises a zipper 2904. Zipper 2904 enables two free ends 2906 and 2908 of the cuff or sleeve to be connected together after supporting structure 2902 has been wrapped around an extremity or limb of a patient. Such a feature may provide form-fitting and secure attachment of supporting structure 2902 to the patient extremity or limb. In a further embodiment, supporting structure 2902 may further comprise an integrated lining that is disposed behind zipper 2904 such that when supporting structure 2902 is affixed to a patient, the lining is positioned on top of the skin and between zipper 2904 and the body of the patient, thereby ensuring that zipper 2904 cannot catch the skin of the patient. Although in the embodiment of FIG. 29, zipper 2904 performs the function of adjoining two free ends 2906 and 2908, it is noted that in other embodiments, still other closure means may be used to adjoin two free ends 2906 and 2908, including but not limited to clamps, clips, tabs, snaps, ties, zippers, Velcro, adhesives, or the like.

Figure 30:
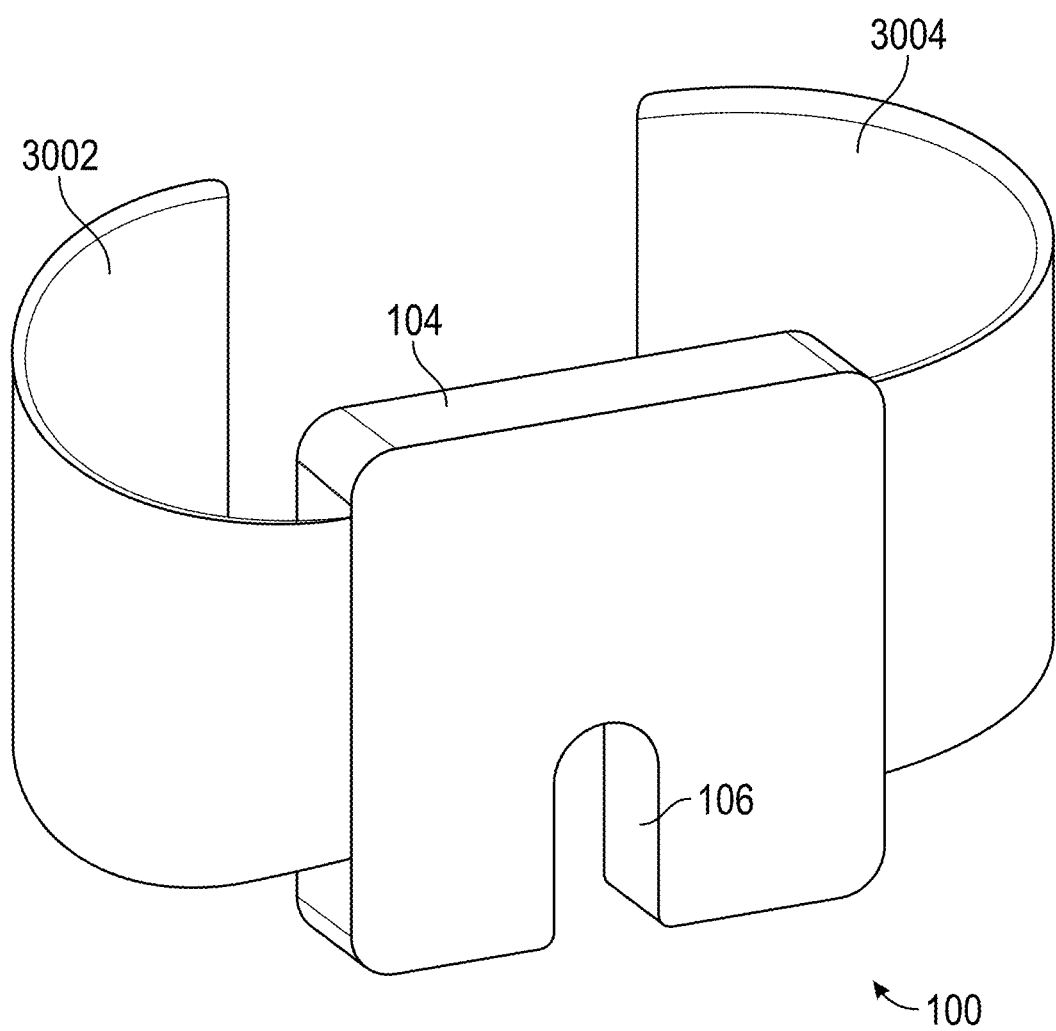
FIG. 30 illustrates a perspective view of an embodiment in which an ultrasound device comprises integrated first and second clamping arms for securing the ultrasound device to the anatomy of a patient in accordance with an embodiment.

FIG. 30 illustrates a perspective view of an embodiment in which ultrasound device 100 comprises an integrated first clamping arm 3002 that extends from a first side of ultrasound probe housing 104 and an integrated second clamping arm 3004 that extends from a second side thereof that is opposite to the first side. As shown in FIG. 30, the first side and the second side are to either side of the side of ultrasound probe housing 104 that includes guide channel cut-out or aperture 106, but it will be appreciated that any ultrasound device can be utilized in this supporting system and an internal guide channel cut-out or aperture 106 is not required. Taken together, ultrasound probe housing 104 and first and second clamping arms 3002 and 3004 form a C-shaped or U-shaped structure that can be secured to the anatomy of a patient receiving treatment. The embodiment of FIG. 30 may be particularly well suited, for example, for placing an IV or catheter in a portion of the anatomy such as in the neck or in the leg near the groin.

First clamping arm 3002 and second clamping arm 3004 may each comprise a rigid or semi-rigid material that may be secured to the anatomy of the patient at least by natural circumferential movement of the rigid/semi-rigid material as the two open/free ends of first clamping arm 3002 and second clamping arm 3004 will be pulled apart to attach to the patient extremity. Further, the embodiment of FIG. 30 may be secured to the patient anatomy by squeezing together two points that allows for ratcheting together of first clamping arm 3002 and second clamping arm 3004 using a mechanism such as, but not limited to, ratchet straps. The securing of the embodiment of FIG. 30 to the patient may also be carried out by compressing it in a circumferential or horizontal direction as desired.

In accordance with another embodiment, first and second clamping arms 3002 and 3004 are initially locked into an open position, in which the arms are separated to facilitate easy movement of ultrasound probe housing 104 relative to the anatomy of the patient. However, once the practitioner has located the desired landmark, a mechanism of ultrasound device 100 (e.g., tabs or other actuator) may be engaged which causes the arms to unlock and rotate to a closed position in which the arms are brought closer together, thereby causing ultrasound device 100 to be compressed around the body surface. First and second clamping arms 3002 and 3004 as well as ultrasound probe housing 104 may each comprise a disposable adhesive material on the body side or interior surface for additional attachment.

Although the embodiment of FIG. 30 does not allow for movement of ultrasound probe housing 104 relative to first and second clamping arms 3002 and 3004 since the arms are directly connected to the sides of ultrasound probe housing 104, it will be readily understood by persons skilled in the art that such movement could be achieved by combining the clamping features of the FIG. 30 embodiment with any of the supporting structures described herein that enable ultrasound device 100 to be moved within a recess or cavity thereof. In other words, a supporting structure that supports connection and unilateral or multilateral movement of ultrasound device 100 relative thereto could be modified to include first and second clamping arms such as first and second clamping arms 3002 and 3004. The FIG. 30 embodiment or any such alternate embodiments may be useful when placing central venous catheters to the internal jugular or femoral veins. A clamp-like supporting structure at the groin would allow for stability and the need to withstand some downward force from a possible abdominal pannus of an obese patient that needs to be lifted and retracted to gain access to the femoral vein/artery/nerve. An adhesive may be appropriate for the internal jugular approach, for instance, as it is an open and unencumbered area.

Figure 31:
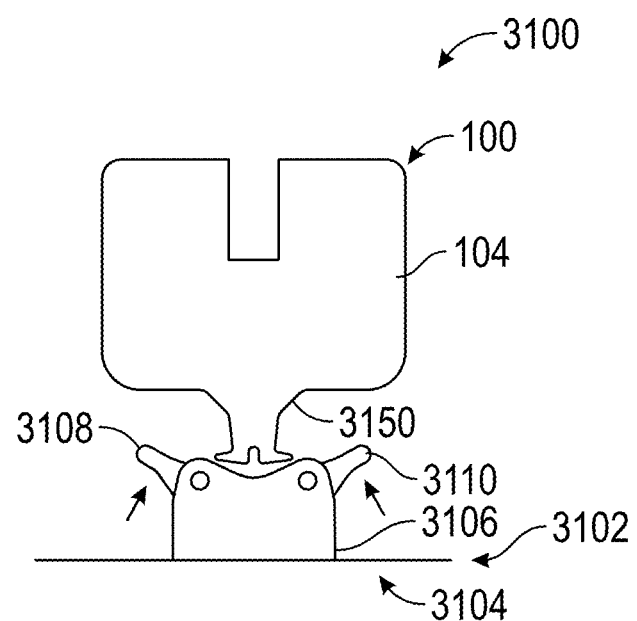
FIG. 31 illustrates a partial top perspective view of a system comprising a supporting structure and an ultrasound device, wherein the supporting structure comprises a body attachment portion and a release buckle integrated with a side thereof to enable the ultrasound device to be connected to the supporting structure in a position adjacent thereto in accordance with an embodiment.

FIG. 31 illustrates a partial top perspective view of a system 3100 comprising a supporting structure 3102 and ultrasound device 100, wherein supporting structure 3102 comprises a body attachment portion 3104 (e.g., a cuff, sleeve, C-clamp, U-clamp, or the like) and a release buckle 3106 integrated with a side thereof to enable ultrasound device 100 to be connected to supporting structure 3102 in a position adjacent thereto. This embodiment is intended to illustrate, in part, that ultrasound device 100 need not sit atop an associated supporting structure in order to be connected to a body of a patient, but that such connection may be achieved via attachment to a side of a supporting structure that is attached to the body of the patient, which may be beneficial for certain procedures.

In the embodiment of FIG. 31, ultrasound probe housing 104 comprises a connector 3150 that is configured to be inserted into release buckle 3106 thereby causing first and second release buckle tabs 3108 and 3110 to snap into a locked position and to cause ultrasound device 100 to become securely connected to release buckle 3106 and supporting structure 3102. Once connected, ultrasound probe 100 may be disconnected from supporting structure 3102 by simultaneously applying downward pressure to each of first and second release buckle tabs 3108 and 3110, which enables connector 3150 to be removed from release buckle 3106.

Although release buckle 3106 is largely visible in the embodiment shown in FIG. 31, in alternate embodiments some or all of release buckle 3106 may be embedded within an interior (e.g., a cavity) of body attachment portion 3104 of supporting structure 3102, in which case only a smaller portion of release buckle 3106 would be visible to a user. A wide variety of other connecting mechanisms or systems may be used to allow ultrasound device 100 to be selectively connected to and disconnected from supporting structure 3102, including but not limited to a snap connector. Such mechanisms may be formed from metal, plastic, or other suitable material. Furthermore, in alternate embodiments, ultrasound 100 may include a release buckle or snap connector integrated with ultrasound probe housing 104 and an associated supporting structure may include a specially-adapted connector that is configured to be inserted therein.

Figure 32:
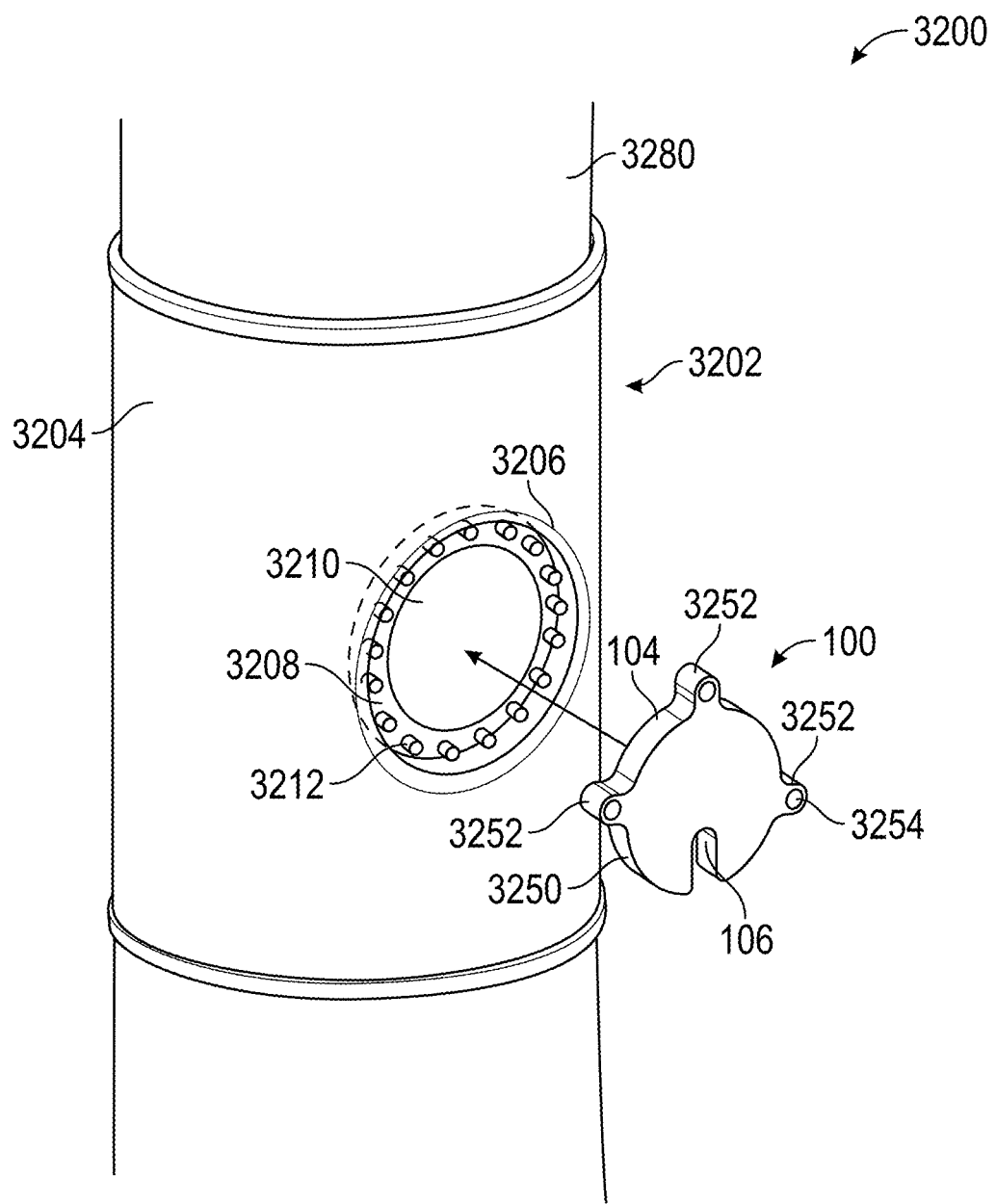
FIG. 32 illustrates a perspective view of a system comprising a disk-shaped ultrasound device having a plurality of mating members extending therefrom and a supporting structure having a recessed circular frame to which the ultrasound device may be attached in a variety of orientations in accordance with an embodiment.

FIG. 32 illustrates a perspective view of a system 3200 comprising an embodiment of ultrasound device 100 and a supporting structure 3202 to which ultrasound device 100 may be attached for an intended application. In FIG. 32, supporting structure 3202 is attached to an extremity 3280 (e.g., an arm) of a patient. Ultrasound device 100 is adapted to be connected to supporting structure 3202. In particular, as shown in FIG. 32, ultrasound device 100 comprises a substantially disk-shaped ultrasound probe housing 104 having a circumferential outer edge 3250 from which extends a number of mating members 3252, wherein each mating member 3252 comprises at least one female mating element 3254 (e.g. hole) that is adapted to mate with a corresponding male mating element 3212 (e.g. stud or peg) of supporting structure 3202, thereby facilitating a connection between ultrasound device 100 and supporting structure 3202. The number of female and male mating elements 3254 and 3212, respectively, can vary and need only be numerously sufficient to firmly affix ultrasound device 100 to supporting structure 3202 to perform the desired procedure.

In the embodiment of FIG. 32, supporting structure 3202 comprises a sleeve or cuff that is suitable for attachment to extremity 3280 (e.g., an arm) of the patient, although other devices suitable for attachment to a patient extremity may be used. Supporting structure 3202 comprises an ambient side 3204 having an outer surface within which is formed a recess 3206. Supporting structure 3202 also comprises a body side that is opposite ambient side 3204 and faces toward the body of the patient during use. Recess 3206 is adapted to accommodate insertion of at least a portion of ultrasound device 100 and itself comprises a rigid or semi-rigid recessed frame 3208 that surrounds an opening 3210 that passes fully through supporting structure 3202. Recessed frame 3208 supports a number of outward-facing male mating elements 3212 that are adapted to mate with corresponding female mating elements 3254 of ultrasound device 100.

By selectively aligning female mating elements 3254 of mating members 3252 of ultrasound device 100 with male mating elements 3212 of recessed frame 3208 and then at least partially inserting ultrasound device 100 into recess 3206, those mating elements can be caused to engage and ultrasound device 100 will become connected to supporting structure 3202. It should be appreciated that if mating elements 3254 and 3212 are compatible across each of mating members 3252 and recessed frame 3208, then ultrasound device 100 may be selectively and circumferentially rotated relative to guide channel cut-out or aperture 106 to provide access for needle 102 within needle guide assembly 108 or separately to a desired target site of the patient without repositioning supporting structure 3202.

Figure 33:
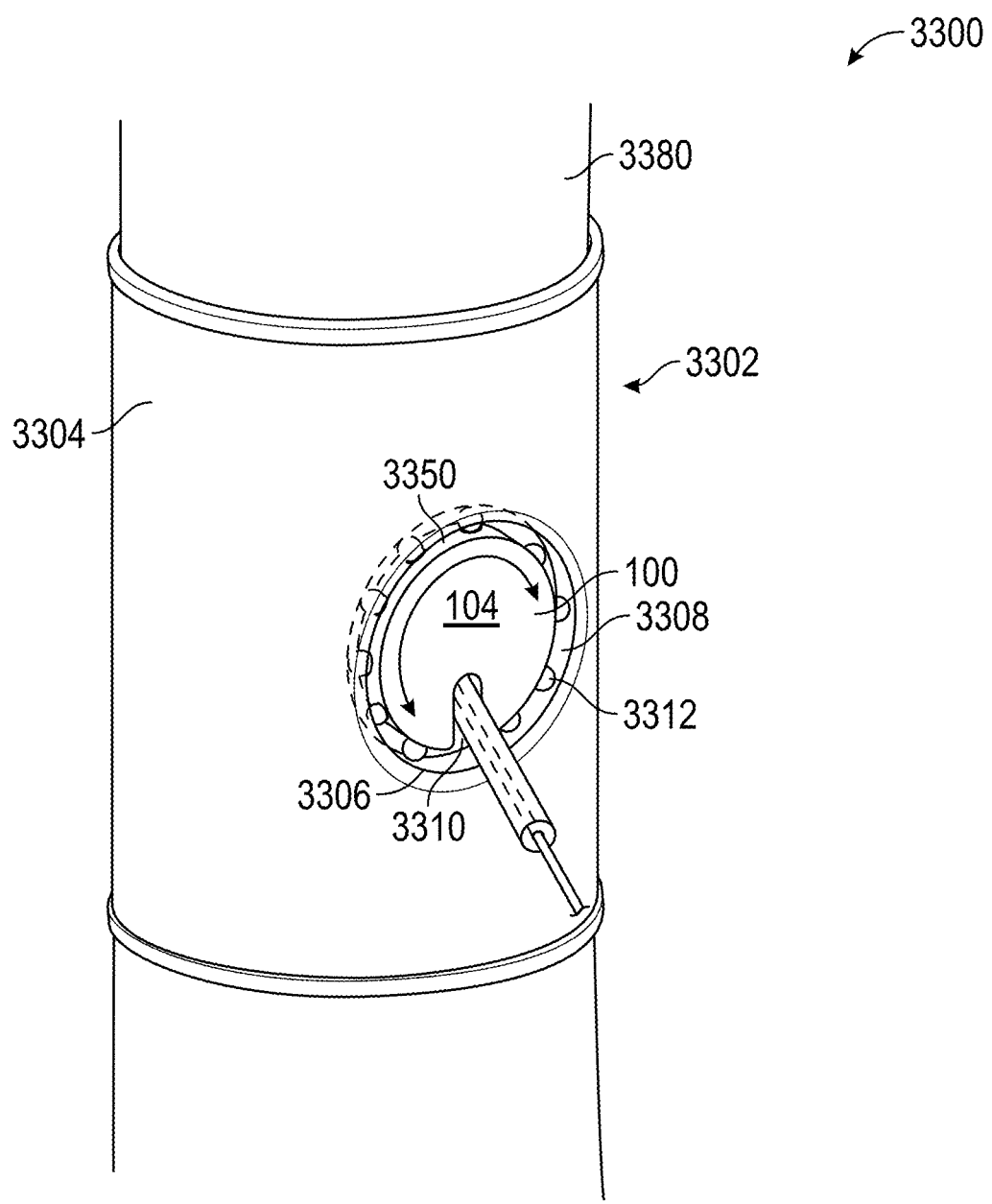
FIG. 33 illustrates a perspective view of a system comprising a disk-shaped ultrasound device and a supporting structure having a circular recess within which the ultrasound device is attached and wherein a plurality of ball bearings disposed between the ultrasound device and a wall of the recess enable the ultrasound device to be rotated within the recess in accordance with an embodiment.

FIG. 33 illustrates a perspective view of a system 3300 comprising an embodiment of ultrasound device 100 and a supporting structure 3302 to which ultrasound device 100 is attached for an intended application. In the embodiment of FIG. 33, supporting structure 3302 comprises a sleeve or cuff that is attached to an extremity 3380 (e.g., an arm) of a patient, although other devices suitable for attachment to a patient extremity may be used. Supporting structure 3302 comprises an ambient side 3304 having an outer surface within which is formed a circular recess 3306. Supporting structure 3302 also comprises a body side that is opposite ambient side 3304 and faces toward the body of the patient during use. Circular recess 3306 is adapted to accommodate insertion of at least a portion of ultrasound device 100 and itself comprises a circular sidewall 3308 which has a grooved or convex shape. Circular sidewall 3308 surrounds an opening 3310 that extends through supporting structure 3302 but which is largely obscured in FIG. 33 as it is disposed beneath the body side of ultrasound device 100.

As further shown in FIG. 33, ultrasound device 100 comprises a substantially disk-shaped ultrasound probe housing 104 that is at least partially inserted within circular recess 3306. Ultrasound probe housing 104 comprises a circumferential outer edge 3350 having a grooved or convex shape similar to that of circular sidewall 3308. In system 3300, grooved/convex circumferential outer edge 3350 of ultrasound probe housing 104 and grooved/convex circular sidewall 3308 of circular recess 3306 together form a tubular or cylindrical channel within which a plurality of ball bearings 3312 are disposed. Ball bearings 3312 serve both to secure ultrasound device 100 within circular recess 3306 as well as enable the circumferential rotation of ultrasound device 100 and associated guide channel cut-out or aperture 106 from 0 to 360 degrees within circular recess 3306. In an embodiment, when ultrasound device 100 has been rotated to a desired position, a locking mechanism may be engaged to hold ultrasound device 100 in the desired position. Any of a wide variety of locking mechanisms may be used for this purpose, including but not limited to locking tabs, tightening wing nuts at one or more positions, push and release button or pin, buckle latch, Velcro or other hook and loop tightening. Alternatively, ultrasound device 100 may be manually held in the desired position. In this manner, a variety of different insertion paths may be provided for needle 102 within needle guide assembly 108 without repositioning supporting structure 3302.

Figure 34:
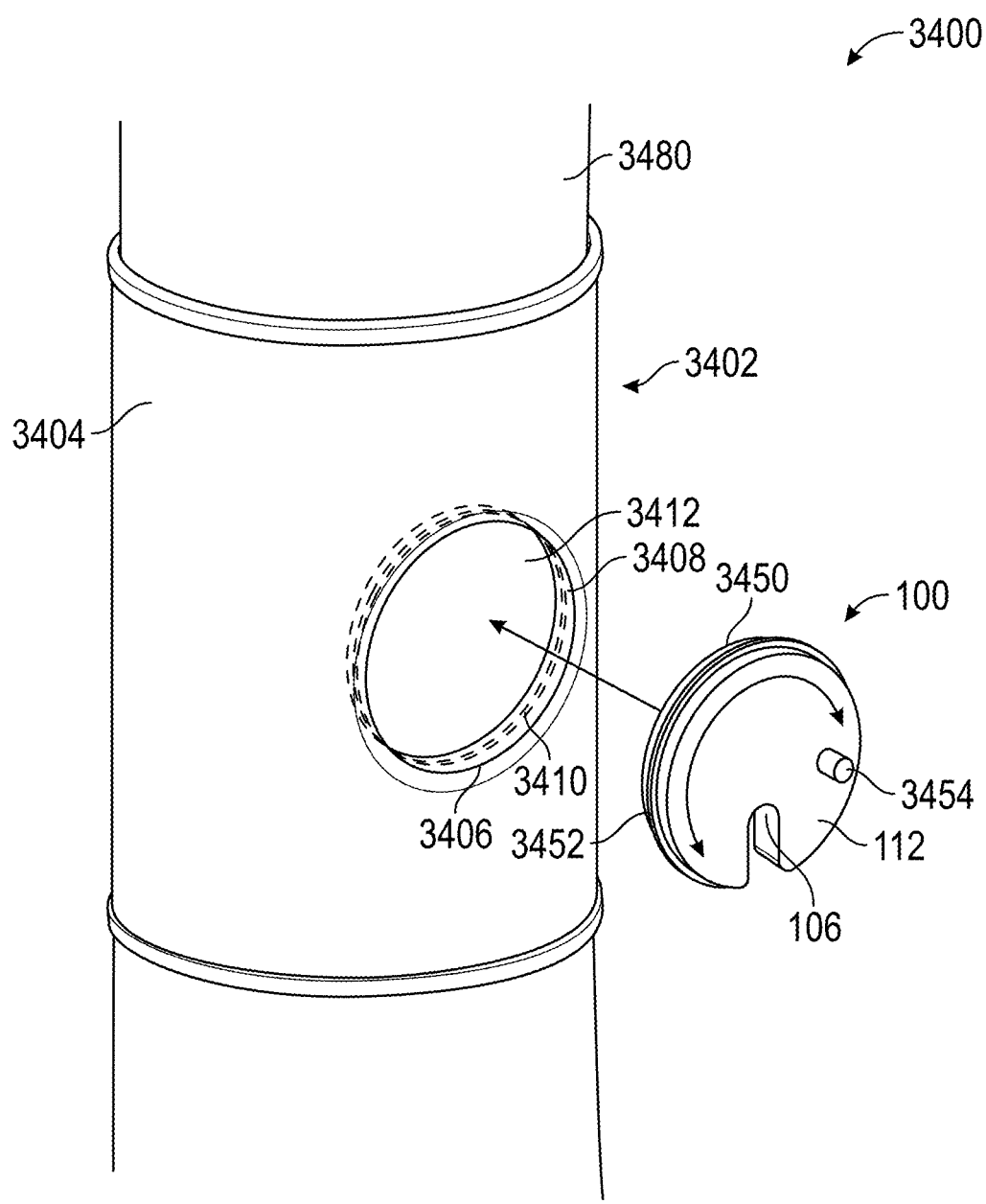
FIG. 34 illustrates a perspective view of a system comprising a disk-shaped ultrasound device having a rail on a circumferential outer edge thereof and a supporting structure having a circular recess with a sidewall groove in which the rail of the ultrasound device may be inserted to allow the ultrasound device to be rotatably connected to the supporting structure in accordance with an embodiment.

FIG. 34 illustrates a perspective view of a system 3400 comprising an embodiment of ultrasound device 100 and a supporting structure 3402 to which ultrasound device 100 is attached for an intended application. In the embodiment of FIG. 34, supporting structure 3402 comprises a sleeve or cuff that is attached to an extremity 3480 (e.g., an arm) of a patient, although other devices suitable for attachment to a patient extremity may be used. Supporting structure 3402 comprises an ambient side 3404 having an outer surface within which is formed a circular recess 3406. Supporting structure 3402 also comprises a body side that is opposite ambient side 3404 and faces toward the body of the patient during use. Circular recess 3406 is adapted to accommodate insertion of at least a portion of ultrasound device 100 and itself comprises a circular sidewall 3408 which has a groove 3410 formed therein. Circular sidewall 3408 surrounds an opening 3412 that that extends fully through supporting structure 3402.

As further shown in FIG. 34, ultrasound device 100 comprises a substantially disk-shaped ultrasound probe housing 104 that is configured to be at least partially inserted within circular recess 3406. Ultrasound probe housing 104 comprises a circumferential outer edge 3450 having a rail 3452 formed thereon. The insertion of rail 3452 of ultrasound device 100 into groove 3410 serves to connect ultrasound device 100 to supporting structure 3402. Furthermore, rail 3452 and groove 3410 are sized and shaped such that rail 3452 can slide within groove 3410, thereby enabling ultrasound device 100 to be circumferentially rotated within circular recess 3406 while connected to supporting structure 3402. It should be apparent that the location of rail 3452 and groove 3410 can be reversed with respect to the structure on which they reside. Rail 3452 may be placed on circular sidewall 3408 of supporting structure 3402 and groove 3410 may be formed on ultrasound probe housing 104. A handle 3454 that is connected to or integrated with ambient side 112 of ultrasound probe housing 104 may be used to facilitate such rotation. In an embodiment, when ultrasound device 100 has been rotated to a desired position, a locking mechanism may be engaged to hold ultrasound device 100 in the desired position. Any of a wide variety of locking mechanisms may be used for this purpose, including but not limited to locking tabs, tightening wing nuts at one or more positions, push and release button or pin, buckle latch, Velcro or other hook and loop tightening. Alternatively, ultrasound device 100 may be manually held in the desired position. In this manner, a variety of different insertion paths may be provided for needle 102 within needle guide assembly 108 without repositioning supporting structure 3402.

It can be seen in FIG. 34 that ultrasound probe housing 104 including rail 3452 is wider than recess 3406 which means that some mechanism must be implemented to snap rail 3452 into groove 3410. In an embodiment, this is achieved by implementing rail 3452 with a rigid or semi-rigid material that deforms slightly under pressure to accommodate insertion into recess 3406 but that will snap back into place after rail 3452 is aligned with groove 3410. In another embodiment, rail 3452 is configured to at least partially retract into ultrasound probe housing 104 under pressure thereby enabling ultrasound device 100 to be inserted into recess 3406, but is also biased (e.g., spring biased) so that it will snap outward into groove 3410 when aligned therewith. In another embodiment, supporting structure 3402 may open or enlarge to allow rail 3452 of ultrasound probe housing 104 to be inserted into recess 3406, after which supporting structure 3402 may then be closed or reduced in size, thereby securing ultrasound probe housing 104 in place. Still other techniques may be used to insert rail 3452 into groove 3410. In a still further embodiment, ultrasound device 100 may be pre-fitted (even permanently) within supporting structure 3402.

Figure 35:
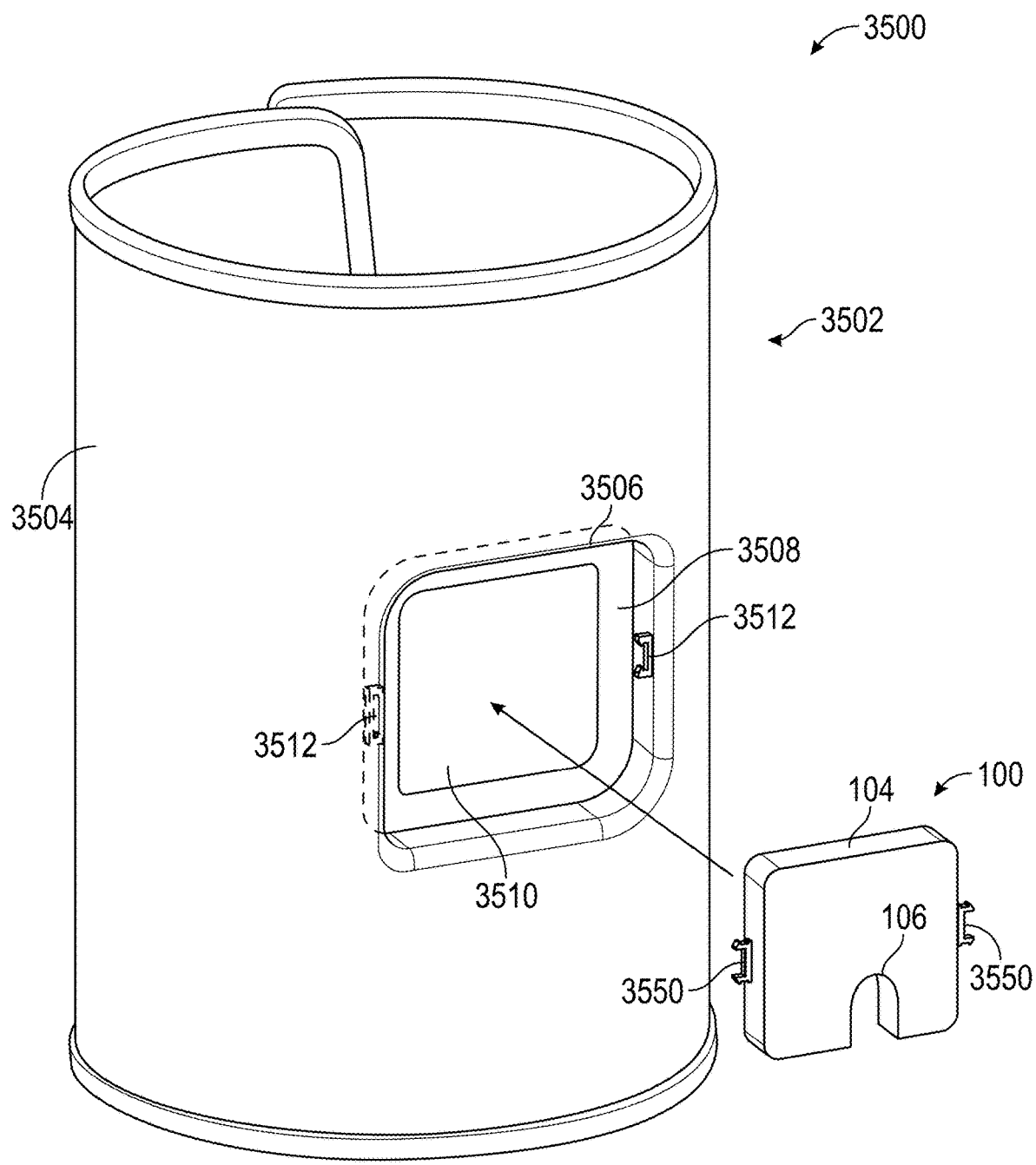
FIG. 35 illustrates a perspective view of a system comprising an ultrasound device with male snap connector elements and a supporting structure having a recess with female snap connector elements to which the ultrasound device may be attached in accordance with an embodiment.

FIG. 35 illustrates a perspective view of a system 3500 comprising an embodiment of ultrasound device 100 and a supporting structure 3502 to which ultrasound device 100 may be attached for an intended application. In the embodiment of FIG. 35, supporting structure 3502 comprises a sleeve or cuff that may be attached to an extremity (e.g., an arm) of a patient, although other devices suitable for attachment to a patient extremity may be used. Supporting structure 3502 comprises an ambient side 3504 having an outer surface within which is formed a recess 3506. Supporting structure 3502 also comprises a body side that is opposite ambient side 3504 and faces toward the body of the patient during use. Recess 3506 is adapted to accommodate insertion of at least a portion of ultrasound device 100 and itself comprises a rigid or semi-rigid recessed frame 3508 that surrounds an opening 3510 that passes fully through supporting structure 3502. Recess 3506 comprises four sidewalls, and female snap connectors 3512 are formed on or otherwise connected to two opposing ones of the four sidewalls.

As further shown in FIG. 35, ultrasound device 100 comprises ultrasound probe housing 104 having male snap connectors 3550 extending from two opposing sides thereof, wherein such opposing sides are to either side of the side of ultrasound probe housing 104 that includes guide channel cut-out or aperture 106. Each male snap connector 3550 is adapted to mate with a corresponding female snap connector 3512 of supporting structure 3502, thereby facilitating a connection between ultrasound device 100 and supporting structure 3502. Male snap connectors 3550 and female snap connectors 3512 may be configured such that ultrasound device 100 may be selectively connected in one of two different orientations-namely, a first orientation in which guide channel cut-out or aperture 106 is facing down within recess 3506 and a second orientation in which guide channel cut-out or aperture 106 is facing up within recess 3506. In an alternate embodiment, each of the four sidewalls of recess 3506 may have a female snap connector 3512 formed thereon or otherwise connected thereto, thereby enabling ultrasound device 100 to be selectively connected within recess 3506 in one of four different orientations, such that guide channel cut-out or aperture 106 is facing one of down, up, left, or right within recess 3506. In this manner, a variety of different insertion paths may be provided for needle 102 within needle guide assembly 108 without repositioning supporting structure 3502. It is noted that, in alternate embodiments, male snap connectors may be formed on the sidewalls of recess 3506 and female snap connectors may be formed on opposing sides of ultrasound probe housing 104.

Figure 36:
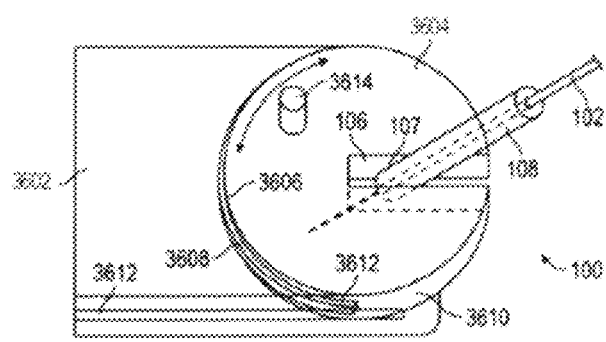
FIG. 36 illustrates a perspective view of an ultrasound device having an ultrasound probe housing that comprises a stationary housing component and a rotational housing component that is connected thereto in accordance with an embodiment.

FIG. 36 illustrates a perspective view of an embodiment of ultrasound device 100 in which ultrasound probe housing 104 comprises a stationary housing component 3602 and a rotational housing component 3604 that is connected thereto. As shown in FIG. 36, stationary housing component 3602 has an ambient side (visible in FIG. 36) and a body side (obscured in FIG. 36). As also shown in FIG. 36, rotational housing component 3604 is generally disk-shaped, having a circular ambient side (visible in FIG. 36) connected to a circular body side (obscured in FIG. 36) by a circumferential outer edge 3610. Rotational housing component 3604 includes guide channel cut-out or aperture 106 within which is disposed needle guide assembly 108 that receives needle 102 as previously described. Ultrasound probe housing 104 further comprises a mechanism that enables rotational housing component 3604 to be circumferentially rotated with respect to stationary housing component 3602 while connected thereto. For example, stationary housing component 3602 may comprise a semicircular outer edge 3606 within which is formed a semicircular channel 3608. Circumferential outer edge 3610 of rotational housing component 3604 may comprise a semicircular rail 3612. Semicircular rail 3612 may be configured to be inserted within semicircular channel 3608 in an interlocking manner and may further be configured to be slidably moveable within semicircular channel 3608, thereby enabling the circumferential rotation of rotational housing component 3604 while connected to stationary housing component 3602. In an alternate embodiment, semicircular rail 3612 may reside on stationary housing component 3602 and semicircular channel 3608 may reside on rotational housing component 3604.

Rotational housing component 3604 may further comprise a handle 3614 connected to or otherwise integrated with the ambient side thereof to facilitate manual rotation by a user. In accordance with such an embodiment, ultrasound probes 105 disposed within ultrasound probe housing 104 may be housed in stationary component 3602, rotational component 3604, or distributed among both components.

As further shown in FIG. 36, stationary housing component 3602 may comprise one or more attachment features 3612 that facilitate slidable connection of ultrasound device 100 to a supporting structure, such as a cuff, sleeve, C-clamp, U-clamp, etc., as described herein, wherein the supporting structure may be affixed to a patient needing a procedure. In FIG. 36, attachment features 3612 are guides formed in opposite edges of stationary housing component 3602 that are configured to receive rails of the supporting structure, but it will be appreciated that the attachment features may likewise comprise rails formed on opposite edges of stationary housing component 3602 that are configured to be inserted in guides of the supporting structure, as well as rollers, bearings or other flexible/slidable connection points. Such an embodiment advantageously allows ultrasound device 100 to be moved laterally with respect to the supporting structure while connected thereto, while also enabling circumferential rotation of rotatable housing component 3604 (and guide channel cut-out or aperture 106) while connected to the supporting structure. A first locking mechanism may be provided to lock stationary housing component 3602 in a desired position with respect to the supporting structure while a second locking mechanism may be provided to lock rotational housing component in a desired rotational position with respect to stationary housing component 3602. Once a desired configuration has been achieved, needle guide assembly 108 further allows for horizontal movement of needle 102 about pivot point 110 as the target site has been located and shallow insertion is required in order to perform the procedure. It should be apparent that the supporting structure can be any form disclosed herein appropriate for the procedure to be performed. It will further be appreciated that the location of pivot point 110 to which needle guide assembly 108 is connected can be located at different locations along and within guide channel cut-out or aperture 106 and that its location may impact viewing and movement of needle 102. FIG. 36 shows needle pivot point 110 near the innermost wall of guide channel cut-out or aperture 106 for instance, but it may be placed differently within the guide channel cut-out or aperture 106.

Figure 37:
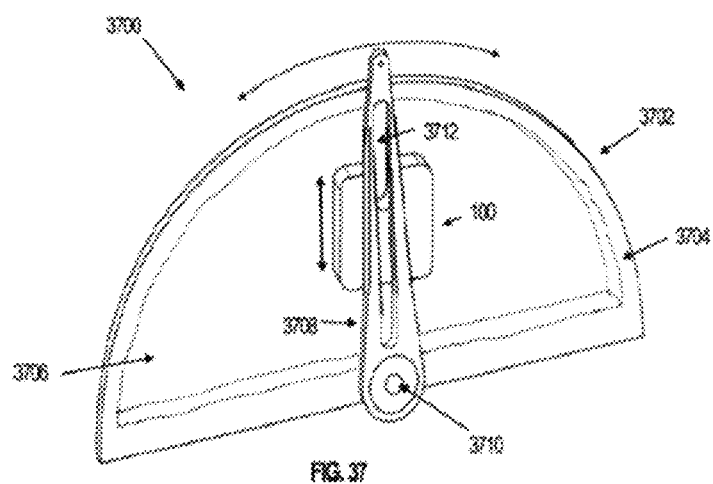
FIG. 37 illustrates a perspective view of a system comprising an ultrasound device and a supporting structure having a rotatable arm to which the ultrasound device may be slidably attached in accordance with an embodiment.

FIG. 37 illustrates a perspective view of a system 3700 comprising an embodiment of ultrasound device 100 and a supporting structure 3702 to which ultrasound device 100 may be attached for an intended application. In the embodiment of FIG. 37, supporting structure 3702 comprises an ambient side 3704 having an outer surface within which is formed a semicircular opening 3706 that passes fully through supporting structure 3702. Supporting structure 3702 also comprises a body side that is opposite ambient side 3704 and faces toward the body of the patient during use. Supporting structure 3702 further comprises an arm 3708 that is attached to a pivot point 3710 formed on the outer surface of ambient side 3704. Pivot point 3710 may be located substantially midway along a diameter of semicircular aperture 3706. Arm 3708 is configured to be manually or automatically rotated about pivot point 3710 such that arm 3708 may be rotated over semicircular opening 3706 substantially from one end thereof to the other as desired. Arm 3708 itself comprises an elongated opening 3712 that extends a portion (e.g., a significant portion) of the length thereof and that passes fully therethrough.

Although not shown in FIG. 37, a bottom surface of arm 3708 comprises one or more attachment features that enable ultrasound device 100 to be slidably attached thereto. For example, one or more rails extending from ultrasound probe housing 104 may be configured to engage with one or more corresponding grooves formed in the bottom surface of arm 3708, or vice versa. Still other mechanisms may be used to enable ultrasound device 100 to be slidably attached to arm 3708. As shown in FIG. 37, when ultrasound device 100 is attached to arm 3708, guide channel cut-out or aperture 106 is aligned such that at least a portion thereof will be located directly below elongated opening 3712 even as ultrasound device 100 is moved up and down arm 3708, thereby ensuring that arm 3708 does not impede access to guide channel cut-out or aperture 106. Thus, in accordance with the embodiment of FIG. 37, through both the rotation of arm 3708 over semicircular aperture 3706 and the sliding of ultrasound device 100 up and down arm 3708, a practitioner is enabled to select from among a number of positions and orientations for needle insertion within semicircular opening 3706. It is to be understood that supporting structure 3702 of FIG. 37 may itself be integrated another type of support structures, such as a cuff, a sleeve, a C-clamp, a U-clamp, or the like.

Figure 38:
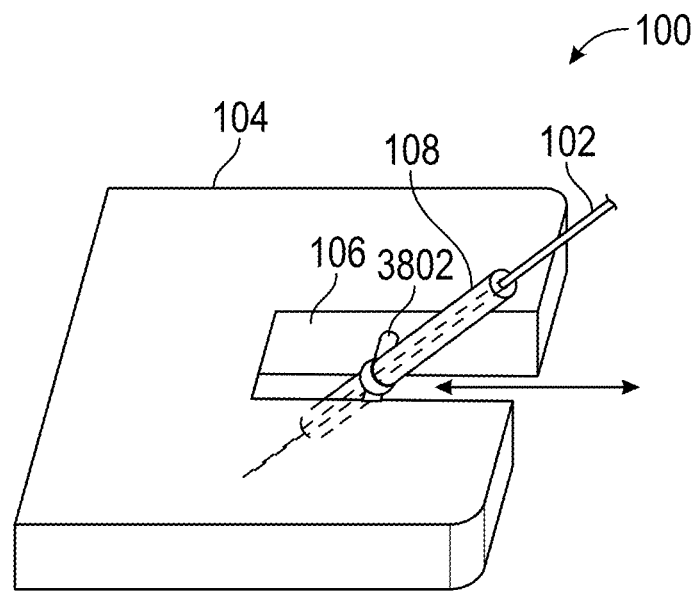
FIG. 38 illustrates a perspective view of an ultrasound device having an ultrasound probe housing that includes a guide channel cut-out or aperture and a lateral movement component for a needle guide assembly within the guide channel cut-out or aperture in accordance with an embodiment.
Figure 39:
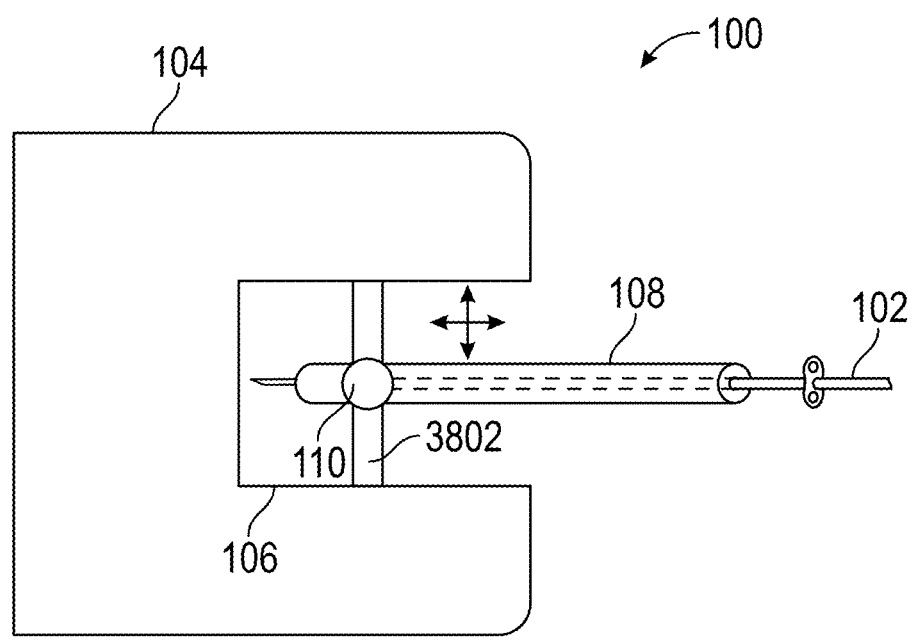
FIG. 39 illustrates a top view of the ultrasound device of FIG. 38.

FIG. 38 illustrates a perspective view of an embodiment of ultrasound device 100 in which a lateral movement component is disposed within guide channel cut-out or aperture 106 of ultrasound probe housing 104. FIG. 39 illustrates a top view of the same embodiment. In this embodiment, needle guide assembly 108 connects to and moves on a movement bar 3802 situated within guide channel cut-out or aperture 106 to allow the operator's desired movement of needle guide assembly. Movement bar 3802 may be perpendicularly situated to needle guide assembly 108. Needle guide assembly pivot point 110 may be located on or near movement bar 3802. The presence of movement bar 3802 allows the full range of motion required of needle guide assembly 108 to perform the intended procedure. A locking component may also be provided to fix needle guide assembly 108 for a procedure once the desired location has been identified. It will be appreciated that ultrasound probe housing 104 may contain ultrasound probes for viewing and tracking needle 102 upon entry. The placement of movement bar 3802 may widen guide channel cut-out or aperture 106 such that it may also create a direct operator viewable region within ultrasound device 100 to further facilitate the procedure to be performed.

Figure 40:
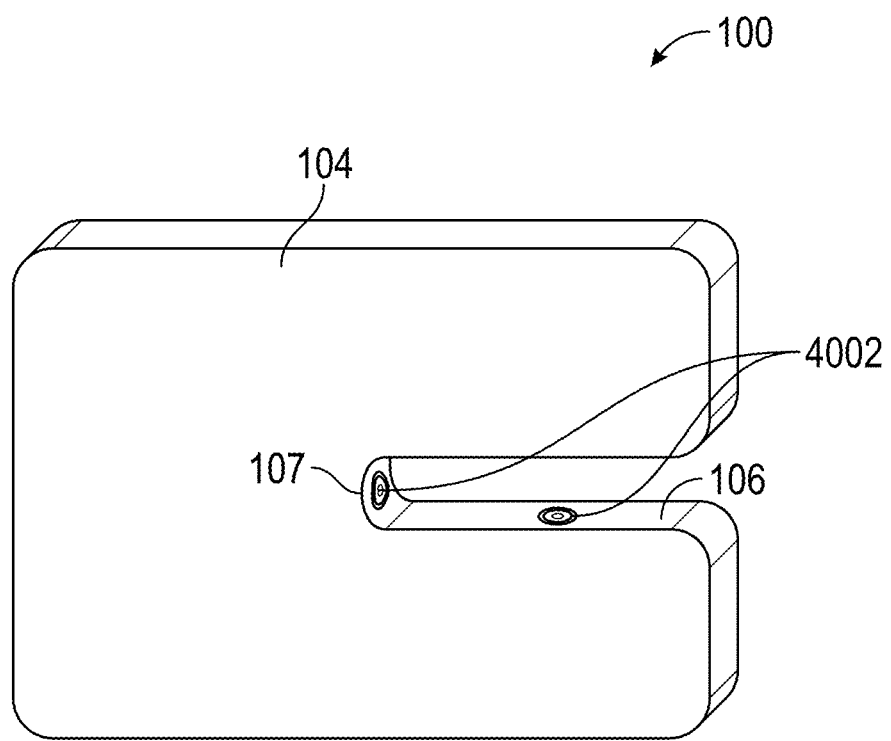
FIG. 40 illustrates a perspective view of an embodiment of an ultrasound device that includes one or more imaging devices within an ultrasound probe housing thereof to enable tracking of needle movement prior to entry into a patient.

FIG. 40 illustrates a perspective view of an embodiment of ultrasound device 100 that includes a plurality of imaging devices 4002 within ultrasound probe housing 104. The inclusion of imaging devices 4002 advantageously enables tracking of needle 102 movement prior to entry thereof into the patient. Each imaging device 4002 may comprise, for example, a camera. In an embodiment in which imaging device 4002 comprises a camera, the camera may comprise for example and without limitation a digital camera, an analog camera, a fiber optic camera, a visible light camera, an infrared camera, etc. Image data collected by each imaging device 4002 may be transmitted to a computing device to which ultrasound device 100 is communicatively connected (e.g., a computing device that includes processor 602, memory unit 604, and data interface 606 as shown in FIG. 6) for rendering to a display unit (e.g., display unit 610) viewable by a practitioner. Image data collected by each imaging device 4002 may also be sent to one or more computing devices to facilitate computer-guided procedures in accordance with certain embodiments.

Imaging devices 4002 of ultrasound device 100 can be used to provide an operator and/or computing device with an additional perspective of needle 102 location above the skin just prior to entry into the skin. For example, images of a procedure captured by imaging devices 4002 may be visualized in real time on a same display device that is used to display ultrasound images (e.g., display unit 610), on a display device that is co-located therewith, or on an external viewing device located remotely, for example, when an automated procedure is performed. This enables an operator to rely exclusively on the visualization of the procedure on the display device(s) before, during and after needle insertion if desired, rather than having to switch focus from the patient's body (before/during needle insertion) to the monitor (after needle insertion).

In addition to providing a visualization that is helpful for guiding needle insertion, image data collected by imaging devices 4002 may be analyzed (e.g., by processor 602) to measure and monitor certain parameters during the course of a procedure such as but not limited to a current angle of rotation, location, or direction of needle 102. The image data and/or the values derived therefrom may be presented to the user and/or used by embodiments in determining and visualizing a predicted path of needle 102. For example, the image data and/or the values derived therefrom may be used as input to an algorithm that predicts where needle 102 will be even for the first few millimeters of entry into the patient. The image data and/or the values derived therefrom may also be used by embodiments to determine manual and/or automatic adjustments to be made to the angle of rotation, location, or direction of needle 102 to follow a desired path or perform a given procedure.

The foregoing features relating to the inclusion of imaging devices 4002 in ultrasound probe housing 104 may be particularly useful in scenarios in which there is a blind spot for ultrasound probes 105 upon entry of needle 102 into the skin, in which case the images captured by imaging devices 4002 can be used to help compensate for such blind spot. Furthermore, it is likely that the skin of a patient will be depressed in practice when needle 102 is applied to the skin but before needle 102 punctures the skin's surface. Imaging devices 4002 could advantageously capture that depression even in cases where ultrasound probes 105 cannot.

In FIG. 40, imaging devices 4002 are shown as being located within guide channel cut-out or aperture 106 on ultrasound probe housing 104. However, it is to be understood that imaging devices 4002 may be disposed anywhere within and/or on ultrasound probe housing 104 that provides imaging device 4002 with a view of the expected site of penetration by needle 102 into the body of the patient. Furthermore, although two imaging devices 4002 are shown as being included in ultrasound probe housing in FIG. 40, alternative embodiments may include only a single imaging device 4002 or three or more imaging devices 4002.

Figure 41:
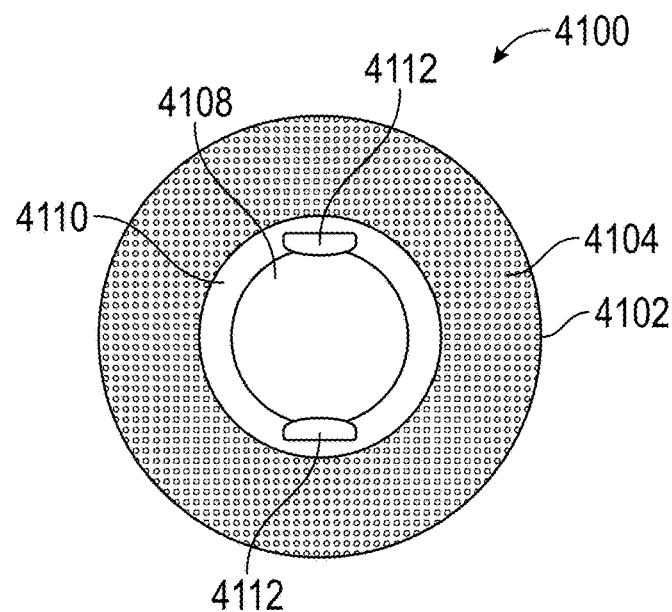
FIG. 41 illustrates a top perspective view of a supporting structure that may be adhesively attached to a body of a patient and to which an ultrasound device may be attached, in accordance with an embodiment.
Figure 42:
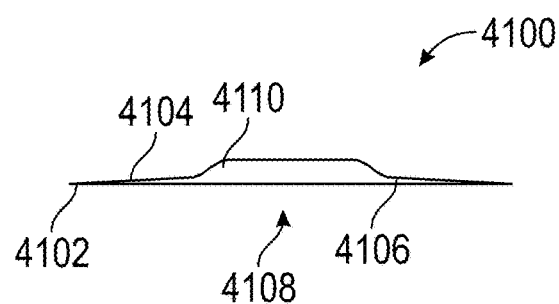
FIG. 42 illustrates a side perspective view of the supporting structure of FIG. 41.

FIG. 41 illustrates a top perspective view of a supporting structure 4100 that may be adhesively attached to a patient and to which an embodiment of ultrasound device 100 may be attached, in accordance with an embodiment. FIG. 42 illustrates a side perspective view of supporting structure 4100 of FIG. 41. Supporting structure 4100 comprises a layer of flexible or semi-flexible material 4102 having an ambient side 4104 and a body side 4106 and in which is formed an opening 4108 that passes fully therethrough. Layer 4102 may be formed from any suitable flexible or semi-flexible material such as plastic (e.g., PVC, polyethylene, acrylic, polyurethane, etc.), latex, silicone, or woven or non-woven fabrics (e.g., polyester, rayon, nylon, spandex, cotton, etc.), and may be antimicrobial in nature or contain applied antimicrobials, although these are examples only and are not intended to be limiting. An adhesive material is disposed across some or all of body side 4106 of layer 4102. The adhesive material may comprise acrylate or methacrylate or other vinyl resins, although these are examples only and are not intended to be limiting. Such adhesive material renders body side 4106 of layer 4102 sticky and thus suitable for secure attachment to the skin of a patient. Although not shown in FIGS. 41 and 42, supporting structure 4100 may further comprise a removable backing layer that is disposed over body side 4106 of layer 4102 and that may be removed immediately prior to use to expose the adhesive surface beneath. In an embodiment, the removable backing layer comprises coated paper or plastic, although these examples are not intended to be limiting.

As further shown in FIGS. 41 and 42, supporting structure 4100 further comprises a support frame 4110 that is attached to ambient side 4104 of layer 4102 and surrounds the edge of opening 4108. Support frame 4110 comprises a plurality of tabs 4112, each of which contains a magnetic mating element, and which are used to connect an embodiment of ultrasound device 100 to supporting structure 4100. For example, in an embodiment, ultrasound probe housing 104 comprises one or more magnetic mating elements that can be aligned with and attracted to the magnetic mating elements disposed within tabs 4112. When body side 114 of ultrasound probe housing 104 is brought sufficiently close to support frame 4110 and when the corresponding magnetic mating elements are properly aligned, ultrasound device 100 will become magnetically connected to supporting structure 4100.

The magnetic connection may be a magnet-to-magnet connection or a magnet-to-metal connection if the metal is a ferromagnetic metal. Consequently, the magnetic mating elements in tabs 4112 of support frame 4110 may comprise magnets, in which case the magnetic mating element(s) in ultrasound probe housing 104 may each comprise a magnet or a ferromagnetic metal. Furthermore, the magnetic mating elements in tabs 4112 may comprise a ferromagnetic metal, in which case the magnetic mating element(s) in ultrasound probe housing 104 may each comprise a magnet.

In the embodiment of FIGS. 41 and 42, both opening 4108 and support frame 4110 are circularly shaped. In an embodiment, ultrasound probe housing 104 may be shaped and sized such that all or some portion of ultrasound probe housing 104 aligns with circular support frame 4110. In accordance with such an embodiment, ultrasound probe housing 104 may be wholly or partially inset within hole 4108 and may further contain an internal guide channel cut-out or aperture 106 that allows access to the body of the patient through hole 4108. In further accordance with such an embodiment, the magnetic mating element(s) of ultrasound probe housing 104 may be disposed along the bottom edge such that different magnetic mating elements(s) of ultrasound probe 104 may be mated with the magnetic mating elements of tabs 4112. Alternatively, the magnetic mating element(s) of ultrasound probe housing 104 may comprise a magnet or ferromagnetic material that extends therefrom, for example, in the form of a tab, a wing, or other suitable structure. Such arrangements enable ultrasound device 100 to be circumferentially rotated and then magnetically mated to supporting structure 4100 in a variety of different orientations.

It is noted that in any of the aforementioned embodiments in which ultrasound device 100 is removably attached to a supporting structure using interlocking mating elements such as male and female connectors (e.g., studs and holes, snap connectors, etc.), that such embodiments may instead using magnetic mating elements such as those described above in reference to FIGS. 41 and 42 to implement the removable connection between ultrasound device 100 and the corresponding supporting structure.

Figure 43:
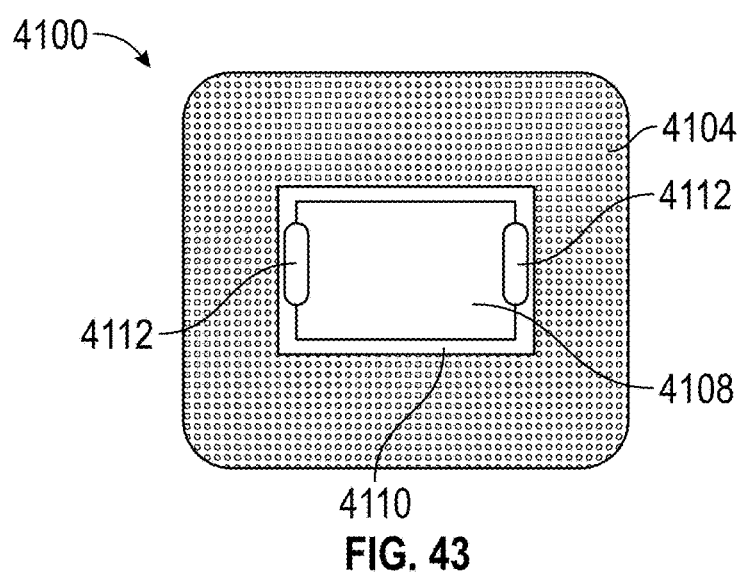
FIG. 43 illustrates a top perspective view of an alternate embodiment of the supporting structure of FIG. 41.

FIG. 43 illustrates a top perspective view of an alternate embodiment of supporting structure 4100 in which opening 4108 and support frame 4110 are rectangularly shaped and in which tabs 4112 contain magnetic mating elements and are arranged on opposite sides of opening 4108. In accordance with this embodiment, ultrasound device 100 may comprise one or more magnetic mating elements disposed within ultrasound probe housing 104 that are alignable with and attracted to the magnetic mating elements of tabs 4112, thereby enabling ultrasound device 100 to be magnetically connected to supporting structure 4100. It should be appreciated that while, for example, FIG. 43 provides a rectangular opening for access to the patient and FIG. 41 provides a circular opening for access to the patient, these shapes are exemplary and any shape that can accommodate access suffices within the scope of the disclosures contained herein.

Figure 44:
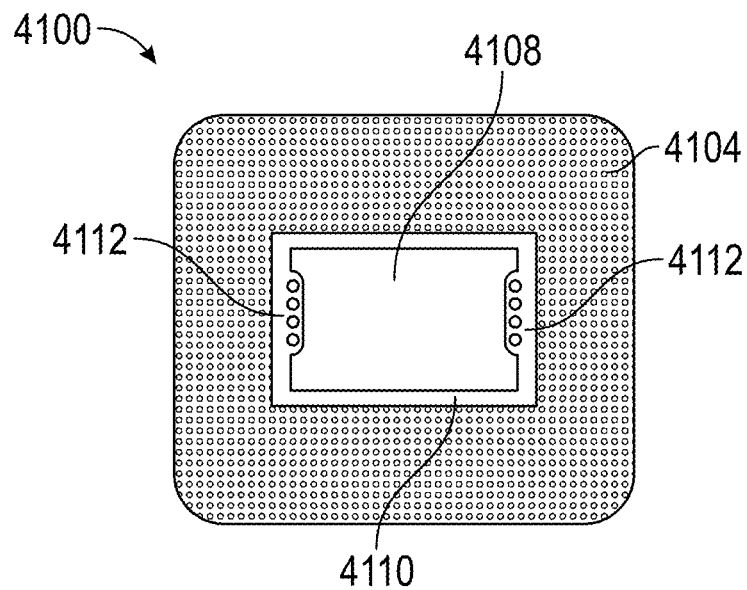
FIG. 44 illustrates a top perspective view of a further alternate embodiment of the supporting structure of FIG. 41.

FIG. 44 illustrates a top perspective view of yet another embodiment of supporting structure 4100 in which opening 4108 and support frame 4110 are rectangularly shaped and in which tabs 4112 contain male or female mating elements and are arranged on opposite sides of opening 4108. In accordance with this embodiment, ultrasound probe housing 104 of ultrasound device 100 may comprise female or male mating elements that are alignable with and mateable to corresponding male or female mating elements of tabs 4112, thereby enabling ultrasound device 100 to be connected to supporting structure 4100.

Adhesive supporting structure 4100 shown in FIGS. 41-44 may be attached to a wide variety of body locations so long as there is sufficient surface area upon which to attach the adhesive side of layer 4102. Thus, adhesive supporting structure 4100 provides a versatile way to secure ultrasound device 100 to different parts of the patient anatomy.

Adhesive supporting structure 4100 may be sized to accommodate ultrasound devices of varying sizes. For example, a supporting structure 4100 with a relatively small support frame 4110 may be useful for certain procedures where smaller, more compact, and lighter ultrasound devices are sufficient, such as with venous puncture or other shallow application procedures. However, supporting structure 4100 may also be of a relatively larger size to support a larger, more powerful ultrasound device, perhaps for use in procedures where greater resolving power may be desired, e.g., with lumbar puncture.

In an embodiment, supporting structure 4100 comprises a pre-sterilized disposable component manufactured from relatively inexpensive materials. The pre-sterilized disposable component may be pre-packaged in a suitable packaging material that can be opened at time of use. In accordance with such an embodiment, when the procedure is completed, ultrasound device 100 may be disconnected from supporting structure 4100 and then supporting structure 4100 may be peeled off the patient and discarded.

In a further embodiment of supporting structure 4100, opening 4108 may be pre-loaded with a layer of ultrasound gel that is useful in creating uniform contact between the skin of the patient and the operating surface of ultrasound device 100 (i.e., body side 114 of ultrasound probe housing 104). In accordance with such an embodiment, the layer of ultrasound gel may be disposed between a removable backing layer that is disposed over the entire body side 4106 of layer 4102 and covers the bottom of opening 4108 and a removable top cover that is disposed over support frame 4110 on ambient side 4104 of layer 4102 such that it covers the top of opening 4108. In practice, prior to placing adhesive body side 4106 of layer 4102 onto the skin of the patient, the user can peel off the removable backing layer from body side 4106, which also uncovers the bottom of the gel layer disposed in opening 4108. Once body side 4106 of layer 4102 is adhered to the patient's skin, the user then removes the removable top cover that is disposed over support frame 4110 on ambient side 4104 of layer 4102 thereby exposing the ultrasound gel and enabling ultrasound device 100 to be attached to support frame 4110. In another embodiment, the pre-loaded ultrasound gel may contain a bottom and/or top cover that is separate from any other backing layer or top cover.

Figure 45:
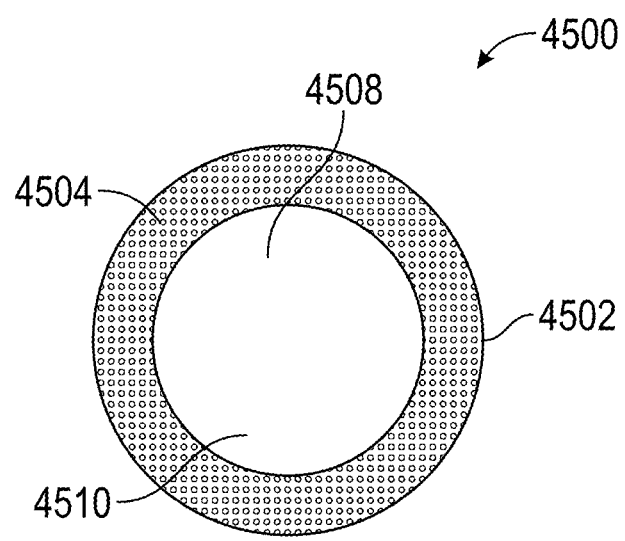
FIG. 45 illustrates a top perspective view of a supporting structure that may be adhesively attached to a body of a patient and that may be used to apply a layer of ultrasound gel thereto.

FIG. 45 illustrates a top perspective view of a structure 4500 that may be adhesively attached to a body of a patient and that may be used to provide a layer of ultrasound gel thereto in support of a procedure, in accordance with an embodiment. Structure 4500 comprises a layer of flexible or semi-flexible material 4502 having an ambient side 4504 and a body side (not visible in FIG. 45) and in which is formed an opening 4508 that passes fully therethrough. Layer 4502 may be formed from any suitable flexible or semi-flexible material such as plastic (e.g., PVC, polyethylene, acrylic, polyurethane, etc.), latex, silicone, or woven or non-woven fabrics (e.g., polyester, rayon, nylon, spandex, cotton, etc.), may be antimicrobial in nature or contain applied antimicrobials, and may otherwise be sterilizable, although these are examples only and are not intended to be limiting. An adhesive material is disposed across some or all of the body side of layer 4502. The adhesive material may comprise acrylate or methacrylate or other vinyl resins, although these are examples only and are not intended to be limiting. Such adhesive material renders the body side of layer 4502 sticky and thus suitable for secure attachment to the skin of a patient. Although not shown in FIG. 45, structure 4500 further comprises at least one removable backing layer that is disposed over the body side of layer 4502 and which may cover the bottom of opening 4508. The one or more removable backing layers are intended to be removed immediately prior to use. In an embodiment, the removable backing layer comprises coated paper or plastic, although these examples are not intended to be limiting.

As further shown in FIG. 45, supporting structure 4100 further comprises a layer of ultrasound gel 4510 (also referred to herein as "gel matrix 4510") that is disposed within opening 4108. Although not shown in FIG. 45, structure 4500 may further comprise a removable top cover that is disposed over ambient side 4504 of layer 4502 such that it fully covers opening 4508 and may, in certain embodiments, cover at least some portion of ambient side 4504 that surrounds opening 4508. The removable top cover may comprise coated paper or plastic, like the removable backing layer, or may be an appropriate but different material from the backing layer, although these examples are not intended to be limiting.

Prior to use, gel matrix 4510 has one or more cover layers, top and/or bottom, as it is contained in opening 4508. The cover layers may include a removable backing layer disposed on the body side of layer 4502 and the removable top cover disposed over ambient side 4504 of layer 4502. In practice, prior to placing the adhesive body side of layer 4502 onto the skin of the patient, the user peels off the removable backing layer from the body side of layer 4502, which may also uncover the bottom of gel matrix 4510 disposed in opening 4508 if gel matrix 4510 does not have a separate bottom cover layer. Gel matrix 4510 may have its own bottom cover layer independent from the removable backing layer, which may or may not be removed prior to use. Once the body side of layer 4502 is adhered to the patient's skin, the user then removes the removable top cover, if one is present, that is disposed over opening 4508 on ambient side 4504 of layer 4502 thereby exposing gel matrix 4510. Once gel matrix 4510 is in place on the body of the patient, the operational side of an ultrasound device of any type may then be applied to the body of the patient via the layer of ultrasound gel. In some embodiments, gel matrix 4510 of structure 4500 may not require one or both of the removable backing layer disposed on the body side of layer 4502 or the removable top cover on ambient side 4504. In some embodiments, gel matrix 4510 may utilize a backing layer that is intended to remain in place during usage of an ultrasound device without interfering with the operation of the device. Gel matrix 4510 may be comprised of any suitable ingredients, such water, propylene glycol, glycerin, phenoxyethanol, etc., such that it facilitates usage of an ultrasound device.

Adhesive structure 4500 shown in FIG. 45 may be attached to a wide variety of body locations so long as there is sufficient surface area upon which to attach the adhesive side of layer 4502. Adhesive structure 4500 may be formed in a variety of sizes to accommodate different types of procedures. In an embodiment, structure 4500 comprises a pre-sterilized disposable component manufactured from relatively inexpensive materials. The pre-sterilized disposable component may be pre-packaged in a suitable packaging material that can be opened at time of use. In accordance with such an embodiment, when the procedure is completed, structure 4500 may be peeled off the patient and discarded.

In any of the foregoing embodiments of FIGS. 41-45 in which ultrasound gel is pre-loaded into the opening of the supporting structure, a numbing agent may be included in the gel matrix. This may be deemed desirable, for example, if the procedure involves the insertion of a needle into the body of the patient via the gel matrix. The ability to numb the entry area can make the experience more pleasant for the patient. In accordance with such an embodiment, an active compound such as a numbing agent or other desired drug is included within the gel matrix.

Furthermore, in any of the foregoing embodiments of FIGS. 41-45 in which ultrasound gel is pre-loaded into the opening of supporting structure 4100 or structure 4500, a non-removable bio-safe layer (e.g., a bio-absorbable/resorbable layer, a biodegradable layer, or the like) may be provided that covers one or more surfaces of the gel matrix without interfering with the function of the gel itself. For example, a non-removable bio-safe layer may be provided that covers the side of the gel matrix that faces the patient. The presence of the non-removable bio-safe layer may better maintain the integrity of the ultrasound gel used, which could allow for a deeper gel layer or for use of a more or less viscous gel layer-both of which may be more desirable to the ultrasound operator. In practice, the non-removable bio-safe layer would stay in place and the practitioner or user would puncture it with the needle (e.g., needle 102) when the needle path is determined. Making this additional layer bio-safe may be deemed desirable because needle puncture may transfer a small portion of said layer into the patient.

In the foregoing description of various supporting structure embodiments, reference is made to an opening that passes fully the supporting structure (e.g., opening 1410, opening 2210, opening 2410, opening 2510, opening 2610, opening 3210, opening 3310, opening 3412, opening 2510, opening 3706, opening 4108 and opening 4508). In each of these embodiments, the opening is fully surrounded by the supporting structure. However, it is noted that in various alternate embodiments, the opening may only be partially surrounded by the supporting structure and open on one or more sides of the supporting structure. For example, the opening may comprise a cut-out formed in one or more sides of the supporting structure (similar, e.g., to how guide channel cut-out or aperture 106 may be a cut-out in one side of ultrasound device 100). Such a design may be deemed desirable, for example, to provide a practitioner with access to the body of the patient in an area that is immediately adjacent to ultrasound device 100.

II. Additional Exemplary Embodiments

A system is described herein. The system includes an ultrasound device and a supporting structure. The ultrasound device comprises an ultrasound probe housing that contains a plurality of ultrasound probes configured to generate ultrasound waves, wherein the ultrasound waves are configured to produce images of inside a body of a patient. The ultrasound probe housing comprising an ambient side and a body side. The supporting structure is configured to be attached to the body of a patient. The supporting structure comprises an ambient side and a body side. The supporting structure includes an opening that passes through the supporting structure from the ambient side to the body side thereof and one or more attachment features that are adapted to connect the ultrasound probe housing of the ultrasound device to the ambient side of the supporting structure such that at least a portion of the body side of the ultrasound probe is disposed within the opening and facing toward the body of the patient when the supporting structure is attached thereto.

In one embodiment of the foregoing system, the ultrasound device further comprises a guide channel cut out or aperture that passes through the ultrasound probe housing from the ambient side to the body side thereof and, when the ultrasound probe housing is connected to the ambient side of the supporting structure, at least a portion of the guide channel cut out or aperture is situated above the opening such that the needle is slidable within the needle guide assembly to enter the body of the patient via the opening. In further accordance with such an embodiment, the needle guide assembly may be connected to the guide channel cut-out or aperture at a pivot point within the guide channel cut-out or aperture and be rotatable within the guide channel cut-out or aperture and about the pivot point.

In another embodiment of the foregoing system, the supporting structure comprises one of a sleeve, a cuff, a C-clamp, a U-clamp, or an adhesive strip.

In yet another embodiment of the foregoing system, the one or more attachment features comprise: a male connector that is configured to mate with a female connector of the ultrasound probe housing; a female connector that is configured to mate with a male connector of the ultrasound probe housing; a first magnet that is configured to magnetically connect to a second magnet or a ferromagnetic metal component of the ultrasound probe housing; a ferromagnetic metal component that is configured to magnetically connect to a magnet of the ultrasound probe housing; a rail that is configured to engage with a groove of the ultrasound probe housing; a groove that is configured to engage with a rail of the ultrasound housing; a hook that is configured to mate with an eye of the ultrasound probe housing; an eye that is configured to mate with a hook of the ultrasound probe housing; or an attachment arm that is configured to engage with the ultrasound probe housing.

In a further embodiment of the foregoing system, the ambient side of the supporting structure comprises a recessed frame that surrounds the opening, the one or more attachment features comprise one or more first mating elements arranged on the recessed frame, and the ultrasound probe housing comprises at least one tab that extends from at least one edge thereof and includes one or more second mating elements that are configured to respectively mate with the one or more first mating elements.

In a still further embodiment of the foregoing system, the ambient side of the supporting structure comprises a rectangular recess that surrounds the opening, the one or more attachment features comprise grooves respectively formed in opposite sidewalls of the rectangular recess, the grooves being configured to receive corresponding rails that extend from opposite edges of the ultrasound probe housing, and the rails are slidable within the grooves to enable lateral movement of the ultrasound device within the recess while the ultrasound device is connected to the supporting structure.

In another embodiment of the foregoing system, the ambient side of the supporting structure comprises a rectangular recess that surrounds the opening, the one or more attachment features comprise rails respectively extending from opposite sidewalls of the rectangular recess, the rails being configured to engage with corresponding grooves that are formed in opposite edges of the ultrasound probe housing, and the grooves are slidable along the rails to enable lateral movement of the ultrasound device within the recess while the ultrasound device is connected to the supporting structure.

In yet another embodiment of the foregoing system, the ambient side of the supporting structure comprises a rectangular recess that surrounds the opening, the one or more attachment features comprise grooves respectively formed in opposite sidewalls of the rectangular recess, the grooves being configured to receive corresponding rails that extend from opposite edges of a frame to which the ultrasound probe housing is attached and in which the ultrasound probe housing is slidable in a first direction, and the rails are slidable within the grooves to enable movement of the frame within the recess in a second direction that is perpendicular to the first direction while the frame is connected to the supporting structure.

In still another embodiment of the foregoing system, the ambient side of the supporting structure comprises a rectangular recess that surrounds the opening, the one or more attachment features comprise rails respectively extending from opposite sidewalls of the rectangular recess, the rails being configured to engage with corresponding grooves that are formed in opposite edges of a frame to which the ultrasound probe housing is attached and in which the ultrasound probe housing is slidable in a first direction, and the grooves are slidable along the rails to enable movement of the frame within the recess in a second direction that is perpendicular to the first direction while the frame is connected to the supporting structure.

In a further embodiment of the foregoing system, the ambient side of the supporting structure comprises a recess that surrounds the opening and the one or more attachment features comprise a retractable attachment arm that extends from a sidewall of the recess.

In a still further embodiment of the foregoing system, the ambient side of the supporting structure comprises a recess that surrounds the opening and the one or more attachment features comprise a hook attached to or integrated with a sidewall of the recess, the hook being configured to engage with an eye attached to or integrated with an edge of the ultrasound probe housing.

In another embodiment of the foregoing system, the ambient side of the supporting structure comprises a recess that surrounds the opening and the one or more attachment features comprise a female snap connector attached to or integrated with a sidewall of the recess, the female snap connector being configured to engage with a male snap connector connected to or integrated with an edge of the ultrasound probe housing.

In still another embodiment of the foregoing system, the ambient side of the supporting structure comprises a recess that surrounds the opening and the one or more attachment features comprise a male snap connector attached to or integrated with a sidewall of the recess, the male snap connector being configured to engage with a female snap connector connected to or integrated with an edge of the ultrasound probe housing.

In yet another embodiment of the foregoing system, the supporting structure comprises a cuff or a sleeve and further comprises an integrated tourniquet. The integrated tourniquet may comprise a cord, tube or strap that is configured to be manually tightened around a limb of the patient. The integrated tourniquet may also comprise an inflatable tube, ring, or bladder.

In a further embodiment of the foregoing system, the supporting structure comprises a cuff or a sleeve having a closure means for adjoining two ends thereof around a limb of the patient.

In a still further embodiment of the foregoing system, the supporting structure comprises a circular recessed frame that surrounds the opening, the one or more attachment features comprise one or more first mating elements arranged on the circular recessed frame, and the ultrasound probe housing is substantially disk-shaped and comprises a circumferential outer edge from which extends one or more mating members comprising one or more second mating elements that are configured to respectively mate with the one or more first mating elements.

In another embodiment of the foregoing system, the ambient side of the supporting structure comprises a circular recess that surrounds the opening, the ultrasound probe housing is substantially disk-shaped, and the one or more attachment features comprise one or more ball bearings that are disposed between a circular sidewall of the circular recess and a circumferential outer edge of the ultrasound probe housing when the ultrasound probe housing is disposed within the circular recess, the one or more ball bearings being configured to enable circumferential rotation of the ultrasound device within the circular recess while the ultrasound device is connected to the supporting structure.

In yet another embodiment of the foregoing system, the ambient side of the supporting structure comprises a circular recess that surrounds the opening, the ultrasound probe housing is substantially disk-shaped, and the one or more attachment features comprise a groove that is formed in a circular sidewall of the circular recess, the groove being configured to receive a rail that extends from a circumferential outer edge of the ultrasound probe housing when the ultrasound probe housing is disposed within the circular recess, the rail being slidable within the groove to enable circumferential rotation of the ultrasound device within the circular recess while the ultrasound device is connected to the supporting structure.

In still another embodiment of the foregoing system, the ambient side of the supporting structure comprises a circular recess that surrounds the opening, the ultrasound probe housing is substantially disk-shaped, and the one or more attachment features comprise a rail that extends from a circular sidewall of the circular recess, the rail being configured to engage with a groove formed in a circumferential outer edge of the ultrasound probe housing when the ultrasound probe housing is disposed within the circular recess, the groove being slidable on the rail to enable circumferential rotation of the ultrasound device within the circular recess while the ultrasound device is connected to the supporting structure.

In a further embodiment of the foregoing system, the supporting structure further comprises a pivot point attached to the ambient side thereof and an arm that is rotatable about the pivot point and over the opening on the ambient side of the supporting structure, and the one or more attachment features are configured to attach the ultrasound probe housing to a bottom of the arm. In further accordance with such an embodiment, the one or more attachment features may be configured to slidably attach the ultrasound probe housing to the bottom of the arm, the arm may comprise an elongated opening that passes fully therethrough, and the ultrasound probe housing may comprise a guide channel cut-out or aperture that is aligned with the elongated opening when the ultrasound probe housing is slidably attached to the bottom of the arm such that at least a portion of the guide channel cut-out or aperture is located below the elongated opening as the ultrasound device is moved up and down the arm.

In a still further embodiment of the foregoing system, the supporting structure comprises a layer of flexible or semi-flexible material and an adhesive material disposed across at least a portion of the body side thereof to facilitate attachment to the body of the patient. In further accordance with such an embodiment, the supporting structure may further comprise a support frame attached to the ambient side thereof that surrounds the opening and includes the one or more attachment features. The system may further comprise a removable backing layer that is disposed over the body side of the supporting structure. The removable backing layer may be disposed over the body side of the supporting structure such that it covers a bottom of the opening, and the system may further comprise a layer of ultrasound gel disposed within the opening and a removable top cover that is disposed over the support frame on the ambient side of the supporting structure such that it covers a top of the opening. A numbing agent may be mixed with the layer of ultrasound gel. Also, a bio-safe layer may be disposed above or below the layer of ultrasound gel.

In a yet further embodiment of the foregoing system, the opening is fully surrounded by the supporting structure.

In another embodiment of the foregoing system, the opening is partially surrounded by the supporting structure.

A supporting structure configured to be attached to a body of a patient is also described herein. The support structure comprises: an ambient side, a body side opposite the ambient side, an opening that passes through the supporting structure from the ambient side to the body side thereof, and one or more attachment features that are adapted to connect an ultrasound probe housing of an ultrasound device to the ambient side of the supporting structure, the ultrasound probe housing comprising an ambient side and a body side and containing a plurality of ultrasound probes configured to generate ultrasound waves, the ultrasound waves being configured to produce images of inside the body of a patient. The one or more attachment features are configured to connect the ultrasound probe housing to the ambient side of the supporting structure such that at least a portion of the body side of the ultrasound probe housing is disposed within the opening and facing toward the body of the patient when the supporting structure is attached thereto.

In one embodiment of the foregoing supporting structure, the ultrasound device further comprises a guide channel cut out or aperture that passes through the ultrasound probe housing from the ambient side to the body side thereof and the one or more attachment features are configured to connect the ultrasound probe housing to the ambient side of the supporting structure such that at least a portion of the guide channel cut out or aperture is situated above the opening.

In another embodiment of the foregoing supporting structure, the supporting structure comprises one of a sleeve, a cuff, a C-clamp, a U-clamp, or an adhesive strip.

In yet another embodiment of the foregoing supporting structure, the one or more attachment features comprise: a male connector that is configured to mate with a female connector of the ultrasound probe housing; a female connector that is configured to mate with a male connector of the ultrasound probe housing; a first magnet that is configured to magnetically connect to a second magnet or a ferromagnetic metal component of the ultrasound probe housing; a ferromagnetic metal component that is configured to magnetically connect to a magnet of the ultrasound probe housing; a rail that is configured to engage with a groove of the ultrasound probe housing; a groove that is configured to engage with a rail of the ultrasound housing; a hook that is configured to mate with an eye of the ultrasound probe housing; an eye that is configured to mate with a hook of the ultrasound probe housing; or an attachment arm that is configured to engage with the ultrasound probe housing.

In still another embodiment of the foregoing supporting structure, the ambient side of the supporting structure comprises a recessed frame that surrounds the opening, the one or more attachment features comprise one or more first mating elements arranged on the recessed frame, and the one or more first mating elements are configured to respectively mate with one or more second mating elements included on at least one tab that extends from an edge of the ultrasound probe housing.

In a further embodiment of the foregoing supporting structure, the ambient side of the supporting structure comprises a rectangular recess that surrounds the opening, the one or more attachment features comprise grooves respectively formed in opposite sidewalls of the rectangular recess, the grooves being configured to receive corresponding rails that extend from opposite edges of the ultrasound probe housing, and the rails are slidable within the grooves to enable lateral movement of the ultrasound device within the recess while the ultrasound device is connected to the supporting structure.

In a still further embodiment of the foregoing supporting structure, the ambient side of the supporting structure comprises a rectangular recess that surrounds the opening, the one or more attachment features comprise rails respectively extending from opposite sidewalls of the rectangular recess, the rails being configured to engage with corresponding grooves that are formed in opposite edges of the ultrasound probe housing, and the grooves are slidable along the rails to enable lateral movement of the ultrasound device within the recess while the ultrasound device is connected to the supporting structure.

In a yet further embodiment of the foregoing supporting structure, the ambient side of the supporting structure comprises a rectangular recess that surrounds the opening, the one or more attachment features comprise grooves respectively formed in opposite sidewalls of the rectangular recess, the grooves being configured to receive corresponding rails that extend from opposite edges of a frame to which the ultrasound probe housing is attached and in which the ultrasound probe housing is slidable in a first direction, and the rails are slidable within the grooves to enable movement of the frame within the recess in a second direction that is perpendicular to the first direction while the frame is connected to the supporting structure.

In another embodiment of the foregoing supporting structure, the ambient side of the supporting structure comprises a rectangular recess that surrounds the opening, the one or more attachment features comprise rails respectively extending from opposite sidewalls of the rectangular recess, the rails being configured to engage with corresponding grooves that are formed in opposite edges of a frame to which the ultrasound probe housing is attached and in which the ultrasound probe housing is slidable in a first direction, and the grooves are slidable along the rails to enable movement of the frame within the recess in a second direction that is perpendicular to the first direction while the frame is connected to the supporting structure.

In yet another embodiment of the foregoing supporting structure, the ambient side of the supporting structure comprises a recess that surrounds the opening and the one or more attachment features comprise a retractable attachment arm that extends from a sidewall of the recess.

In still another embodiment of the foregoing supporting structure, the ambient side of the supporting structure comprises a recess that surrounds the opening and the one or more attachment features comprise a hook attached to or integrated with a sidewall of the recess, the hook being configured to engage with an eye attached to or integrated with an edge of the ultrasound probe housing.

In a further embodiment of the foregoing supporting structure, the ambient side of the supporting structure comprises a recess that surrounds the opening and the one or more attachment features comprise a female snap connector attached to or integrated with a sidewall of the recess, the female snap connector being configured to engage with a male snap connector connected to or integrated with an edge of the ultrasound probe housing.

In a still further embodiment of the foregoing supporting structure, the ambient side of the supporting structure comprises a recess that surrounds the opening and the one or more attachment features comprise a male snap connector attached to or integrated with a sidewall of the recess, the male snap connector being configured to engage with a female snap connector connected to or integrated with an edge of the ultrasound probe housing.

In a yet further embodiment of the foregoing supporting structure, the supporting structure comprises a cuff or a sleeve and further comprises an integrated tourniquet. The integrated tourniquet may comprise a cord, tube or strap that is configured to be manually tightened around a limb of the patient. The integrated tourniquet may comprise an inflatable tube, ring, or bladder.

In another embodiment of the foregoing supporting structure, the supporting structure comprises a cuff or a sleeve having a closure means for adjoining two ends thereof around a limb of the patient.

In yet another embodiment of the foregoing supporting structure, the ambient side of the supporting structure comprises a circular recessed frame that surrounds the opening, the one or more attachment features comprise one or more first mating elements arranged on the circular recessed frame, and the ultrasound probe housing is substantially disk-shaped and comprises a circumferential outer edge from which extends one or more mating members comprising one or more second mating elements that are configured to respectively mate with the one or more first mating elements.

In still another embodiment of the foregoing supporting structure, the ambient side of the supporting structure comprises a circular recess that surrounds the opening, the ultrasound probe housing is substantially disk-shaped, and the one or more attachment features comprise one or more ball bearings that are disposed between a circular sidewall of the circular recess and a circumferential outer edge of the ultrasound probe housing when the ultrasound probe housing is disposed within the circular recess, the one or more ball bearings being configured to enable circumferential rotation of the ultrasound device within the circular recess while the ultrasound device is connected to the supporting structure.

In a further embodiment of the foregoing supporting structure, the ambient side of the supporting structure comprises a circular recess that surrounds the opening, the ultrasound probe housing is substantially disk-shaped, and the one or more attachment features comprise a groove that is formed in a circular sidewall of the circular recess, the groove being configured to receive a rail that extends from a circumferential outer edge of the ultrasound probe housing when the ultrasound probe housing is disposed within the circular recess, the rail being slidable within the groove to enable circumferential rotation of the ultrasound device within the circular recess while the ultrasound device is connected to the supporting structure.

In a still further embodiment of the foregoing supporting structure, the ambient side of the supporting structure comprises a circular recess that surrounds the opening, the ultrasound probe housing is substantially disk-shaped, and the one or more attachment features comprise a rail that extends from a circular sidewall of the circular recess, the rail being configured to engage with a groove formed in a circumferential outer edge of the ultrasound probe housing when the ultrasound probe housing is disposed within the circular recess, the groove being slidable on the rail to enable circumferential rotation of the ultrasound device within the circular recess while the ultrasound device is connected to the supporting structure.

In a yet further embodiment of the foregoing supporting structure, the supporting structure further comprises a pivot point attached to the ambient side thereof and an arm that is rotatable about the pivot point and over the opening on the ambient side of the supporting structure, and the one or more attachment features are configured to attach the ultrasound probe housing to a bottom of the arm. In further accordance with such an embodiment, the one or more attachment features may be configured to slidably attach the ultrasound probe housing to the bottom of the arm, the arm may comprise an elongated opening that passes fully therethrough, and the ultrasound probe housing may comprise a guide channel cut-out or aperture that is aligned with the elongated opening when the ultrasound probe housing is slidably attached to the arm such that at least a portion of the guide channel cut-out or aperture is located below the elongated opening as the ultrasound device is moved up and down the arm.

In another embodiment of the foregoing supporting structure, the supporting structure comprises a layer of flexible or semi-flexible material and an adhesive material disposed across at least a portion of the body side thereof to facilitate attachment to the body of the patient. The supporting structure may further comprise a support frame attached to the ambient side thereof that surrounds the opening and includes the one or more attachment features. The supporting structure may further comprise a removable backing layer that is disposed over the body side of the supporting structure. The removable backing layer may be disposed over the body side of the supporting structure such that it covers a bottom of the opening, and the supporting structure may further comprise a layer of ultrasound gel disposed within the opening and a removable top cover that is disposed over the support frame on the ambient side of the supporting structure such that it covers a top of the opening. A numbing agent may be mixed with the layer of ultrasound gel. The supporting structure may further comprise a biosafe layer disposed above or below the layer of ultrasound gel.

In yet another embodiment of the foregoing supporting structure, the opening is fully surrounded by the supporting structure.

In still another embodiment of the foregoing supporting structure, the opening is partially surrounded by the supporting structure.

An ultrasound device is also described herein that comprises a stationary housing component, a rotational housing component, and a plurality of ultrasound probes. The stationary housing component has an ambient side and a body side. The rotational housing component is connected to the stationary housing component and is circumferentially rotatable with respect thereto. The rotational housing component has an ambient side and a body side and comprises a guide channel cut-out or aperture that extends through the rotational housing component from the ambient side to the body side thereof and accommodates the passage of a needle therethrough. The plurality of ultrasound probes are disposed in one or more of the stationary housing component and the rotational housing component and are configured to generate ultrasound waves, the ultrasound waves being configures to produce images of the needle when inserted into a body of a patient.

In one embodiment of the foregoing ultrasound device, the rotational housing component further comprises a needle guide assembly disposed within the guide channel cut-out or aperture, the needle guide assembly being adapted to receive the needle that is slidable therein. The needle guide assembly may be connected to the guide channel cut-out or aperture at a pivot point and may be rotatable about the pivot point. The ultrasound device may further comprise a locking mechanism that is operable to lock the needle guide assembly at a selected angular position.

In another embodiment of the foregoing ultrasound device, the stationary housing component comprises a semicircular outer edge within which is formed a semicircular channel and the rotational housing component is generally disk-shaped and comprises a circumferential outer edge that comprises a semicircular rail that is inserted within the semicircular channel in an interlocking manner and that is slidably moveable within the semicircular channel to enable the circumferential rotation of the rotational housing component with respect to the stationary housing component.

In yet another embodiment of the foregoing ultrasound device, the stationary housing component comprises a semicircular outer edge upon which is formed a semicircular rail and the rotational housing component is generally disk-shaped and comprises a circumferential outer edge within which is formed a semicircular channel into which the semicircular rail is inserted in an interlocking manner, the semicircular channel being slidably moveable on the semicircular rail to enable the circumferential rotation of the rotational housing component with respect to the stationary housing component.

In still another embodiment of the foregoing ultrasound device, the rotational housing component further comprises a handle on the ambient side thereof.

In a further embodiment of the foregoing ultrasound device, the plurality of ultrasound probes are disposed within the stationary housing component.

In a still further embodiment of the foregoing ultrasound device, the plurality of ultrasound probes are disposed within the rotational housing component.

In a yet further embodiment of the foregoing ultrasound device, a first portion of the plurality of ultrasound probes are disposed within the stationary housing component and a second portion of the plurality of ultrasound probes are disposed within the rotational housing component.

In another embodiment of the foregoing ultrasound device, the ultrasound device further comprises a locking mechanism to lock the stationary housing component in a desired rotational position with respect to the stationary housing component.

In yet another embodiment of the foregoing ultrasound device, the stationary housing component further comprises one or more attachment features that are configured to enable the stationary housing component to be attached to a supporting structure that is attachable to the body of the patient. The one or more attachment features may be configured to enable the stationary housing component to be slidably attached to the supporting structure. For example, the one or more attachment features may comprise a guide formed in an edge of the stationary housing component and configured to receive a rail of the supporting structure. As another example, the one or more attachment features comprise a rail formed on an edge of the stationary housing component and configured to be inserted into a guide of the supporting structure.

III. Conclusion

In the foregoing description, it will be readily appreciated by those skilled in the art that modifications may be made to the invention without departing from the concepts disclosed herein. Such modifications are to be considered as included in the following claims unless the claims by their language expressly state otherwise.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. The various embodiments set forth herein are described in terms of exemplary block diagrams and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment.

What is claimed is:

1. A system, comprising:
    an ultrasound device comprising an ultrasound probe housing that contains a plurality of ultrasound probes configured to generate ultrasound waves, wherein the ultrasound waves are configured to produce images of inside a body of a patient, the ultrasound probe housing comprising an ambient side and a body side; and
    a supporting structure configured to be attached to the body of the patient, the supporting structure comprising an ambient side and a body side, the supporting structure including:
        an opening that passes through the supporting structure from the ambient side to the body side thereof, wherein the ambient side of the supporting structure comprises a circular recess that surrounds the opening; and
        one or more attachment features that are adapted to connect the ultrasound probe housing of the ultrasound device to the ambient side of the supporting structure such that at least a portion of the body side of the ultrasound probe housing is adapted to contact the body of the patient and disposed within a first portion of the opening and facing toward the body of the patient when the supporting structure is attached thereto, and such that a second portion of the opening remains exposed after at least the portion of the body side of the ultrasound probe housing is disposed within the first portion of the opening.

2. The system of claim 1, wherein the ultrasound device further comprises:
    a guide channel cut out or aperture that passes through the ultrasound probe housing from the ambient side to the body side thereof and configured to receive a needle; and
    wherein when the ultrasound probe housing is connected to the ambient side of the supporting structure, at least a portion of the guide channel cut out or aperture is aligned with the second portion of the opening such that the needle, when received via the guide channel cut out or aperture, is slidable within a needle guide assembly to enter the body of the patient via the second portion of the opening.

3. The system of claim 2, wherein the needle guide assembly is connected to the guide channel cut out or aperture at a pivot point within the guide channel cut out or aperture and is rotatable within the guide channel cut out or aperture and about the pivot point.

4. The system of claim 1, wherein the supporting structure comprises one of:
    a sleeve;
    a cuff;
    a C-clamp;
    a U-claim; or
    an adhesive strip.

5. The system of claim 1, wherein the one or more attachment features comprise:

a male connector that is configured to mate with a female connector of the ultrasound probe housing;

a female connector that is configured to mate with a male connector of the ultrasound probe housing;

a first magnet that is configured to magnetically connect to a second magnet or a ferromagnetic metal component of the ultrasound probe housing;

a ferromagnetic metal component that is configured to magnetically connect to a magnet of the ultrasound probe housing;

a rail that is configured to engage with a groove of the ultrasound probe housing;

a groove that is configured to engage with a rail of the ultrasound housing;

a hook that is configured to mate with an eye of the ultrasound probe housing;

an eye that is configured to mate with a hook of the ultrasound probe housing; or an attachment arm that is configured to engage with the ultrasound probe housing.

6. The system of claim 1, wherein the ambient side of the supporting structure comprises a recessed frame that surrounds the opening, wherein the one or more attachment features comprise one or more first mating elements arranged on the recessed frame, and wherein the ultrasound probe housing comprises at least one tab that extends from at least one edge thereof and includes one or more second mating elements that are configured to respectively mate with the one or more first mating elements.

7. The system of claim 1, wherein the ambient side of the supporting structure comprises a recessed frame that surrounds the opening, wherein the one or more attachment features comprise one or more first mating elements arranged on the recessed frame, and wherein the ultrasound probe housing is substantially disk-shaped and comprises a circumferential outer edge from which extends one or more mating members comprising one or more second mating elements that are configured to respectively mate with the one or more first mating elements.

8. The system of claim 1, wherein the ultrasound probe housing is substantially disk-shaped, and wherein the one or more attachment features comprise one or more ball bearings that are disposed between a circular sidewall of the circular recess and a circumferential outer edge of the ultrasound probe housing when the ultrasound probe housing is disposed within the circular recess, the one or more ball bearing being configured to enable circumferential rotation of the ultrasound device within the circular recess while the ultrasound device is connected to the supporting structure.

9. The system of claim 1, wherein the ultrasound probe housing is substantially disk-shaped, and wherein the one or more attachment features comprise a groove that is formed in a circular sidewall of the circular recess, the groove being configured to receive a rail that extends from a circumferential outer edge of the ultrasound probe housing when the ultrasound probe housing is disposed within the circular recess, the rail being slidable within the groove to enable circumferential rotation of the ultrasound device within the circular recess while the ultrasound device is connected to the supporting structure.

10. The system of claim 1, wherein the ultrasound probe housing is substantially disk-shaped, and wherein the one or more attachment features comprise a rail that extends from a circular sidewall of the circular recess, the rail being configured to engage with a groove formed in a circumferential outer edge of the ultrasound probe housing when the ultrasound probe housing is disposed within the circular recess, the groove being slidable on the rail to enable circumferential rotation of the ultrasound device within the circular recess while the ultrasound device is connected to the supporting structure.

11. The system of claim 1, wherein the supporting structure comprises a cuff or a sleeve and further comprises an integrated tourniquet.

12. The system of claim 11, wherein the integrated tourniquet comprises a cord, tube or strap that is configured to be manually tightened around a limb of the patient.

13. The system of claim 11, wherein the integrated tourniquet comprises an inflatable tube, ring, or bladder.

14. The system of claim 1, wherein the supporting structure comprises a cuff or a sleeve having a closure means for adjoining two ends thereof around a limb of the patient.

15. A supporting structure configured to be attached to a body of a patient, the supporting structure comprising:

an ambient side;

a body side opposite the ambient side;

an opening that passes through the supporting structure from the ambient side to the body side thereof, wherein the ambient side of the supporting structure comprises a circular recess that surrounds the opening; and one or more attachment features that are adapted to connect an ultrasound probe housing of an ultrasound device to the ambient side of the supporting structure, the ultrasound probe housing comprising an ambient side and a body side and containing a plurality of ultrasound probes configured to generate ultrasound waves, the ultrasound waves being configured to produce images of inside the body of the patient;

wherein the one or more attachment features are configured to connect the ultrasound probe housing to the ambient side of the supporting structure such that at least a portion of the body side of the ultrasound probe housing is adapted to contact the body of the patient and disposed within a first portion of the opening and facing toward the body of the patient when the supporting structure is attached thereto, and such that a second portion of the opening remains exposed after at least the portion of the body side of the ultrasound probe housing is disposed within the first portion of the opening.

16. The supporting structure of claim 15, wherein the ultrasound device further comprises:

a guide channel cut out or aperture that passes through the ultrasound probe housing from the ambient side to the body side thereof; and wherein the one or more attachment features are configured to connect the ultrasound probe housing to the ambient side of the supporting structure such that at least a portion of the guide channel cut out or aperture is aligned with the second portion of the opening.

17. The supporting structure of claim 15, wherein the supporting structure comprises one of:

a sleeve;

a cuff;

a C-clamp;

a U-clamp; or an adhesive strip.

18. The supporting structure of claim 15, wherein the one or more attachment features comprise:

a male connector that is configured to mate with a female connector of the ultrasound probe housing;

a female connector that is configured to mate with a male connector of the ultrasound probe housing;

a first magnet that is configured to magnetically connect to a second magnet or a ferromagnetic metal component of the ultrasound probe housing;

a ferromagnetic metal component that is configured to magnetically connect to a magnet of the ultrasound probe housing;

a rail that is configured to engage with a groove of the ultrasound probe housing;

a groove that is configured to engage with a rail of the ultrasound housing;

a hook that is configured to mate with an eye of the ultrasound probe housing;

an eye that is configured to mate with a hook of the ultrasound probe housing; or an attachment arm that is configured to engage with the ultrasound probe housing.

19. The supporting structure of claim 15, wherein the ambient side of the supporting structure comprises a recessed frame that surrounds the opening, wherein the one or more attachment features comprise one or more first mating elements arranged on the recessed frame, and wherein the one or more first mating elements are configured to respectively mate with one or more second mating elements included on at least one tab that extends from an edge of the ultrasound probe housing.

20. The supporting structure of claim 15, wherein the ambient side of the supporting structure comprises a recessed frame that surrounds the opening, wherein the one or more attachment features comprise one or more first mating elements arranged on the recessed frame, and wherein the ultrasound probe housing is substantially disk-shaped and comprises a circumferential outer edge from which extends one or more mating members comprising one or more second mating elements that are configured to respectively mate with the one or more first mating elements.

21. The supporting structure of claim 15, wherein the ultrasound probe housing is substantially disk-shaped, and wherein the one or more attachment features comprise one or more ball bearings that are disposed between a circular sidewall of the circular recess and a circumferential outer edge of the ultrasound probe housing when the ultrasound probe housing is disposed within the circular recess, the one or more ball bearing being configured to enable circumferential rotation of the ultrasound device within the circular recess while the ultrasound device is connected to the supporting structure.

22. The supporting structure of claim 15, wherein the ultrasound probe housing is substantially disk-shaped, and wherein the one or more attachment features comprise a groove that is formed in a circular sidewall of the circular recess, the groove being configured to receive a rail that extends from a circumferential outer edge of the ultrasound probe housing when the ultrasound probe housing is disposed within the circular recess, the rail being slidable within the groove to enable circumferential rotation of the ultrasound device within the circular recess while the ultrasound device is connected to the supporting structure.

23. The supporting structure of claim 15, wherein the ultrasound probe housing is substantially disk-shaped, and wherein the one or more attachment features comprise a rail that extends from a circular sidewall of the circular recess, the rail being configured to engage with a groove formed in a circumferential outer edge of the ultrasound probe housing when the ultrasound probe housing is disposed within the circular recess, the groove being slidable on the rail to enable circumferential rotation of the ultrasound device within the circular recess while the ultrasound device is connected to the supporting structure.

24. The supporting structure of claim 15, wherein the supporting structure comprises a cuff or a sleeve and further comprises an integrated tourniquet.

25. The supporting structure of claim 24, wherein the integrated tourniquet comprises a cord, tube or strap that is configured to be manually tightened around a limb of the patient.

26. The supporting structure of claim 24, wherein the integrated tourniquet comprises an inflatable tube, ring, or bladder.

27. The supporting structure of claim 15, wherein the supporting structure comprises a cuff or a sleeve having a closure means for adjoining two ends thereof around a limb of the patient.

28. The supporting structure of claim 15, wherein the supporting structure comprises a layer of flexible or semi-flexible material and an adhesive material disposed across at least a portion of the body side thereof to facilitate attachment to the body of the patient.

29. The supporting structure of claim 15, further comprising a removable backing layer that is disposed over the body side of the supporting structure.

30. A system, comprising:
an ultrasound device comprising an ultrasound probe housing that contains a plurality of ultrasound probes configured to generate ultrasound waves, wherein the ultrasound waves are configured to produce images of inside a body of a patient, the ultrasound probe housing comprising an ambient side and a body side; and
a supporting structure configured to be attached to the body of the patient, the supporting structure comprising an ambient side and a body side, the supporting structure including:
an opening that passes through the supporting structure from the ambient side to the body side thereof, wherein the ambient side of the supporting structure comprises a circular recessed frame that at least partially surrounds the opening; and
one or more attachment features that are adapted to connect the ultrasound probe housing of the ultrasound device to the ambient side of the supporting structure such that at least a portion of the body side of the ultrasound probe housing is disposed within the opening and facing toward the body of the patient when the supporting structure is attached thereto, wherein the ambient side of the supporting structure comprises a recessed frame that at least partially surrounds the opening, wherein the one or more attachment features comprise one or more first mating elements arranged on the recessed frame, and wherein the ultrasound probe housing comprises at least one tab that extends from at least one edge thereof and includes one or more second mating elements that are configured to respectively mate with the one or more first mating elements.

* * * * *

UNITED STATES PATENT AND TRADEMARK OFFICE
CERTIFICATE OF CORRECTION

PATENT NO. : 12,303,323 B2
APPLICATION NO. : 19/007186
DATED : May 20, 2025
INVENTOR(S) : Adams et al.

Page 1 of 1

It is certified that error appears in the above-identified patent and that said Letters Patent is hereby corrected as shown below:

On the Title Page

Column 1, under "Related U.S. Application Data", delete "60" and insert -- 62 --, therefor.

In the Claims

In Column 46, Claim 4, Line 64, delete "U-claim;" and insert -- U-clamp; --, therefor.

In Column 47, Claim 8, Line 47, delete "bearing" and insert -- bearings --, therefor.

In Column 49, Claim 21, Line 44, delete "bearing" and insert -- bearings --, therefor.

In Column 50, Claim 30, Line 44, delete "recessed frame" and insert -- recess --, therefor.

Signed and Sealed this
Fifth Day of August, 2025

Coke Morgan Stewart
*Acting Director of the United States Patent and Trademark Office*